(12) United States Patent
Prissette et al.

(10) Patent No.: US 11,781,131 B2
(45) Date of Patent: Oct. 10, 2023

(54) CRISPR/CAS DROPOUT SCREENING PLATFORM TO REVEAL GENETIC VULNERABILITIES ASSOCIATED WITH TAU AGGREGATION

(71) Applicant: Regeneron Pharmaceuticals, Inc., Tarrytown, NY (US)

(72) Inventors: Marine Prissette, Brooklyn, NY (US); Matthew Koss, Pleasantville, NY (US); Yu Bai, Scarsdale, NY (US); Brian Zambrowicz, Sleepy Hollow, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 690 days.

(21) Appl. No.: 16/821,384

(22) Filed: Mar. 17, 2020

(65) Prior Publication Data

US 2020/0299681 A1  Sep. 24, 2020

Related U.S. Application Data

(60) Provisional application No. 62/820,101, filed on Mar. 18, 2019.

(51) Int. Cl.
| | | |
|---|---|---|
| *C07H 21/04* | (2006.01) | |
| *C12N 15/10* | (2006.01) | |
| *C12N 9/22* | (2006.01) | |
| *C12N 15/113* | (2010.01) | |

(52) U.S. Cl.
CPC .......... *C12N 15/1082* (2013.01); *C12N 9/22* (2013.01); *C12N 15/1079* (2013.01); *C12N 15/113* (2013.01); *C12N 2310/20* (2017.05)

(58) Field of Classification Search
None
See application file for complete search history.

(56) References Cited

U.S. PATENT DOCUMENTS

| | | |
|---|---|---|
| 9,910,048 B2 | 3/2018 | Diamond et al. |
| 11,001,829 B2 | 5/2021 | Zhang et al. |
| 11,149,267 B2 | 10/2021 | Wang et al. |
| 2016/0272965 A1 | 9/2016 | Zhang et al. |
| 2017/0204407 A1 | 7/2017 | Gilbert et al. |
| 2018/0291370 A1 | 10/2018 | Gersbach et al. |
| 2018/0305704 A1 | 10/2018 | Zhang |
| 2019/0032155 A1 | 1/2019 | Gong et al. |
| 2019/0284572 A1 | 9/2019 | Hunt et al. |
| 2020/0165601 A1 | 5/2020 | Zhang et al. |
| 2020/0299679 A1 | 9/2020 | Fury et al. |
| 2020/0299681 A1 | 9/2020 | Prissette et al. |
| 2020/0299682 A1 | 9/2020 | Prissette et al. |
| 2021/0009949 A1 | 1/2021 | Prissette et al. |

FOREIGN PATENT DOCUMENTS

| | | |
|---|---|---|
| EP | 3011033 B1 | 2/2020 |
| WO | WO 2014/008404 A1 | 1/2014 |
| WO | WO 2014/089104 A1 | 6/2014 |
| WO | WO 2015/122922 A1 | 8/2015 |
| WO | WO 2017/015637 A1 | 1/2017 |
| WO | WO 2017/100343 A1 | 6/2017 |
| WO | WO 2017/172764 A1 | 10/2017 |
| WO | WO 2018/127519 A1 | 7/2018 |
| WO | WO 2018/224531 A1 | 12/2018 |
| WO | WO 2019/010384 A1 | 1/2019 |
| WO | WO 2019/028032 A1 | 2/2019 |
| WO | WO 2019/183123 A1 | 9/2019 |
| WO | WO 2020/190927 A1 | 9/2020 |
| WO | WO 2020/190932 A1 | 9/2020 |
| WO | WO 2020/190944 A1 | 9/2020 |
| WO | WO 2020/252340 A1 | 12/2020 |

OTHER PUBLICATIONS

Esteves-Villanueva, Jose O., Hanna Trzeciakiewicz, and Sanela Martic. "A protein-based electrochemical biosensor for detection of tau protein, a neurodegenerative disease biomarker." Analyst 139.11 (2014): 2823-2831.*
Prissette et al. "Disruption of nuclear envelope integrity as a possible initiating event in tauopathies." Cell Reports 40.8 (2022): 111249.*
"The 96th Annual Meeting of the Physiological Society of Japan," Journal of Physiological Sciences, Springer Japan KK, 69(Suppl 1), (2019).
Anonymous, "Identification of genetic regulators for intracellular aggregation by genome-wide CRISPR screening," 2016 Fiscal Year Annual Research Report, The University of Tokyo, KAKEN, 2 pages, (2018).
Anonymous, Abstracts: Oral Presentations, Cell Biology, ASCB Annual Meeting, 84 pages, (2016).
Chen et al., "Compromised function of the ESCRT pathway promotes endolysosomal escape of tau seeds and propagation of tau aggregation," J. Biol. Chem., 294(50):18952-18966, (2019).
Chiu et al., "Identification of Calcium and Integrin-Binding Protein 1 as a Novel Regulator of Production of Amyloid β Peptide Using CRISPR/Cas9-based Screening System," FASEB J., 34(6):7661-7674, (2020).
Kampmann, "CRISPRi and CRISPRa Screens in Mammalian Cells for Precision Biology and Medicine," ACS Chem. Biol., 13(2):406-416, (2017).
Nathaniel et al., "Elucidating Cellular Trafficking Pathways Controlling Prion-like Spread of Tau Aggregation Using CRISPR Interference Screens [abstract]," Abstracts; Poster Presentations, Cell Biology 2016, ASCB Annual Meeting, P887, (2016).
Sanders et al., "Distinct Tau Prion Strains Propagate in Cells and Mice and Define Different Tauopathies," Neuron, 82(6):1271-1288, (2014).

(Continued)

*Primary Examiner* — Kimberly Chong
(74) *Attorney, Agent, or Firm* — Yongjin Choi; Alston & Bird LLP

(57) ABSTRACT

Cas-protein-ready tau bio sensor cells, CRISPR/Cas synergistic activation mediator (SAM)-ready tau biosensor cells, and methods of making and using such cells to screen for genetic vulnerability associated with tau aggregation are provided.

36 Claims, 29 Drawing Sheets

Specification includes a Sequence Listing.

(56) References Cited

OTHER PUBLICATIONS

Wu et al., "Neuronal activity enhances tau propagation and tau pathology in vivo," Nat. Neurosci., 19(8):1085-1092, (2016).
WIPO Application No. PCT/US2020/023121, PCT International Search Report and Written Opinion of the International Searching Authority dated May 27, 2020.
Anders et al., "Differential expression analysis for sequence count data," Genome Biol., 11:R106, pp. 1-12, (2010).
Bajar et al., "A Guide to Fluorescent Protein FRET Pairs," Sensors (Basel), 16:E1488, pp. 1-24, (2016).
Bennett et al., "Enhanced Tau Aggregation in the Presence of Amyloid β," Am. J. Pathol., 187(7):1601-1612, (2017).
Chen et al., "Genome-wide CRISPR Screen in a Mouse Model of Tumor Growth and Metastasis," Cell, 160(6):1246-1260 plus supplementary materials, (2015).
Furman et al., "Sensitive Detection of Proteopathic Seeding Activity with FRET Flow Cytometry," J. Vis. Exp., 106:e53205, pp. 1-12, (2015).
Hart et al., "High-Resolution CRISPR Screens Reveal Fitness Genes and Genotype-Specific Cancer Liabilities," Cell, 163(6):1515-1526, (2015).
Holmes et al., "Proteopathic tau seeding predicts tauopathy in vivo," Proc. Natl. Acad. Sci. U.S.A., 111(41):E4376-E4385, (2014).
Joung et al., "Genome-scale CRISPR-Cas9 knockout and transcriptional activation screening," Nat. Protoc., 12(4):828-863, (2017).
Jucker et al., "Self-propagation of pathogenic protein aggregates in neurodegenerative diseases," Nature, 501(7465):45-51, (2013).
Kampmann, "A CRISPR Approach to Neurodegenerative Diseases," Trends Mol. Med., 23(6):483-485, (2017).
Kaufman et al., "Tau Prion Strains Dictate Patterns of Cell Pathology, Progression Rate, and Regional Vulnerability In Vivo," Neuron, 92(4)796-812, (2016).
Kfoury et al., "Trans-cellular Propagation of Tau Aggregation by Fibrillar Species," The Journal of Biological Chemistry, 287(23):19440-19451, (2012).
Konermann et al., "Genome-scale transcriptional activation by an engineered CRISPR-Cas9 complex," Nature, 517(7536):583-588 plus supplementary materials, (2015).
Nagai et al., "Astrocytes expressing ALS-iinked mutated SOD1 release factors selectively toxic to motor neurons," Nat. Neurosci., 10(5):615-622, (2007).
Nicholls et al., "Characterization of TauC3 antibody and demonstration of its potential to block tau propagation," PLOS ONE, 12(5):e0177914, 11 pages, (2017).
Nobuhara et al., "Tau Antibody Targeting Pathological Species Blocks Neuronal Uptake and Interneuron Propagation of Tau in Vitro," Am. J. Pathol., 187(6):1399-1412, (2017).

Park et al., "A genome-wide CRISPR screen identifies a restricted set of HIV host dependency factors," Nat. Genet., 49(2):193-203 plus online methods, (2017).
Reczek et al., "A CRISPR screen identifies a pathway required for paraquat-induced cell death," Nat. Chem. Biol., 13(12):1274-1279 plus online methods, (2017).
Sanjana et al., "Improved vectors and genome-wide libraries for CRISPR screening," Nat. Methods, 11(8):783-784, (2014).
Shalem et al., "Genome-Scale CRISPR-Cas9 Knockout Screening in Human Cells," Science, 343:84-87 and Supplementary Material, (2014).
Tzelepis et al., "A CRISPR Dropout Screen Identifies Genetic Vulnerabilities and Therapeutic Targets in Acute Myeloid Leukemia," Cell Reports, 17:1193-1205, (2016).
Wang et al., "Gene Essentiality Profiling Reveals Gene Networks and Synthetic Lethal Interactions with Oncogenic Ras," Cell, 168(5):890-903 plus supplemental materials, (2017).
Wang et al., "Identification and characterization of essential genes in the human genome," Science, 350(6264):1096-1101, (2015).
Chakrabarti et al., "Target-Specific Precision of CRISPR-Mediated Genome Editing," Mol. Cell, 73(4):699-713, (2019).
CRISPR 101: A Desktop Resource, Addgene, 2nd ed., 195 pages, (2017).
Li et al., "MAGeCK enables robust identification of essential genes from genome-scale CRISPR/Cas9 knockout screens," Genome Biol., 15(12):554, 12 pages, (2014).
Miles et al., "Design, execution, and analysis of pooled in vitro CRISPR/Cas9 screens," FEBS J., 283(17):3170-3180, (2016).
Ong et al., "Optimised metrics for CRISPR-KO screens with second-generation gRNA libraries," Sci. Rep., 7(1):7384, 10 pages, (2017).
Agrotis et al., "A new age in functional genomics using CRISPR/Cas9 in arrayed library screening," Front. Genet., 6:300, (2015).
Goedert, "Tau filaments in neurodegenerative diseases," FEBS Lett., 592(14):2383-2391, (2018).
Murugan et al., "The Revolution Continues: Newly Discovered Systems Expand the CRISPR-Cas Toolkit," Mol. Cell 68(1):15-25, (2017).
Nakade et al., "Cas9, Cpf1 and C2c1/2/3—What's next?," Bioengineered, 8(3):265-273, (2017).
Park et al., "Cpf1-Database: web-based genome-wide guide RNA library design for gene knockout screens using CRISPR-Cpf1," Bioinformatics, 34(6):1077-1079, (2018).
Tycko et al., "Pairwise library screen systematically interrogates *Staphylococcus aureus* Cas9 specificity in human cells," Nat. Commun. 9(1):2962, (2018).

* cited by examiner

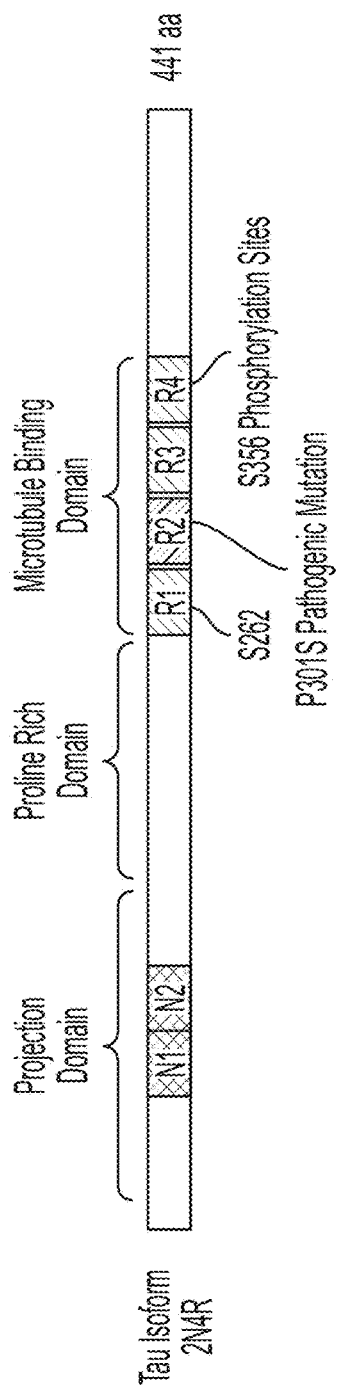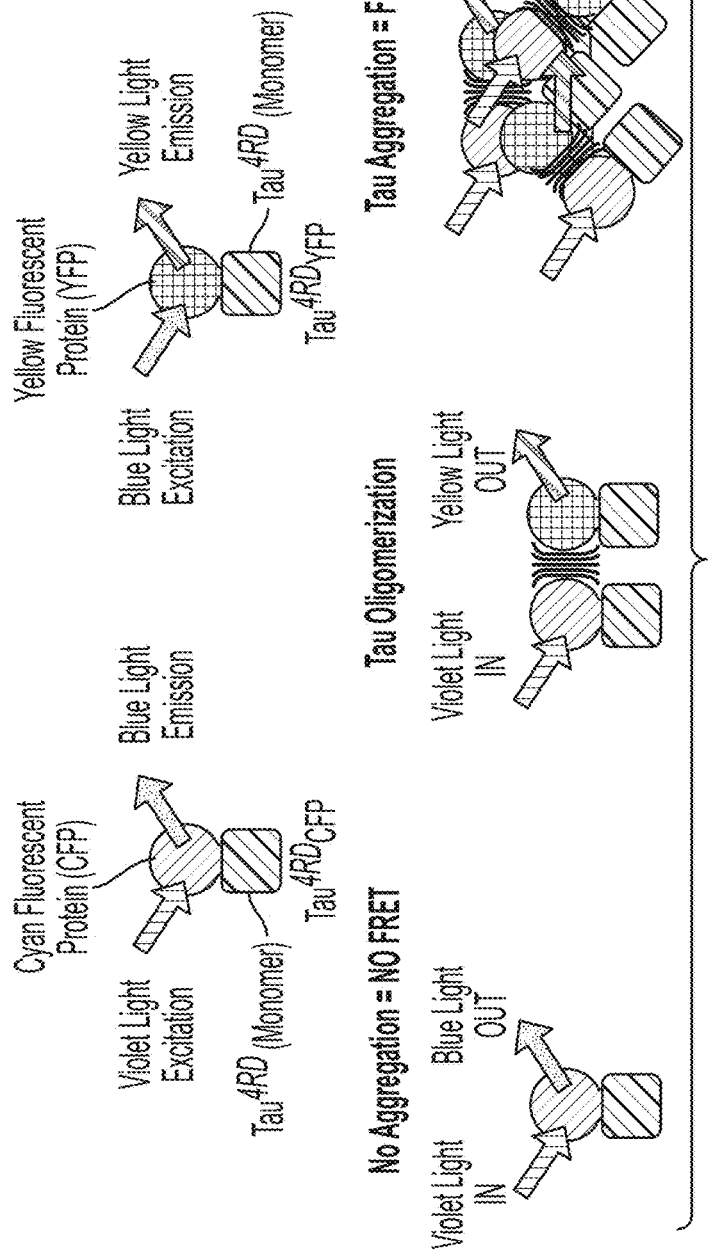

SEQUENCE LISTING

```
<160> NUMBER OF SEQ ID NOS: 43

<210> SEQ ID NO 1
<211> LENGTH: 31
<212> TYPE: PRT
<213> ORGANISM: Artificial Sequence
<220> FEATURE:
<223> OTHER INFORMATION: Synthetic

<400> SEQUENCE: 1

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic

<400> SEQUENCE: 2

Val Gln Ile Ile Asn Lys Lys Leu Asp Leu Ser Asn Val Gln Ser Lys
1               5                   10                  15
```

Cys Gly Ser Lys Asp Asn Ile Lys His Val Pro Gly Gly Gly Ser
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic

<400> SEQUENCE: 3

Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Synthetic

<400> SEQUENCE: 4

Val Glu Val Lys Ser Glu Lys Leu Asp Phe Lys Asp Arg Val Gln Ser
1               5                   10                  15

Lys Ile Gly Ser Leu Asp Asn Ile Thr His Val Pro Gly Gly Gly Asn
            20                  25                  30

<210> SEQ ID NO 5
<211> LENGTH: 93
<212> TYPE: DNA
<213> ORGANISM: Artificial Sequence
<220> FEATURE:
<223> OTHER INFORMATION: Synthetic

<400> SEQUENCE: 5
cagacagccc ccgtgcccat gccagacctg aagaatgtca agtccaagat cggctccact     60
gagaacctga agcaccagcc gggaggcggg aag                                  93

<210> SEQ ID NO 6
<211> LENGTH: 93
<212> TYPE: DNA
<213> ORGANISM: Artificial Sequence
<220> FEATURE:
<223> OTHER INFORMATION: Synthetic

<400> SEQUENCE: 6
gtgcagataa ttaataagaa gctggatctt agcaacgtcc agtccaagtg tggctcaaag     60
gataatatca acacgtccc gggaggcggc agt                                   93

<210> SEQ ID NO 7
<211> LENGTH: 93
<212> TYPE: DNA
<213> ORGANISM: Artificial Sequence
<220> FEATURE:
<223> OTHER INFORMATION: Synthetic

<400> SEQUENCE: 7
gtgcaaatag tctacaaacc agttgacctg agcaaggtga cctccaagtg tggctcatta     60
ggcaacatcc atcataaacc aggaggtggc cag                                  93

<210> SEQ ID NO 8

```
<211> LENGTH: 96
<212> TYPE: DNA
<213> ORGANISM: Artificial Sequence
<220> FEATURE:
<223> OTHER INFORMATION: Synthetic

<400> SEQUENCE: 8
gtggaagtaa aatctgagaa gcttgacttc aaggacagag tccagtcgaa gattgggtcc    60
ctggacaata tcacccacgt ccctggcgga ggaaat                              96

<210> SEQ ID NO 9
<211> LENGTH: 133
<212> TYPE: PRT
<213> ORGANISM: Artificial Sequence
<220> FEATURE:
<223> OTHER INFORMATION: Synthetic

<400> SEQUENCE: 9

Leu Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
            20                  25                  30

Val Gln Ile Ile Asn Lys Lys Leu Asp Leu Ser Asn Val Gln Ser Lys
        35                  40                  45

Cys Gly Ser Lys Asp Asn Ile Lys His Val Pro Gly Gly Gly Ser Val
    50                  55                  60

Gln Ile Val Tyr Lys Pro Val Asp Leu Ser Lys Val Thr Ser Lys Cys
65                  70                  75                  80

Gly Ser Leu Gly Asn Ile His His Lys Pro Gly Gly Gly Gln Val Glu
                85                  90                  95

Val Lys Ser Glu Lys Leu Asp Phe Lys Asp Arg Val Gln Ser Lys Ile
            100                 105                 110

Gly Ser Leu Asp Asn Ile Thr His Val Pro Gly Gly Gly Asn Lys Lys
        115                 120                 125

Ile Glu Thr His Lys
    130

<210> SEQ ID NO 10
<211> LENGTH: 399
<212> TYPE: DNA
<213> ORGANISM: Artificial Sequence
<220> FEATURE:
<223> OTHER INFORMATION: Synthetic

<400> SEQUENCE: 10
ctgcagacag cccccgtgcc catgccagac ctgaagaatg tcaagtccaa gatcggctcc    60
actgagaacc tgaagcacca gccgggaggc gggaaggtgc agataattaa taagaagctg   120
gatcttagca acgtccagtc caagtgtggc tcaaaggata tatcaaaca cgtcccggga    180 ggcggcagtg tgcaaatagt ctacaaacca gttgacctga gcaaggtgac ctccaagtgt   240
ggctcattag caacatcca tcataaacca ggaggtggcc aggtggaagt aaaatctgag   300
aagcttgact tcaaggacag agtccagtcg aagattgggt ccctggacaa tatcacccac   360
gtccctggcg gaggaaataa aaagattgaa acccacaag                          399

<210> SEQ ID NO 11
<211> LENGTH: 133
<212> TYPE: PRT
<213> ORGANISM: Artificial Sequence
<220> FEATURE:
```

<223> OTHER INFORMATION: Synthetic

<400> SEQUENCE: 11

```
Leu Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
            20                  25                  30

Val Gln Ile Ile Asn Lys Lys Leu Asp Leu Ser Asn Val Gln Ser Lys
        35                  40                  45

Cys Gly Ser Lys Asp Asn Ile Lys His Val Ser Gly Gly Gly Ser Val
    50                  55                  60

Gln Ile Val Tyr Lys Pro Val Asp Leu Ser Lys Val Thr Ser Lys Cys
65                  70                  75                  80

Gly Ser Leu Gly Asn Ile His His Lys Pro Gly Gly Gly Gln Val Glu
                85                  90                  95

Val Lys Ser Glu Lys Leu Asp Phe Lys Asp Arg Val Gln Ser Lys Ile
            100                 105                 110

Gly Ser Leu Asp Asn Ile Thr His Val Pro Gly Gly Gly Asn Lys Lys
        115                 120                 125

Ile Glu Thr His Lys
    130
```

<210> SEQ ID NO 12
<211> LENGTH: 399
<212> TYPE: DNA
<213> ORGANISM: Artificial Sequence
<220> FEATURE:
<223> OTHER INFORMATION: Synthetic

<400> SEQUENCE: 12

```
ctgcagacag cccccgtgcc catgccagac ctgaagaatg tcaagtccaa gatcggctcc      60
actgagaacc tgaagcacca gccgggaggc gggaaggtgc agataattaa taagaagctg     120
gatcttagca acgtccagtc caagtgtggc tcaaaggata atatcaaaca cgtctcggga     180
ggcggcagtg tgcaaatagt ctacaaacca gttgacctga gcaaggtgac ctccaagtgt     240
ggctcattag gcaacatcca tcataaacca ggaggtggcc aggtggaagt aaaatctgag     300
aagcttgact tcaaggacag agtccagtcg aagattgggt ccctggacaa tatcacccac     360
gtccctggcg gaggaaataa aaagattgaa acccacaag                            399
```

<210> SEQ ID NO 13
<211> LENGTH: 238
<212> TYPE: PRT
<213> ORGANISM: Artificial Sequence
<220> FEATURE:
<223> OTHER INFORMATION: Synthetic

<400> SEQUENCE: 13

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Gln
65                  70                  75                  80
```

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Ile Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 14
<211> LENGTH: 714
<212> TYPE: DNA
<213> ORGANISM: Artificial Sequence
<220> FEATURE:
<223> OTHER INFORMATION: Synthetic

<400> SEQUENCE: 14
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctgggg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacatcag ccacaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga agcgcgatca catggtcctg   660
ctggagttcg tgaccgccgc cgggatcact ctcggcatgg acgagctgta caag         714

<210> SEQ ID NO 15
<211> LENGTH: 236
<212> TYPE: PRT
<213> ORGANISM: Artificial Sequence
<220> FEATURE:
<223> OTHER INFORMATION: Synthetic

<400> SEQUENCE: 15

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu

```
                    20                  25                  30
Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu
225                 230                 235

<210> SEQ ID NO 16
<211> LENGTH: 708
<212> TYPE: DNA
<213> ORGANISM: Artificial Sequence
<220> FEATURE:
<223> OTHER INFORMATION: Synthetic

<400> SEQUENCE: 16
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccacct tcggctacgg cctgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacacccc catcggcgac ggccccgtgc tgctgcccga caaccactac     600
ctgagctacc agtccgccct gagcaaagac cccaacgaga agcgcgatca catggtcctg     660
ctggagttcg tgaccgccgc cgggatcact ctcggcatgg acgagctg               708

<210> SEQ ID NO 17
<211> LENGTH: 77
<212> TYPE: RNA
```

```
<213> ORGANISM: Artificial Sequence
<220> FEATURE:
<223> OTHER INFORMATION: Synthetic

<400> SEQUENCE: 17
guuuuagagc uagaaauagc aaguuaaaau aaggcuaguc cguuaucaac uugaaaaagu      60
ggcaccgagu cggugcu                                                    77

<210> SEQ ID NO 18
<211> LENGTH: 82
<212> TYPE: RNA
<213> ORGANISM: Artificial Sequence
<220> FEATURE:
<223> OTHER INFORMATION: Synthetic

<400> SEQUENCE: 18
guuggaacca uucaaaacag cauagcaagu uaaaauaagg cuagccguu aucaacuuga      60 aaaaguggca ccgagucggu gc                                              82

<210> SEQ ID NO 19
<211> LENGTH: 76
<212> TYPE: RNA
<213> ORGANISM: Artificial Sequence
<220> FEATURE:
<223> OTHER INFORMATION: Synthetic

<400> SEQUENCE: 19
guuuuagagc uagaaauagc aaguuaaaau aaggcuaguc cguuaucaac uugaaaaagu      60
ggcaccgagu cggugc                                                     76

<210> SEQ ID NO 20
<211> LENGTH: 86
<212> TYPE: RNA
<213> ORGANISM: Artificial Sequence
<220> FEATURE:
<223> OTHER INFORMATION: Synthetic

<400> SEQUENCE: 20
guuuaagagc uaugcuggaa acagcauagc aaguuuaaau aaggcuaguc cguuaucaac      60
uugaaaaagu ggcaccgagu cggugc                                          86

<210> SEQ ID NO 21
<211> LENGTH: 1392
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1384)
<223> OTHER INFORMATION: Cas9
<220> FEATURE:
<221> NAME/KEY: MISC_FEATURE
<222> LOCATION: (1385)..(1392)
<223> OTHER INFORMATION: FLAG

<400> SEQUENCE: 21

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45
```

Gly Ala Leu Leu Phe Asp Ser Gly Glu Thr Ala Glu Ala Thr Arg Leu
      50                  55                  60

Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                     85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu

-continued

```
            465                 470                 475                 480
Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895
```

```
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
            1010                1015                1020
Lys Ser Glu Gln Glu Ile Gly Lys Ala Thr Ala Lys Tyr Phe Phe
            1025                1030                1035
Tyr Ser Asn Ile Met Asn Phe Phe Lys Thr Glu Ile Thr Leu Ala
            1040                1045                1050
Asn Gly Glu Ile Arg Lys Arg Pro Leu Ile Glu Thr Asn Gly Glu
            1055                1060                1065
Thr Gly Glu Ile Val Trp Asp Lys Gly Arg Asp Phe Ala Thr Val
            1070                1075                1080
Arg Lys Val Leu Ser Met Pro Gln Val Asn Ile Val Lys Lys Thr
            1085                1090                1095
Glu Val Gln Thr Gly Gly Phe Ser Lys Glu Ser Ile Leu Pro Lys
            1100                1105                1110
Arg Asn Ser Asp Lys Leu Ile Ala Arg Lys Lys Asp Trp Asp Pro
            1115                1120                1125
Lys Lys Tyr Gly Gly Phe Asp Ser Pro Thr Val Ala Tyr Ser Val
            1130                1135                1140
Leu Val Val Ala Lys Val Glu Lys Gly Lys Ser Lys Lys Leu Lys
            1145                1150                1155
Ser Val Lys Glu Leu Leu Gly Ile Thr Ile Met Glu Arg Ser Ser
            1160                1165                1170
Phe Glu Lys Asn Pro Ile Asp Phe Leu Glu Ala Lys Gly Tyr Lys
            1175                1180                1185
Glu Val Lys Lys Asp Leu Ile Ile Lys Leu Pro Lys Tyr Ser Leu
            1190                1195                1200
Phe Glu Leu Glu Asn Gly Arg Lys Arg Met Leu Ala Ser Ala Gly
            1205                1210                1215
Glu Leu Gln Lys Gly Asn Glu Leu Ala Leu Pro Ser Lys Tyr Val
            1220                1225                1230
Asn Phe Leu Tyr Leu Ala Ser His Tyr Glu Lys Leu Lys Gly Ser
            1235                1240                1245
Pro Glu Asp Asn Glu Gln Lys Gln Leu Phe Val Glu Gln His Lys
            1250                1255                1260
His Tyr Leu Asp Glu Ile Ile Glu Gln Ile Ser Glu Phe Ser Lys
            1265                1270                1275
Arg Val Ile Leu Ala Asp Ala Asn Leu Asp Lys Val Leu Ser Ala
            1280                1285                1290
```

```
Tyr Asn Lys His Arg Asp Lys Pro Ile Arg Glu Gln Ala Glu Asn
    1295            1300                1305
Ile Ile His Leu Phe Thr Leu Thr Asn Leu Gly Ala Pro Ala Ala
1310                1315                1320
Phe Lys Tyr Phe Asp Thr Thr Ile Asp Arg Lys Arg Tyr Thr Ser
    1325            1330                1335
Thr Lys Glu Val Leu Asp Ala Thr Leu Ile His Gln Ser Ile Thr
1340                1345                1350
Gly Leu Tyr Glu Thr Arg Ile Asp Leu Ser Gln Leu Gly Gly Asp
    1355            1360                1365
Lys Arg Pro Ala Ala Thr Lys Lys Ala Gly Gln Ala Lys Lys Lys
1370                1375                1380
Lys Asp Tyr Lys Asp Asp Asp Lys
    1385            1390

<210> SEQ ID NO 22
<211> LENGTH: 4176
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4152)
<223> OTHER INFORMATION: Cas9
<220> FEATURE:
<221> NAME/KEY: misc_feature
<222> LOCATION: (4153)..(4176)
<223> OTHER INFORMATION: FLAG

<400> SEQUENCE: 22
atggacaaga agtacagcat cggcctggac atcggcacca actctgtggg ctgggccgtg      60
atcaccgacg agtacaaggt gcccagcaag aaattcaagg tgctgggcaa caccgaccgg     120
cacagcatca agaagaacct gatcggagcc ctgctgttcg acagcggcga aacagccgag     180
gccacccggc tgaagagaac cgccagaaga agatacacca gacggaagaa ccggatctgc     240
tatctgcaag agatcttcag caacgagatg gccaaggtgg acgacagctt cttccacaga     300
ctggaagagt ccttcctggt ggaagaggat aagaagcacg agcggcaccc catcttcggc     360
aacatcgtgg acgaggtggc ctaccacgag aagtacccca ccatctacca cctgagaaag     420
aaactggtgg acagcaccga caaggccgac ctgcggctga tctatctggc cctgccccac     480
atgatcaagt ccggggccca cttcctgatc gagggcgacc tgaaccccga caacagcgac     540
gtggacaagc tgttcatcca gctggtgcag acctacaacc agctgttcga ggaaaacccc     600
atcaacgcca gcggcgtgga cgccaaggcc atcctgtctg ccagactgag caagagcaga     660
cggctggaaa atctgatcgc ccagctgccc ggcgagaaga gaatggcct gttcggaaac     720 ctgattgccc tgagcctggg cctgaccccc aacttcaaga gcaacttcga cctggccgag     780
gatgccaaac tgcagctgag caaggacacc tacgacgacg acctggacaa cctgctggcc     840
cagatcggcg accagtacgc cgacctgttt ctggccgcca gaacctgtc cgacgccatc     900 ctgctgagcg acatcctgag agtgaacacc gagatcacca aggccccct gagcgcctct     960 atgatcaaga gatacgacga gcaccaccag gacctgaccc tgctgaaagc tctcgtgcgc    1020
cagcagctgc ctgagaagta caaagagatt ttcttcgacc agagcaagaa cggctacgcc    1080
ggctacattg acggcggagc cagccaggaa gagttctaca agttcatcaa gcccatcctg    1140
gaaaagatgg acggcaccga ggaactgctc gtgaagctga acagagagga cctgctgcgg    1200
```

```
aagcagcgga ccttcgacaa cggcagcatc ccccaccaga tccacctggg agagctgcac    1260
gccattctgc ggcggcagga agattttttac ccattcctga aggacaaccg ggaaaagatc    1320
gagaagatcc tgaccttccg catcccctac tacgtgggcc tctggccag  ggaaacagc     1380 agattcgcct ggatgaccag aaagagcgag gaaaccatca ccccctggaa cttcgaggaa    1440
gtggtggaca agggcgcttc cgcccagagc ttcatcgagc ggatgaccaa cttcgataag    1500
aacctgccca cgagaaggt gctgcccaag cacagcctgc tgtacgagta cttcaccgtg     1560
tataacgagc tgaccaaagt gaaatacgtg accgagggaa tgagaaagcc cgccttcctg    1620
agcggcgagc agaaaaaggc catcgtggac ctgctgttca agaccaaccg gaaagtgacc    1680
gtgaagcagc tgaaagagga ctacttcaag aaaatcgagt gcttcgactc cgtggaaatc    1740
tccggcgtgg aagatcggtt caacgcctcc ctgggcacat accacgatct gctgaaaatt    1800
atcaaggaca aggacttcct ggacaatgag gaaaacgagg acattctgga agatatcgtg    1860
ctgaccctga cactgtttga ggacagagag atgatcgagg aacggctgaa aacctatgcc    1920
cacctgttcg acgacaaagt gatgaagcag ctgaagcggc ggagatacac cggctggggc    1980
aggctgagcc ggaagctgat caacggcatc cgggacaagc agtccggcaa gacaatcctg    2040
gatttcctga agtccgacgg cttcgccaac agaaacttca tgcagctgat ccacgacgac    2100
agcctgacct ttaaagagga catccagaaa gcccaggtgt ccggccaggg cgatagcctg    2160
cacgagcaca ttgccaatct ggccggcagc cccgccatta gaagggcat  cctgcagaca    2220 gtgaaggtgg tggacgagct cgtgaaagtg atgggccggc acaagcccga acatcgtg     2280 atcgaaatgg ccagagagaa ccagaccacc cagaagggac agaagaacag ccgcgagaga    2340
atgaagcgga tcgaagaggg catcaaagag ctgggcagcc agatcctgaa agaacacccc    2400
gtggaaaaca cccagctgca gaacgagaag ctgtacctgt actacctgca gaatgggcgg    2460
gatatgtacg tggaccagga actggacatc aaccggctgt ccgactacga tgtggaccat    2520
atcgtgcctc agagctttct gaaggacgac tccatcgaca caaggtgct  gaccagaagc    2580 gacaagaacc ggggcaagag cgacaacgtg ccctccgaag aggtcgtgaa aagatgaag     2640 aactactggc ggcagctgct gaacgccaag ctgattaccc agagaaagtt cgacaatctg    2700
accaaggccg agagaggcgg cctgagcgaa ctggataagg ccggcttcat caagagacag    2760
ctggtggaaa cccggcagat cacaaagcac gtggcacaga tcctggactc ccggatgaac    2820
actaagtacg acgagaatga caagctgatc cgggaagtga aagtgatcac cctgaagtcc    2880
aagctggtgt ccgatttccg gaaggatttc cagttttaca agtgcgcga  gatcaacaac    2940 taccaccacg cccacgacgc ctacctgaac gccgtcgtgg aaccgcccct gatcaaaaag    3000
taccctaagc tggaaagcga gttcgtgtac ggcgactaca aggtgtacga cgtgcggaag    3060
atgatcgcca agagcgagca ggaaatcggc aaggctaccg ccaagtactt cttctacagc    3120
aacatcatga cttttttcaa gaccgagatt accctggcca acggcgagat ccggaagcgg    3180
cctctgatcg agacaaacgg cgaaaccggg gagatcgtgt gggataaggg ccggattttt    3240
gccaccgtgc ggaaagtgct gagcatgccc caagtgaata tcgtgaaaaa gaccgaggtg    3300
cagacaggcg gcttcagcaa agagtctatc ctgcccaaga ggaacagcga taagctgatc    3360
gccagaaaga aggactggga ccctaagaag tacgcggct  tcgacagccc caccgtggcc    3420
tattctgtgc tggtggtggc caaagtggaa aagggcaagt ccaagaaact gaagagtgtg    3480
aaagagctac tggggatcac catcatggaa agaagcagct cgagaagaa  tcccatcgac    3540 tttctggaag ccaagggcta caaagaagtg aaaaaggacc tgatcatcaa gctgcctaag    3600
```

```
tactccctgt tcgagctgga aaacggccgg aagagaatgc tggcctctgc cggcgaactg      3660
cagaagggaa acgaactggc cctgccctcc aaatatgtga acttcctgta cctggccagc      3720
cactatgaga agctgaaggg ctccccgag gataatgagc agaaacagct gtttgtggaa       3780
cagcacaagc actacctgga cgagatcatc gagcagatca gcgagttctc caagagagtg      3840
atcctggccg acgctaatct ggacaaagtg ctgtccgcct acaacaagca ccgggataag      3900
cccatcagag agcaggccga gaatatcatc cacctgttta ccctgaccaa tctgggagcc      3960
cctgccgcct tcaagtactt tgacaccacc atcgaccgga gaggtacac cagcaccaaa       4020 gaggtgctgg acgccaccct gatccaccag agcatcaccg gcctgtacga gacacggatc      4080
gacctgtctc agctgggagg cgacaagcga cctgccgcca caagaaggc tggacaggct       4140 aagaagaaga aagattacaa agacgatgac gataag                                4176
```

```
<210> SEQ ID NO 23
<211> LENGTH: 16
<212> TYPE: RNA
<213> ORGANISM: Artificial Sequence
<220> FEATURE:
<223> OTHER INFORMATION: Synthetic

<400> SEQUENCE: 23
guuuuagagc uaugcu                                                      16

<210> SEQ ID NO 24
<211> LENGTH: 67
<212> TYPE: RNA
<213> ORGANISM: Artificial Sequence
<220> FEATURE:
<223> OTHER INFORMATION: Synthetic

<400> SEQUENCE: 24
agcauagcaa guuaaaauaa ggcuaguccg uuaucaacuu gaaaaagugg caccgagucg      60
gugcuuu                                                                67

<210> SEQ ID NO 25
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n = A, T, C, or G

<400> SEQUENCE: 25
gnnnnnnnnn nnnnnnnnnn ngg                                              23

<210> SEQ ID NO 26
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n = A, T, C, or G

<400> SEQUENCE: 26
nnnnnnnnnn nnnnnnnnnn ngg                                              23
```

<210> SEQ ID NO 27
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n = A, T, C, or G

<400> SEQUENCE: 27
ggnnnnnnnn nnnnnnnnnn nnngg                                              25

<210> SEQ ID NO 28
<211> LENGTH: 72
<212> TYPE: RNA
<213> ORGANISM: Artificial Sequence
<220> FEATURE:
<223> OTHER INFORMATION: Synthetic

<400> SEQUENCE: 28
aaacagcaua gcaaguuaaa auaaggcuag uccguuauca acuugaaaaa guggcaccga         60
gucggugcuu uu                                                            72

<210> SEQ ID NO 29
<211> LENGTH: 82
<212> TYPE: RNA
<213> ORGANISM: Artificial Sequence
<220> FEATURE:
<223> OTHER INFORMATION: Synthetic

<400> SEQUENCE: 29
guuggaacca uucaaaacag cauagcaagu uaaaauaagg cuaguccguu aucaacuuga         60
aaaaguggca ccgagucggu gc                                                 82

<210> SEQ ID NO 30
<211> LENGTH: 83
<212> TYPE: RNA
<213> ORGANISM: Artificial Sequence
<220> FEATURE:
<223> OTHER INFORMATION: Synthetic

<400> SEQUENCE: 30
guuuuagagc uagaaauagc aaguuaaaau aaggcuaguc cguuaucaac uugaaaagu          60 ggcaccgagu cggugcuuuu uuu                                                83

<210> SEQ ID NO 31
<211> LENGTH: 80
<212> TYPE: RNA
<213> ORGANISM: Artificial Sequence
<220> FEATURE:
<223> OTHER INFORMATION: Synthetic

<400> SEQUENCE: 31
guuuuagagc uagaaauagc aaguuaaaau aaggcuaguc cguuaucaac uugaaaagu          60 ggcaccgagu cggugcuuuu                                                    80

<210> SEQ ID NO 32
<211> LENGTH: 92
<212> TYPE: RNA
<213> ORGANISM: Artificial Sequence
<220> FEATURE:
<223> OTHER INFORMATION: Synthetic

<400> SEQUENCE: 32
guuuaagagc uaugcuggaa acagcauagc aaguuaaaau aaggcuaguc cguuaucaac        60
uugaaaaagu ggcaccgagu cggugcuuuu uu                                     92

<210> SEQ ID NO 33
<211> LENGTH: 34
<212> TYPE: RNA
<213> ORGANISM: Artificial Sequence
<220> FEATURE:
<223> OTHER INFORMATION: Synthetic

<400> SEQUENCE: 33
ggccaacaug aggaucaccc augucugcag ggcc                                   34

<210> SEQ ID NO 34
<211> LENGTH: 137
<212> TYPE: RNA
<213> ORGANISM: Artificial Sequence
<220> FEATURE:
<223> OTHER INFORMATION: Synthetic

<400> SEQUENCE: 34
guuuuagagc uaggccaaca ugaggaucac ccaugucugc agggccuagc aaguuaaaau        60
aaggcuaguc cguuaucaac uuggccaaca ugaggaucac ccaugucugc agggccaagu       120
ggcaccgagu cggugcu                                                     137

<210> SEQ ID NO 35
<211> LENGTH: 157
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 35
nnnnnnnnnn nnnnnnnnnn guuuuagagc uaggccaaca ugaggaucac ccaugucugc        60
agggccuagc aaguuaaaau aaggcuaguc cguuaucaac uuggccaaca ugaggaucac       120
ccaugucugc agggccaagu ggcaccgagu cggugcu                               157

<210> SEQ ID NO 36
<211> LENGTH: 1471
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1384)
<223> OTHER INFORMATION: dCas9
<220> FEATURE:
<221> NAME/KEY: MISC_FEATURE
<222> LOCATION: (1405)..(1409)
<223> OTHER INFORMATION: NLS
<220> FEATURE:
<221> NAME/KEY: MISC_FEATURE
<222> LOCATION: (1410)..(1471)
<223> OTHER INFORMATION: VP64

<400> SEQUENCE: 36

Met Lys Arg Pro Ala Ala Thr Lys Lys Ala Gly Gln Ala Lys Lys Lys
1               5                   10                  15

```
Lys Asp Lys Lys Tyr Ser Ile Gly Leu Ala Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
        210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
            245                 250                 255

Leu Ile Ala Leu Ser Leu Gly Leu Thr Pro Asn Phe Lys Ser Asn Phe
        260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
        290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
        370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430
```

Gly Glu Leu His Ala Ile Leu Arg Arg Gln Asp Phe Tyr Pro Phe
            435                 440                 445

Leu Lys Asp Asn Arg Glu Lys Ile Glu Lys Ile Leu Thr Phe Arg Ile
450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
            485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
            515                 520                 525

Leu Leu Tyr Glu Tyr Phe Thr Val Tyr Asn Glu Leu Thr Lys Val Lys
            530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
            565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
            595                 600                 605

Thr Tyr His Asp Leu Leu Lys Ile Ile Lys Asp Lys Asp Phe Leu Asp
            610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
            645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
            675                 680                 685

Lys Gln Ser Gly Lys Thr Ile Leu Asp Phe Leu Lys Ser Asp Gly Phe
            690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
            725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
            755                 760                 765

Arg His Lys Pro Glu Asn Ile Val Ile Glu Met Ala Arg Glu Asn Gln
770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
            805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
            835                 840                 845

Leu Ser Asp Tyr Asp Val Asp His Ile Val Pro Gln Ser Phe Leu Lys

```
                850             855             860
Asp Asp Ser Ile Asp Asn Lys Val Leu Thr Arg Ser Asp Lys Ala Arg
865                 870             875                 880

Gly Lys Ser Asp Asn Val Pro Ser Glu Glu Val Val Lys Lys Met Lys
                885             890                 895

Asn Tyr Trp Arg Gln Leu Leu Asn Ala Lys Leu Ile Thr Gln Arg Lys
            900             905             910

Phe Asp Asn Leu Thr Lys Ala Glu Arg Gly Gly Leu Ser Glu Leu Asp
        915             920             925

Lys Ala Gly Phe Ile Lys Arg Gln Leu Val Glu Thr Arg Gln Ile Thr
    930             935             940

Lys His Val Ala Gln Ile Leu Asp Ser Arg Met Asn Thr Lys Tyr Asp
945             950             955             960

Glu Asn Asp Lys Leu Ile Arg Glu Val Lys Val Ile Thr Leu Lys Ser
            965             970             975

Lys Leu Val Ser Asp Phe Arg Lys Asp Phe Gln Phe Tyr Lys Val Arg
        980             985             990

Glu Ile Asn Asn Tyr His His Ala His Asp Ala Tyr Leu Asn Ala Val
        995             1000            1005

Val Gly Thr Ala Leu Ile Lys Lys Tyr Pro Lys Leu Glu Ser Glu
    1010            1015            1020

Phe Val Tyr Gly Asp Tyr Lys Val Tyr Asp Val Arg Lys Met Ile
    1025            1030            1035

Ala Lys Ser Glu Gln Glu Ile Gly Lys Ala Thr Ala Lys Tyr Phe
    1040            1045            1050

Phe Tyr Ser Asn Ile Met Asn Phe Phe Lys Thr Glu Ile Thr Leu
    1055            1060            1065

Ala Asn Gly Glu Ile Arg Lys Arg Pro Leu Ile Glu Thr Asn Gly
    1070            1075            1080

Glu Thr Gly Glu Ile Val Trp Asp Lys Gly Arg Asp Phe Ala Thr
    1085            1090            1095

Val Arg Lys Val Leu Ser Met Pro Gln Val Asn Ile Val Lys Lys
    1100            1105            1110

Thr Glu Val Gln Thr Gly Gly Phe Ser Lys Glu Ser Ile Leu Pro
    1115            1120            1125

Lys Arg Asn Ser Asp Lys Leu Ile Ala Arg Lys Lys Asp Trp Asp
    1130            1135            1140

Pro Lys Lys Tyr Gly Gly Phe Asp Ser Pro Thr Val Ala Tyr Ser
    1145            1150            1155

Val Leu Val Val Ala Lys Val Glu Lys Gly Lys Ser Lys Lys Leu
    1160            1165            1170

Lys Ser Val Lys Glu Leu Leu Gly Ile Thr Ile Met Glu Arg Ser
    1175            1180            1185

Ser Phe Glu Lys Asn Pro Ile Asp Phe Leu Glu Ala Lys Gly Tyr
    1190            1195            1200

Lys Glu Val Lys Lys Asp Leu Ile Ile Lys Leu Pro Lys Tyr Ser
    1205            1210            1215

Leu Phe Glu Leu Glu Asn Gly Arg Lys Arg Met Leu Ala Ser Ala
    1220            1225            1230

Gly Glu Leu Gln Lys Gly Asn Glu Leu Ala Leu Pro Ser Lys Tyr
    1235            1240            1245

Val Asn Phe Leu Tyr Leu Ala Ser His Tyr Glu Lys Leu Lys Gly
    1250            1255            1260
```

-continued

Ser Pro Glu Asp Asn Glu Gln Lys Gln Leu Phe Val Glu Gln His
    1265                1270                1275

Lys His Tyr Leu Asp Glu Ile Ile Glu Gln Ile Ser Glu Phe Ser
    1280                1285                1290

Lys Arg Val Ile Leu Ala Asp Ala Asn Leu Asp Lys Val Leu Ser
    1295                1300                1305

Ala Tyr Asn Lys His Arg Asp Lys Pro Ile Arg Glu Gln Ala Glu
    1310                1315                1320

Asn Ile Ile His Leu Phe Thr Leu Thr Asn Leu Gly Ala Pro Ala
    1325                1330                1335

Ala Phe Lys Tyr Phe Asp Thr Thr Ile Asp Arg Lys Arg Tyr Thr
    1340                1345                1350

Ser Thr Lys Glu Val Leu Asp Ala Thr Leu Ile His Gln Ser Ile
    1355                1360                1365

Thr Gly Leu Tyr Glu Thr Arg Ile Asp Leu Ser Gln Leu Gly Gly
    1370                1375                1380

Asp Ser Ala Gly Gly Gly Ser Gly Gly Gly Ser Gly Gly
    1385                1390                1395

Gly Gly Ser Gly Pro Lys Lys Lys Arg Lys Val Ala Ala Ala Gly
    1400                1405                1410

Ser Gly Arg Ala Asp Ala Leu Asp Asp Phe Asp Leu Asp Met Leu
    1415                1420                1425

Gly Ser Asp Ala Leu Asp Asp Phe Asp Leu Asp Met Leu Gly Ser
    1430                1435                1440

Asp Ala Leu Asp Asp Phe Asp Leu Asp Met Leu Gly Ser Asp Ala
    1445                1450                1455

Leu Asp Asp Phe Asp Leu Asp Met Leu Ile Asn Cys Thr
    1460                1465                1470

<210> SEQ ID NO 37
<211> LENGTH: 473
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(130)
<223> OTHER INFORMATION: MCP
<220> FEATURE:
<221> NAME/KEY: MISC_FEATURE
<222> LOCATION: (151)..(155)
<223> OTHER INFORMATION: NLS
<220> FEATURE:
<221> NAME/KEY: MISC_FEATURE
<222> LOCATION: (161)..(341)
<223> OTHER INFORMATION: P65
<220> FEATURE:
<221> NAME/KEY: MISC_FEATURE
<222> LOCATION: (350)..(473)
<223> OTHER INFORMATION: HSF1

<400> SEQUENCE: 37

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Lys Arg Lys Tyr Thr Ile Lys Val Glu

```
              50                  55                  60
Val Pro Lys Val Ala Thr Gln Thr Val Gly Gly Val Glu Leu Pro Val
 65                  70                  75                  80

Ala Ala Trp Arg Ser Tyr Leu Asn Met Glu Leu Thr Ile Pro Ile Phe
                     85                  90                  95

Ala Thr Asn Ser Asp Cys Glu Leu Ile Val Lys Ala Met Gln Gly Leu
                100                 105                 110

Leu Lys Asp Gly Asn Pro Ile Pro Ser Ala Ile Ala Ala Asn Ser Gly
                115                 120                 125

Ile Tyr Ser Ala Gly Gly Gly Ser Gly Gly Gly Ser Gly Gly
                130                 135                 140

Gly Gly Ser Gly Pro Lys Lys Lys Arg Lys Val Ala Ala Ala Gly Ser
145                 150                 155                 160

Pro Ser Gly Gln Ile Ser Asn Gln Ala Leu Ala Leu Ala Pro Ser Ser
                165                 170                 175

Ala Pro Val Leu Ala Gln Thr Met Val Pro Ser Ser Ala Met Val Pro
                180                 185                 190

Leu Ala Gln Pro Pro Ala Pro Ala Pro Val Leu Thr Pro Gly Pro Pro
                195                 200                 205

Gln Ser Leu Ser Ala Pro Val Pro Lys Ser Thr Gln Ala Gly Glu Gly
                210                 215                 220

Thr Leu Ser Glu Ala Leu Leu His Leu Gln Phe Asp Ala Asp Glu Asp
225                 230                 235                 240

Leu Gly Ala Leu Leu Gly Asn Ser Thr Asp Pro Gly Val Phe Thr Asp
                245                 250                 255

Leu Ala Ser Val Asp Asn Ser Glu Phe Gln Gln Leu Leu Asn Gln Gly
                260                 265                 270

Val Ser Met Ser His Ser Thr Ala Glu Pro Met Leu Met Glu Tyr Pro
                275                 280                 285

Glu Ala Ile Thr Arg Leu Val Thr Gly Ser Gln Arg Pro Pro Asp Pro
                290                 295                 300

Ala Pro Thr Pro Leu Gly Thr Ser Gly Leu Pro Asn Gly Leu Ser Gly
305                 310                 315                 320

Asp Glu Asp Phe Ser Ser Ile Ala Asp Met Asp Phe Ser Ala Leu Leu
                325                 330                 335

Ser Gln Ile Ser Ser Ser Gly Gln Gly Gly Gly Ser Gly Phe Ser
                340                 345                 350

Val Asp Thr Ser Ala Leu Leu Asp Leu Phe Ser Pro Ser Val Thr Val
                355                 360                 365

Pro Asp Met Ser Leu Pro Asp Leu Asp Ser Ser Leu Ala Ser Ile Gln
                370                 375                 380

Glu Leu Leu Ser Pro Gln Glu Pro Pro Arg Pro Pro Glu Ala Glu Asn
385                 390                 395                 400

Ser Ser Pro Asp Ser Gly Lys Gln Leu Val His Tyr Thr Ala Gln Pro
                405                 410                 415

Leu Phe Leu Leu Asp Pro Gly Ser Val Asp Thr Gly Ser Asn Asp Leu
                420                 425                 430

Pro Val Leu Phe Glu Leu Gly Glu Gly Ser Tyr Phe Ser Glu Gly Asp
                435                 440                 445

Gly Phe Ala Glu Asp Pro Thr Ile Ser Leu Leu Thr Gly Ser Glu Pro
450                 455                 460

Pro Lys Ala Lys Asp Pro Thr Val Ser
465                 470
```

<210> SEQ ID NO 38
<211> LENGTH: 4413
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4152)
<223> OTHER INFORMATION: dCas9
<220> FEATURE:
<221> NAME/KEY: misc_feature
<222> LOCATION: (4213)..(4227)
<223> OTHER INFORMATION: NLS
<220> FEATURE:
<221> NAME/KEY: misc_feature
<222> LOCATION: (4228)..(4413)
<223> OTHER INFORMATION: VP64

<400> SEQUENCE: 38

```
atgaaaaggc cggcggccac gaaaaaggcc ggccaggcaa aaagaaaaa ggacaagaag      60
tacagcatcg gcctggccat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct ccacagact  ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca ggcccgacct gcggctgatc tatctggccc tggcccacat gatcaagttc    540
cggggccact tcctgatcga gggcgacctg aaccccgaca cagcgacgt  ggacaagctg    600
ttcatccagc tggtgcagac ctacaaccag ctgttcgagg aaaacccat  caacgccagc    660
ggcgtggacg ccaaggccat cctgtctgcc agactgagca gagcagacg  gctggaaaat    720
ctgatcgccc agctgcccgg cgagaagaag aatggcctgt cggcaacct  gattgccctg    780
agcctgggcc tgacccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gcccccctga gcgcctctat gatcaagaga   1020
tacgacgagc accaccagga cctgaccctg ctgaaagctc tcgtgcggca gcagctgcct   1080
gagaagtaca aagagatttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag atttttaccc attcctgaag gacaaccggg aaaagatcga agatcctg    1380
accttccgca tcccctacta cgtgggccct ctggccaggg gaaacagcag attcgcctgg   1440
atgaccagaa agagcgagga aaccatcacc cctggaactt cgaggaagt  ggtggacaag   1500
ggcgcttccg cccagagctt catcgagcgg atgaccaact tcgataagaa cctgcccaac   1560
gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
```

| | |
|---|---|
| aaaaaggcca tcgtggacct gctgttcaag accaaccgga aagtgaccgt gaagcagctg | 1740 |
| aaagaggact acttcaagaa aatcgagtgc ttcgactccg tggaaatctc cggcgtggaa | 1800 |
| gatcggttca acgcctccct gggcacatac cacgatctgc tgaaaattat caaggacaag | 1860 |
| gacttcctgg acaatgagga aaacgaggac attctggaag atatcgtgct gaccctgaca | 1920 |
| ctgtttgagg acagagagat gatcgaggaa cggctgaaaa cctatgccca cctgttcgac | 1980 |
| gacaaagtga tgaagcagct gaagcggcgg agatacaccg ctggggcag gctgagccgg | 2040 |
| aagctgatca acggcatccg ggacaagcag tccggcaaga caatcctgga tttcctgaag | 2100 |
| tccgacggct cgccaacag aaacttcatg cagctgatcc acgacgacag cctgaccttt | 2160 |
| aaagaggaca tccagaaagc ccaggtgtcc ggccagggcg atagcctgca cgagcacatt | 2220 |
| gccaatctgg ccggcagccc cgccattaag aagggcatcc tgcagacagt gaaggtggtg | 2280 |
| gacgagctcg tgaaagtgat gggccggcac aagcccgaga acatcgtgat cgaaatggcc | 2340 |
| agagagaacc agaccaccca gaagggacag aagaacagcc gcgagagaat gaagcggatc | 2400 |
| gaagagggca tcaaagagct gggcagccag atcctgaaag aacaccccgt ggaaaacacc | 2460 |
| cagctgcaga acgagaagct gtacctgtac tacctgcaga atgggcggga tatgtacgtg | 2520 |
| gaccaggaac tggacatcaa ccggctgtcc gactacgatg tggaccacat cgtgcctcag | 2580 |
| agctttctga aggacgactc catcgacaac aaggtgctga ccagaagcga caaggcccgg | 2640 |
| ggcaagagcg acaacgtgcc ctccgaagag gtcgtgaaga gatgaagaa ctactggcgg | 2700 |
| cagctgctga acgccaagct gattacccag agaaagttcg acaatctgac caaggccgag | 2760 |
| agaggcggcc tgagcgaact ggataaggcc ggcttcatca agacagct ggtggaaacc | 2820 |
| cggcagatca caaagcacgt ggcacagatc ctggactccc ggatgaacac taagtacgac | 2880 |
| gagaatgaca agctgatccg ggaagtgaaa gtgatcaccc tgaagtccaa gctggtgtcc | 2940 |
| gatttccgga aggatttcca gttttacaaa gtgcgcgaga tcaacaacta ccaccacgcc | 3000 |
| cacgacgcct acctgaacgc cgtcgtggga accgccctga tcaaaagta ccctaagctg | 3060 |
| gaaagcgagt tcgtgtacgg cgactacaag gtgtacgacg tgcggaagat gatcgccaag | 3120 |
| agcgagcagg aaatcggcaa ggctaccgcc aagtacttct tctacagcaa catcatgaac | 3180 |
| ttttttcaaga ccgagattac cctggccaac ggcgagatcc ggaagcggcc tctgatcgag | 3240 |
| acaaacggcg aaaccgggga gatcgtgtgg gataagggcc gggattttgc caccgtgcgg | 3300 |
| aaagtgctga gcatgcccca gtgaatatc gtgaaaaaga ccgaggtgca gacaggcggc | 3360 |
| ttcagcaaag agtctatcct gcccaagagg aacagcgata gctgatcgc cagaaagaag | 3420 |
| gactgggacc ctaagaagta cggcggcttc gacagcccca ccgtggccta ttctgtgctg | 3480 |
| gtggtggcca agtggaaaa gggcaagtcc aagaaactga agagtgtgaa agagctgctg | 3540 |
| gggatcacca tcatggaaag aagcagcttc gagaagaatc ccatcgactt tctggaagcc | 3600 |
| aagggctaca aagaagtgaa aaaggacctg atcatcaagc tgcctaagta ctccctgttc | 3660 |
| gagctggaaa acggccggaa gagaatgctg gcctctgccg gcgaactgca gaagggaaac | 3720 |
| gaactggccc tgccctccaa atatgtgaac ttcctgtacc tggccagcca ctatgagaag | 3780 |
| ctgaagggct ccccccgagga taatgagcag aaacagctgt tgtggaaca gcacaagcac | 3840 |
| tacctggacg agatcatcga gcagatcagc gagttctcca agagagtgat cctggccgac | 3900 |
| gctaatctgg acaaagtgct gtccgcctac aacaagcacc gggataagcc catcagagag | 3960 |
| caggccgaga atatcatcca cctgtttacc ctgaccaatc tgggagcccc tgccgccttc | 4020 |
| aagtactttg acaccaccat cgaccggaag aggtacacca gcaccaaaga ggtgctggac | 4080 |

```
gccaccctga tccaccagag catcaccggc ctgtacgaga cacggatcga cctgtctcag   4140
ctgggaggcg acagcgctgg aggaggtgga agcggaggag gaggaagcgg aggaggaggt   4200
agcggaccta agaaaaagag gaaggtggcg gccgctggat ccggacgggc tgacgcattg   4260
gacgattttg atctggatat gctgggaagt gacgccctcg atgattttga ccttgacatg   4320
cttggttcgg atgcccttga tgactttgac ctcgacatgc tcggcagtga cgcccttgat   4380
gatttcgacc tggacatgct gattaactgt aca                                4413

<210> SEQ ID NO 39
<211> LENGTH: 1419
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(390)
<223> OTHER INFORMATION: MCP
<220> FEATURE:
<221> NAME/KEY: misc_feature
<222> LOCATION: (451)..(465)
<223> OTHER INFORMATION: NLS
<220> FEATURE:
<221> NAME/KEY: misc_feature
<222> LOCATION: (481)..(1023)
<223> OTHER INFORMATION: P65
<220> FEATURE:
<221> NAME/KEY: misc_feature
<222> LOCATION: (1048)..(1419)
<223> OTHER INFORMATION: HSF1

<400> SEQUENCE: 39
atggcttcaa actttactca gttcgtgctc gtggacaatg gtgggacagg ggatgtgaca     60
gtggctcctt ctaatttcgc taatggggtg gcagagtgga tcagctccaa ctcacggagc    120
caggcctaca aggtgacatg cagcgtcagg cagtctagtg cccagaagag aaagtatacc    180
atcaaggtgg aggtccccaa agtggctacc agacagtgg gcggagtcga actgcctgtc    240
gccgcttgga ggtcctacct gaacatggag ctcactatcc caattttcgc taccaattct    300
gactgtgaac tcatcgtgaa ggcaatgcag gggctcctca aagacggtaa tcctatccct    360
tccgccatcg ccgctaactc aggtatctac agcgctggag gaggtggaag cggaggagga    420
ggaagcggag gaggaggtag cggacctaag aaaaagagga aggtggcggc cgctggatcc    480
ccttcagggc agatcagcaa ccaggccctg gctctggccc ctagctccgc tccagtgctg    540
gcccagacta tggtgccctc tagtgctatg gtgcctctgg cccagccacc tgctccagcc    600
cctgtgctga ccccaggacc accccagtca ctgagcgctc cagtgcccaa gtctacacag    660
gccggcgagg ggactctgag tgaagctctg ctgcacctgc agttcgacgc tgatgaggac    720 ctggagctc tgctggggaa cagcaccgat cccggagtgt tcacagatct ggcctccgtg    780
gacaactctg agtttcagca gctgctgaat caggcgtgt ccatgtctca gtacagcc      840 gaaccaatgc tgatggagta ccccgaagcc attacccggc tggtgaccgg cagccagcgg    900
ccccccgacc ccgctccaac tccccttggga accagcggcc tgcctaatgg gctgtccgga    960
gatgaagact tctcaagcat cgctgatatg gactttagtg ccctgctgtc acagatttcc   1020
tctagtgggc agggaggagg tggaagcggc ttcagcgtgg acaccagtgc cctgctggac   1080
ctgttcagcc cctcggtgac cgtgcccgac atgagcctgc ctgaccttga cagcagcctg   1140
gccagtatcc aagagctcct gtctccccag gagccccca ggcctccga ggcagagaac    1200
```
agcagcccgg attcagggaa gcagctggtg cactacacag cgcagccgct gttcctgctg     1260
gaccccggct ccgtggacac cgggagcaac gacctgccgg tgctgtttga gctgggagag     1320
ggctcctact tctccgaagg ggacggcttc gccgaggacc ccaccatctc cctgctgaca     1380
ggctcggagc ctcccaaagc caaggacccc actgtctcc                            1419

<210> SEQ ID NO 40
<211> LENGTH: 130
<212> TYPE: PRT
<213> ORGANISM: Artificial Sequence
<220> FEATURE:
<223> OTHER INFORMATION: Synthetic

<400> SEQUENCE: 40

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Lys Arg Lys Tyr Thr Ile Lys Val Glu
50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
130

<210> SEQ ID NO 41
<211> LENGTH: 390
<212> TYPE: DNA
<213> ORGANISM: Artificial Sequence
<220> FEATURE:
<223> OTHER INFORMATION: Synthetic

<400> SEQUENCE: 41
atggcttcaa actttactca gttcgtgctc gtggacaatg gtgggacagg ggatgtgaca      60
gtggctcctt ctaatttcgc taatggggtg cagagtggaa tcagctccaa ctcacggagc     120
caggcctaca ggtgacatg cagcgtcagg cagtctagtg cccagaagag aaagtatacc     180
atcaaggtgg aggtccccaa agtggctacc agacagtgg gcggagtcga actgcctgtc      240
gccgcttgga ggtcctacct gaacatggag ctcactatcc caatttttcgc taccaattct     300 gactgtgaac tcatcgtgaa ggcaatgcag gggctcctca agacggtaa tcctatccct      360 tccgccatcg ccgctaactc aggtatctac                                       390

<210> SEQ ID NO 42
<211> LENGTH: 6673
<212> TYPE: DNA
<213> ORGANISM: Artificial Sequence
<220> FEATURE:
<223> OTHER INFORMATION: Synthetic

<400> SEQUENCE: 42

```
gtgcccgtca gtgggcagag cgcacatcgc ccacagtccc cgagaagttg gggggagggg      60
tcggcaattg aaccggtgcc tagagaaggt ggcgcgggt aaactgggaa agtgatgtcg      120
tgtactggct ccgcctttt cccgagggtg ggggagaacc gtatataagt gcagtagtcg      180
ccgtgaacgt tcttttttcgc aacgggtttg ccgccagaac acaggtaagt gccgtgtgtg     240
gttcccgcgg gcctggcctc tttacgggtt atggcccttg cgtgccttga attacttcca     300
cctggctgca gtacgtgatt cttgatcccg agcttcgggt tggaagtggg tgggagagtt     360
cgaggccttg cgcttaagga gcccttcgc ctcgtgcttg agttgaggcc tggcctgggc      420
gctgggccg ccgcgtgcga atctggtggc accttcgcgc ctgtctcgct gctttcgata      480
agtctctagc catttaaaat ttttgatgac ctgctgcgac gctttttttc tggcaagata     540
gtcttgtaaa tgcgggccaa gatctgcaca ctggtatttc ggttttttggg gccgcgggcg    600
gcgacggggc ccgtgcgtcc cagcgcacat gttcggcgag gcgggcctg cgagcgcggc     660
caccgagaat cggacggggg tagtctcaag ctggccggcc tgctctggtg cctggcctcg     720
cgccgccgtg tatcgccccg ccctgggcgg caaggctggc ccggtcggca ccagttgcgt    780
gagcggaaag atggccgctt cccggccctg ctgcagggag ctcaaaatgg aggacgcggc     840
gctcgggaga gcgggcgggt gagtcaccca cacaaaggaa aagggccttt ccgtcctcag     900
ccgtcgcttc atgtgactcc acggagtacc gggcgccgtc caggcacctc gattagttct     960
cgagcttttg gagtacgtcg tctttaggtt gggggaggg gttttatgcg atggagttc     1020
cccacactga gtgggtggag actgaagtta ggccagcttg gcacttgatg taattctcct    1080
tggaatttgc ccttttttgag tttggatctt ggttcattct caagcctcag acagtggttc    1140
aaagttttt tcttccattt caggtgtcgt gacgtacggc caccatgaaa aggccggcgg     1200
ccacgaaaaa ggccggccag gcaaaaaaga aaaaggacaa gaagtacagc atcggcctgg    1260
ccatcggcac caactctgtg ggctgggccg tgatcaccga cgagtacaag gtgcccagca    1320
agaaattcaa ggtgctgggc aacaccgacc ggcacagcat caagaagaac ctgatcggag    1380
ccctgctgtt cgacagcggc gaaacagccg aggccacccg gctgaagaga accgccagaa    1440
gaagatacac cagacggaag aaccggatct gctatctgca agatcttc agcaacgaga    1500
tggccaaggt ggacgacagc ttcttccaca gactggaaga gtccttcctg gtggaagagg    1560
ataagaagca cgagcggcac cccatcttcg caacatcgt ggacgaggtg cctaccacg    1620
agaagtaccc caccatctac cacctgagaa agaaactggt ggacagcacc gacaaggccg    1680
acctgcggct gatctatctg gccctggccc acatgatcaa gttccggggc cacttcctga    1740
tcgagggcga cctgaacccc gacaacagcg acgtggacaa gctgttcatc cagctggtgc    1800
agacctacaa ccagctgttc gaggaaaacc ccatcaacgc cagcggcgtg gacgccaagg    1860
ccatcctgtc tgccagactg agcaagagca cacggctgga aaatctgatc gcccagctgc    1920
ccggcgagaa gaagaatggc ctgttcggca acctgattgc cctgagcctg ggcctgaccc    1980
ccaacttcaa gagcaacttc gacctggccg aggatgccaa actgcagctg agcaaggaca    2040
cctacgacga cgacctggac aacctgctgg cccagatcgg cgaccagtac gccgacctgt    2100
ttctggccgc caagaacctg tccgacgcca tcctgctgag cgacatcctg agagtgaaca    2160
ccgagatcac caaggccccc ctgagcgcct ctatgatcaa gagatacgac gagcaccacc    2220
aggacctgac cctgctgaaa gctctcgtgc ggcagcagct gcctgagaag tacaaagaga    2280
ttttcttcga ccagagcaag aacggctacg ccggctacat tgacggcgga gccagccagg    2340
aagagttcta caagttcatc aagcccatcc tggaaaagat ggacggcacc gaggaactgc    2400
```

```
tcgtgaagct gaacagagag gacctgctgc ggaagcagcg gaccttcgac aacggcagca   2460
tcccccacca gatccacctg ggagagctgc acgccattct gcggcggcag gaagattttt   2520
acccattcct gaaggacaac cgggaaaaga tcgagaagat cctgaccttc cgcatcccct   2580
actacgtggg ccctctggcc aggggaaaca gcagattcgc ctggatgacc agaaagagcg   2640
aggaaaccat cacccctgg aacttcgagg aagtggtgga caagggcgct tccgcccaga   2700
gcttcatcga gcggatgacc aacttcgata agaacctgcc caacgagaag gtgctgccca   2760
agcacagcct gctgtacgag tacttcaccg tgtataacga gctgaccaaa gtgaaatacg   2820
tgaccgaggg aatgagaaag cccgccttcc tgagcggcga gcagaaaaag gccatcgtgg   2880
acctgctgtt caagaccaac cggaaagtga ccgtgaagca gctgaaagag gactacttca   2940
agaaaatcga gtgcttcgac tccgtggaaa tctccggcgt ggaagatcgg ttcaacgcct   3000
ccctgggcac ataccacgat ctgctgaaaa ttatcaagga caaggacttc ctggacaatg   3060
aggaaaacga ggacattctg gaagatatcg tgctgaccct gacactgttt gaggacagag   3120
agatgatcga ggaacggctg aaaacctatg cccacctgtt cgacgacaaa gtgatgaagc   3180
agctgaagcg gcggagatac accggctggg gcaggctgag ccggaagctg atcaacggca   3240
tccgggacaa gcagtccggc aagacaatcc tggatttcct gaagtccgac ggcttcgcca   3300
acagaaactt catgcagctg atccacgacg acagcctgac ctttaaagag gacatccaga   3360
aagcccaggt gtccggccag ggcgatagcc tgcacgagca cattgccaat ctggccggca   3420
gccccgccat taagaagggc atcctgcaga cagtgaaggt ggtggacgag ctcgtgaaag   3480
tgatgggccg gcacaagccc gagaacatcg tgatcgaaat ggccagagag aaccagacca   3540
cccagaaggg acagaagaac agccgcgaga gaatgaagcg gatcgaagag ggcatcaaag   3600
agctgggcag ccagatcctg aaagaacacc ccgtggaaaa cacccagctg cagaacgaga   3660
agctgtacct gtactacctg cagaatgggc gggatatgta cgtggaccag gaactggaca   3720
tcaaccggct gtccgactac gatgtggacc acatcgtgcc tcagagcttt ctgaaggacg   3780
actccatcga caacaaggtg ctgaccagaa gcgacaaggc ccggggcaag agcgacaacg   3840
tgccctccga agaggtcgtg aagaagatga aaaactactg gcggcagctg ctgaacgcca   3900
agctgattac ccagagaaag ttcgacaatc tgaccaaggc cgagagaggc ggcctgagcg   3960
aactggataa ggccggcttc atcaagagac agctggtgga aacccggcag atcacaaagc   4020
acgtggcaca gatcctggac tcccggatga acactaagta cgacgagaat gacaagctga   4080
tccgggaagt gaaagtgatc accctgaagt ccaagctggt gtccgatttc cggaaggatt   4140
tccagtttta caaagtgcgc gagatcaaca actaccacca cgcccacgac gcctacctga   4200
acgccgtcgt gggaaccgcc ctgatcaaaa agtaccctaa gctggaaagc gagttcgtgt   4260
acggcgacta caaggtgtac gacgtgcgga agatgatcgc caagagcgag caggaaatcg   4320
gcaaggctac cgccaagtac ttcttctaca gcaacatcat gaactttttc aagaccgaga   4380
ttaccctggc caacggcgag atccggaagc ggcctctgat cgagacaaac ggcgaaaccg   4440
gggagatcgt gtgggataag gccgggatt ttgccaccgt gcggaaagtg ctgagcatgc   4500
cccaagtgaa tatcgtgaaa aagaccgagg tgcagacagg cggcttcagc aaagagtcta   4560
tcctgcccaa gaggaacagc gataagctga tcgccagaaa gaaggactgg gaccctaaga   4620 agtacgcgg cttcgacagc cccaccgtgg cctattctgt gctggtggtg gccaaagtgg   4680
aaaagggcaa gtccaagaaa ctgaagagtg tgaaagagct gctgggatc accatcatgg   4740
```

| | |
|---|---|
| aaagaagcag cttcgagaag aatcccatcg actttctgga agccaagggc tacaaagaag | 4800 |
| tgaaaaagga cctgatcatc aagctgccta agtactccct gttcgagctg gaaaacggcc | 4860 |
| ggaagagaat gctggcctct gccggcgaac tgcagaaggg aaacgaactg ccctgccct | 4920 |
| ccaaatatgt gaacttcctg tacctggcca gccactatga aagctgaag gctcccccg | 4980 |
| aggataatga gcagaaacag ctgtttgtgg aacagcacaa gcactacctg gacgagatca | 5040 |
| tcgagcagat cagcgagttc tccaagagag tgatcctggc cgacgctaat ctggacaaag | 5100 |
| tgctgtccgc ctacaacaag caccgggata agcccatcag agagcaggcc gagaatatca | 5160 |
| tccacctgtt taccctgacc aatctgggag cccctgccgc cttcaagtac tttgacacca | 5220 |
| ccatcgaccg gaagaggtac accagcacca aagaggtgct ggacgccacc ctgatccacc | 5280 |
| agagcatcac cggcctgtac gagacacgga tcgacctgtc tcagctggga ggcgacagcg | 5340 |
| ctggaggagg tggaagcgga ggaggaggaa gcggaggagg aggtagcgga cctaagaaaa | 5400 |
| agaggaaggt ggcggccgct ggatccggac gggctgacgc attggacgat tttgatctgg | 5460 |
| atatgctggg aagtgacgcc ctcgatgatt ttgaccttga catgcttggt tcggatgccc | 5520 |
| ttgatgactt tgacctcgac atgctcggca gtgacgccct tgatgatttc gacctggaca | 5580 |
| tgctgattaa ctgtacaggc agtggagagg gcagaggaag tctgctaaca tgcggtgacg | 5640 |
| tcgaggagaa tcctggccca atggccaagc ctttgtctca agaagaatcc accctcattg | 5700 |
| aaagagcaac ggctacaatc aacagcatcc ccatctctga agactacagc gtcgccagcg | 5760 |
| cagctctctc tagcgacggc cgcatcttca ctggtgtcaa tgtatatcat tttactgggg | 5820 |
| gaccttgtgc agaactcgtg gtgctgggca ctgctgctgc tgcggcagct ggcaacctga | 5880 |
| cttgtatcgt cgcgatcgga aatgagaaca ggggcatctt gagcccctgc ggacggtgcc | 5940 |
| gacaggtgct tctcgatctg catcctggga tcaaagccat agtgaaggac agtgatggac | 6000 |
| agccgacggc agttgggatt cgtgaattgc tgccctctgg ttatgtgtgg gagggctaag | 6060 |
| aattcgatat caagcttatc ggtaatcaac ctctggatta caaaatttgt gaaagattga | 6120 |
| ctggtattct taactatgtt gctcctttta cgctatgtgg atacgctgct ttaatgcctt | 6180 |
| tgtatcatgc tattgcttcc cgtatggctt tcattttctc ctccttgtat aaatcctggt | 6240 |
| tgctgtctct ttatgaggag ttgtggcccg ttgtcaggca acgtggcgtg gtgtgcactg | 6300 |
| tgtttgctga cgcaaccccc actggttggg gcattgccac cacctgtcag ctcctttccg | 6360 |
| ggactttcgc tttccccctc cctattgcca cggcggaact catcgccgcc tgccttgccc | 6420 |
| gctgctggac aggggctcgg ctgttgggca ctgacaattc cgtggtgttg tcggggaaat | 6480 |
| catcgtcctt tccttggctg ctcgcctgtg ttgccacctg gattctgcgc gggacgtcct | 6540 |
| tctgctacgt cccttcggcc ctcaatccag cggaccttcc ttcccgcggc ctgctgccgg | 6600 |
| ctctgcggcc tcttccgcgt cttcgccttc gccctcagac gagtcggatc tccctttggg | 6660 |
| ccgcctcccc gca | 6673 |

<210> SEQ ID NO 43
<211> LENGTH: 4324
<212> TYPE: DNA
<213> ORGANISM: Artificial Sequence
<220> FEATURE:
<223> OTHER INFORMATION: Synthetic

<400> SEQUENCE: 43

| | |
|---|---|
| gtgcccgtca gtgggcagag cgcacatcgc ccacagtccc cgagaagttg gggggagggg | 60 |
| tcggcaattg aaccggtgcc tagagaaggt ggcgcggggt aaactgggaa agtgatgtcg | 120 |

-continued

```
tgtactggct ccgccttttt cccgagggtg ggggagaacc gtatataagt gcagtagtcg      180
ccgtgaacgt tctttttcgc aacgggtttg ccgccagaac acaggtaagt gccgtgtgtg      240
gttcccgcgg gcctggcctc tttacgggtt atggcccttg cgtgccttga attacttcca      300
cctggctgca gtacgtgatt cttgatcccg agcttcgggt tggaagtggg tgggagagtt      360
cgaggccttg cgcttaagga gccccttcgc ctcgtgcttg agttgaggcc tggcctgggc      420
gctggggccg ccgcgtgcga atctggtggc accttcgcgc ctgtctcgct gctttcgata      480
agtctctagc catttaaaat ttttgatgac ctgctgcgac gctttttttc tggcaagata      540
gtcttgtaaa tgcgggccaa gatctgcaca ctggtatttc ggttttttggg gccgcgggcg      600 gcgacggggc ccgtgcgtcc cagcgcacat gttcggcgag gcggggcctg cgagcgcggc      660
caccgagaat cggacggggg tagtctcaag ctggccggcc tgctctggtg cctgcctcg      720 cgccgccgtg tatcgccccg ccctgggcgg caaggctggc ccggtcggca ccagttgcgt      780
gagcggaaag atgccgcttc ccggccctg ctgcagggag ctcaaaatgg aggacgcggc      840
gctcgggaga gcggcgggt gagtcaccca cacaaaggaa aagggccttt ccgtcctcag      900
ccgtcgcttc atgtgactcc acggagtacc gggcgccgtc caggcacctc gattagttct      960
cgagcttttg gagtacgtcg tctttaggtt gggggagggg gttttatgcg atggagtttc     1020
cccacactga gtgggtggag actgaagtta ggccagcttg gcacttgatg taattctcct     1080
tggaatttgc cctttttgag tttggatctt ggttcattct caagcctcag acagtggttc     1140
aaagtttttt tcttccattt caggtgtcgt gacgtacggc caccatggct tcaaacttta     1200
ctcagttcgt gctcgtggac aatggtggga caggggatgt gacagtggct ccttctaatt     1260
tcgctaatgg ggtggcagag tggatcagct ccaactcacg gagccaggcc tacaaggtga     1320
catgcagcgt caggcagtct agtgcccaga agagaaagta taccatcaag gtggaggtcc     1380
ccaaagtggc tacccagaca gtgggcgagg tcgaactgcc tgtcgccgct tggaggtcct     1440
acctgaacat ggagctcact atcccaattt tcgctaccaa ttctgactgt gaactcatcg     1500
tgaaggcaat gcaggggctc ctcaaagacg gtaatcctat cccttccgcc atcgccgcta     1560
actcaggtat ctacagcgct ggaggaggtg gaagcggagg aggaggaagc ggaggaggag     1620
gtagcggacc taagaaaaag aggaaggtgg cggccgctgg atcccccttca gggcagatca     1680 gcaaccaggc cctggctctg gcccctagct ccgctccagt gctggcccag actatggtgc     1740
cctctagtgc tatggtgcct ctggcccagc cacctgctcc agcccctgtg ctgaccccag     1800 gaccaccca gtcactgagc gctccagtgc ccaagtctac acaggccggc gaggggactc     1860
tgagtgaagc tctgctgcac ctgcagttcg acgctgatga ggacctggga gctctgctgg     1920
ggaacagcac cgatcccgga gtgttcacag atctggcctc cgtggacaac tctgagtttc     1980
agcagctgct gaatcagggc gtgtccatgt ctcatagtac agccgaacca atgctgatgg     2040 agtacccga agccattacc cggctggtga ccggcagcca gcggcccccc gaccccgctc     2100
caactcccct gggaaccagc ggcctgccta atgggctgtc cggagatgaa gacttctcaa     2160
gcatcgctga tatggacttt agtgccctgc tgtcacagat ttcctctagt gggcagggag     2220
gaggtggaag cggcttcagc gtggacacca gtgccctgct ggacctgttc agcccctcgg     2280
tgaccgtgcc cgacatgagc ctgcctgacc ttgacagcag cctggccagt atccaagagc     2340
tcctgtctcc ccaggagccc cccaggcctc ccgaggcaga aacagcagc ccggattcag     2400 ggaagcagct ggtgcactac acagcgcagc cgctgttcct gctggacccc ggctccgtgg     2460
```

-continued

| | |
|---|---|
| acaccgggag caacgacctg ccggtgctgt ttgagctggg agagggctcc tacttctccg | 2520 |
| aaggggacgg cttcgccgag gaccccacca tctccctgct gacaggctcg gagcctccca | 2580 |
| aagccaagga ccccactgtc tcctgtacag gcagtggaga gggcagagga agtctgctaa | 2640 |
| catgcggtga cgtcgaggag aatcctggcc caaccatgaa aaagcctgaa ctcaccgcta | 2700 |
| cctctgtcga gaagtttctg atcgaaaagt tcgacagcgt ctccgacctg atgcagctct | 2760 |
| ccgagggcga agaatctcgg gctttcagct tcgatgtggg agggcgtgga tatgtcctgc | 2820 |
| gggtgaatag ctgcgccgat ggtttctaca agatcgcta tgtttatcgg cactttgcat | 2880 |
| ccgccgctct ccctattccc gaagtgcttg acattgggga gttcagcgag agcctgacct | 2940 |
| attgcatctc ccgccgtgca cagggtgtca ccttgcaaga cctgcctgaa accgaactgc | 3000 |
| ccgctgttct ccagcccgtc gccgaggcca tggatgccat cgctgccgcc gatcttagcc | 3060 |
| agaccagcgg gttcggccca ttcggacctc aaggaatcgg tcaatacact acatggcgcg | 3120 |
| atttcatctg cgctattgct gatcccatg tgtatcactg gcaaactgtg atggacgaca | 3180 |
| ccgtcagtgc ctccgtcgcc caggctctcg atgagctgat gctttgggcc gaggactgcc | 3240 |
| ccgaagtccg gcacctcgtg cacgccgatt tcggctccaa caatgtcctg accgacaatg | 3300 |
| gccgcataac agccgtcatt gactggagcg aggccatgtt cggggattcc caatacgagg | 3360 |
| tcgccaacat cttcttctgg aggccctggt tggcttgtat ggagcagcag accgctact | 3420 |
| tcgagcggag gcatcccgag cttgcaggat ctcctcggct ccgggcttat atgctccgca | 3480 |
| ttggtcttga ccaactctat cagagcttgg ttgacggcaa tttcgatgat gcagcttggg | 3540 |
| ctcagggtcg ctgcgacgca atcgtccggt ccggagccgg gactgtcggg cgtacacaaa | 3600 |
| tcgcccgcag aagcgctgcc gtctggaccg atggctgtgt ggaagtgctc gccgatagtg | 3660 |
| gaaacagacg ccccagcact cgtcctaggg caaaggatct gcagtaatga gaattcgata | 3720 |
| tcaagcttat cggtaatcaa cctctggatt acaaaatttg tgaaagattg actggtattc | 3780 |
| ttaactatgt tgctcctttt acgctatgtg gatacgctgc tttaatgcct ttgtatcatg | 3840 |
| ctattgcttc ccgtatggct ttcattttct cctccttgta taaatcctgg ttgctgtctc | 3900 |
| tttatgagga gttgtggccc gttgtcaggc aacgtggcgt ggtgtgcact gtgtttgctg | 3960 |
| acgcaacccc cactggttgg ggcattgcca ccacctgtca gctcctttcc gggactttcg | 4020 |
| ctttccccct ccctattgcc acggcggaac tcatcgccgc ctgccttgcc cgctgctgga | 4080 |
| caggggctcg gctgttgggc actgacaatt ccgtggtgtt gtcggggaaa tcatcgtcct | 4140 |
| ttccttggct gctcgcctgt gttgccacct ggattctgcg cgggacgtcc ttctgctacg | 4200 |
| tcccttcggc cctcaatcca gcggaccttc cttcccgcgg cctgctgccg gctctgcggc | 4260 |
| ctcttccgcg tcttcgcctt cgccctcaga cgagtcggat ctccctttgg gccgcctccc | 4320 |
| cgca | 4324 |

CRISPR/CAS DROPOUT SCREENING PLATFORM TO REVEAL GENETIC VULNERABILITIES ASSOCIATED WITH TAU AGGREGATION

CROSS-REFERENCE TO RELATED APPLICATIONS

This application claims the benefit of U.S. Application No. 62/820,101, filed Mar. 18, 2019, which is herein incorporated by reference in its entirety for all purposes.

REFERENCE TO A SEQUENCE LISTING SUBMITTED AS A TEXT FILE VIA EFS WEB

The Sequence Listing written in file 544671SEQLIST.txt is 75.7 kilobytes, was created on Mar. 16, 2020, and is hereby incorporated by reference.

BACKGROUND

Abnormal aggregation or fibrillization of proteins is a defining feature of many diseases, notably including a number of neurodegenerative diseases such as Alzheimer's disease (AD), Parkinson's disease (PD), frontotemporal dementia (FTD), amyotrophic lateral sclerosis (ALS), chronic traumatic encephalopathy (CTE), Creutzfeldt-Jakob disease (CJD), and others. In many of these diseases, the fibrillization of certain proteins into insoluble aggregates is not only a hallmark of disease, but has also been implicated as a causative factor of neurotoxicity. Furthermore, these diseases are characterized by propagation of aggregate pathology through the central nervous system following stereotypical patterns, a process which correlates with disease progression. The identification of genes and genetic pathways that modify the processes of abnormal protein aggregation, or cell-to-cell propagation of aggregates, are therefore of great value in better understanding neurodegenerative disease etiology as well as in devising strategies for therapeutic intervention.

SUMMARY

Provided herein are methods of screening for genetic vulnerabilities associated with tau aggregation. Also provided herein are Cas-tau biosensor cells or populations of such cells and in vitro cultures of Cas-tau biosensor cells and a culture medium. Also provided herein are CRISPR/Cas synergistic activation mediator (SAM)-tau biosensor cells or populations of such cells and in vitro cultures of SAM-tau biosensor cells and a culture medium.

In one aspect, provided are methods of screening for genetic vulnerabilities associated with tau aggregation. Some such methods comprise: (a) providing an aggregation-positive population of cells and an aggregation-negative population of cells, wherein each population of cells comprises a Cas protein, a first tau repeat domain linked to a first reporter, and a second tau repeat domain linked to a second reporter, wherein in the aggregation-positive population of cells the first tau repeat domain linked to the first reporter and the second tau repeat domain linked to the second reporter stably present in an aggregated state, and wherein in the aggregation-negative population of cells the first tau repeat domain linked to the first reporter and the second tau repeat domain linked to the second reporter do not stably present in an aggregated state; (b) introducing into each population of cells a library comprising a plurality of unique guide RNAs that target a plurality of genes, wherein the plurality of unique guide RNAs form complexes with the Cas protein, and the Cas protein cleaves the plurality of genes resulting in knockout of gene function; and (c) determining abundance of each of the plurality of unique guide RNAs at a plurality of time points over a time course in each population of cells, wherein depletion of a guide RNA in the aggregation-positive population of cells but not in the aggregation-negative population of cells or a more dramatic depletion pattern of a guide RNA over the time course in the aggregation-positive population of cells relative to the aggregation-negative population of cells indicates that the gene targeted by the guide RNA exhibits synthetic lethality with tau protein aggregates and is a genetic vulnerability associated with tau aggregation or is a candidate genetic vulnerability associated tau aggregation (e.g., for further testing via secondary screens). Guide RNAs targeting such genes cause selective cell death in the Agg[+] cells but not in the Agg[−] cells.

In some such methods, the first tau repeat domain and/or the second tau repeat domain is a human tau repeat domain. In some such methods, the first tau repeat domain and/or the second tau repeat domain comprises a pro-aggregation mutation. Optionally, the first tau repeat domain and/or the second tau repeat domain comprises a tau P301S mutation. In some such methods, the first tau repeat domain and/or the second tau repeat domain comprises a tau four-repeat domain. In some such methods, the first tau repeat domain and/or the second tau repeat domain comprises SEQ ID NO: 11. In some such methods, the first tau repeat domain and the second tau repeat domain are the same. In some such methods, the first tau repeat domain and the second tau repeat domain are the same and each comprises tau four-repeat domain comprising a tau P301S mutation.

In some such methods, the first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such methods, the Cas protein is a Cas9 protein. Optionally, the Cas protein is *Streptococcus pyogenes* Cas9. Optionally, the Cas protein comprises SEQ ID NO: 21. Optionally, the Cas protein is encoded by a coding sequence comprising the sequence set forth in SEQ ID NO: 22.

In some such methods, the Cas protein, the first tau repeat domain linked to the first reporter, and the second tau repeat domain linked to the second reporter are stably expressed in the populations of cells. In some such methods, nucleic acids encoding the Cas protein, the first tau repeat domain linked to the first reporter, and the second tau repeat domain linked to the second reporter are genomically integrated in the populations of cells.

In some such methods, the cells are eukaryotic cells. Optionally, the cells are mammalian cells. Optionally, the cells are human cells. Optionally, the cells are HEK293T cells.

In some such methods, the plurality of unique guide RNAs are introduced at a concentration selected such that a majority of the cells receive only one of the unique guide RNAs. In some such methods, the plurality of unique guide RNAs target 100 or more genes, 1000 or more genes, or 10000 or more genes. In some such methods, the library is a genome-wide library. In some such methods, a plurality of target sequences are targeted on average in each of the targeted plurality of genes. Optionally, at least three target sequences are targeted on average in each of the targeted plurality of genes. Optionally, about three to about six target sequences (e.g., about three, about four, or about six) are targeted on average in each of the targeted plurality of genes.

In some such methods, each guide RNA targets a constitutive exon. Optionally, each guide RNA targets a 5' constitutive exon. In some such methods, each guide RNA targets a first exon, a second exon, or a third exon.

In some such methods, the plurality of unique guide RNAs are introduced into the populations of cells by viral transduction. Optionally, each of the plurality of unique guide RNAs is in a separate viral vector. In some such methods, the plurality of unique guide RNAs are introduced into the populations of cells by lentiviral transduction. In some such methods, the populations of cells are infected at a multiplicity of infection of less than about 0.3.

In some such methods, the plurality of unique guide RNAs are introduced into the populations of cells together with a selection marker, and step (b) further comprises selecting cells that comprise the selection marker. Optionally, the selection marker imparts resistance to a drug. Optionally, the selection marker imparts resistance to puromycin or zeocin. Optionally, the selection marker is selected from neomycin phosphotransferase, hygromycin B phosphotransferase, puromycin-N-acetyltransferase, and blasticidin S deaminase. Optionally, the selection marker is selected from neomycin phosphotransferase, hygromycin B phosphotransferase, puromycin-N-acetyltransferase, blasticidin S deaminase, and bleomycin resistance protein.

In some such methods, the populations of cells into which the plurality of unique guide RNAs are introduced in step (b) each comprise greater than about 500 cells per unique guide RNA.

In some such methods, the time course in step (c) is more than about 1 week. Optionally, the time course in step (c) is more than about 2 weeks. In some such methods, the time course in step (c) comprises about 10 to about 15 cell doublings. In some such methods, the plurality of time points in step (c) comprises at least three time points. Optionally, the plurality of time points in step (c) comprises about four time points or about six time points. In some such methods, there is more than about 1 day between each time point in step (c). Optionally, there is more than about 2 days between each time point in step (c). Optionally, there is between about 3 to about 4 days between each time point in step (c).

In some such methods, a gene is considered to exhibit synthetic lethality with tau protein aggregates in step (c) (or is expected to exhibit synthetic lethality with tau protein aggregates) if a guide RNA targeting the gene is depleted in the aggregation-positive population of cells but not in the aggregation-negative population of cells. Optionally, a gene is considered to exhibit synthetic lethality with tau protein aggregates in step (c) (or is expected to exhibit synthetic lethality with tau protein aggregates) if a guide RNA targeting the gene has a more dramatic depletion pattern over the time course in the aggregation-positive population of cells relative to the aggregation-negative population of cells.

In some such methods, a guide RNA is considered depleted in step (c) if the abundance of the guide RNA at each time point is less than or equal to the abundance of the guide RNA at the preceding time point. In some such methods, a guide RNA is considered depleted in step (c) if the abundance of the guide RNA at each time point after the second time point is less than or equal to the abundance of the time point two time points prior.

In some such methods, a gene is considered to exhibit synthetic lethality with tau protein aggregates in step (c) (or is expected to exhibit synthetic lethality with tau protein aggregates) if more than about 30% of the guide RNAs in the library that target the gene are depleted in the aggregation-positive population of cells but not in the aggregation-negative population of cells. Optionally, a gene is considered to exhibit synthetic lethality with tau protein aggregates in step (c) (or is expected to exhibit synthetic lethality with tau protein aggregates) in any one of the following situations: (1) there is one guide RNA in the library that targets the gene, and the one guide RNA is depleted in the aggregation-positive population of cells but not in the aggregation-negative population of cells; (2) there are two guide RNAs in the library that target the gene, and at least one of the two guide RNAs is depleted in the aggregation-positive population of cells but not in the aggregation-negative population of cells; (3) there are three guide RNAs in the library that target the gene, and at least one of the three guide RNAs is depleted in the aggregation-positive population of cells but not in the aggregation-negative population of cells; (4) there are four guide RNAs in the library that target the gene, and at least two of the four guide RNAs is depleted in the aggregation-positive population of cells but not in the aggregation-negative population of cells; (5) there are five guide RNAs in the library that target the gene, and at least two of the five guide RNAs is depleted in the aggregation-positive population of cells but not in the aggregation-negative population of cells; and (6) there are six guide RNAs in the library that target the gene, and at least three of the six guide RNAs is depleted in the aggregation-positive population of cells but not in the aggregation-negative population of cells.

In some such methods, the method is repeated at least three times in at least three different experiments, and a gene is considered to exhibit synthetic lethality with tau protein aggregates (or is expected to exhibit synthetic lethality with tau protein aggregates) if it is considered to exhibit synthetic lethality with tau protein aggregates in more than about 50% of the at least three different experiments.

In some such methods, the time course in step (c) is more than about 2 weeks, wherein the plurality of time points in step (c) comprises about six time points, wherein there is between about 3 to about 4 days between each time point in step (c), wherein a guide RNA is considered depleted in step (c) if the abundance of the guide RNA at each time point after the second time point is less than or equal to the abundance of the time point two time points prior, and wherein a gene is considered to exhibit synthetic lethality with tau protein aggregates in step (c) (or is expected to exhibit synthetic lethality with tau protein aggregates) if more than about 30% of the guide RNAs in the library that target the gene are depleted in the aggregation-positive population of cells but not in the aggregation-negative population of cells.

Other such methods utilize CRISPR activation (CRISPR/Cas synergistic activation mediator (SAM)) guide RNA libraries. Some such methods comprise: (a) providing an aggregation-positive population of cells and an aggregation-negative population of cells, wherein each population of cells comprises a chimeric Cas protein comprising a nuclease-inactive Cas protein (i.e., catalytically inactive Cas protein) fused to one or more transcriptional activation domains, a chimeric adaptor protein comprising an adaptor protein fused to one or more transcriptional activation domains, a first tau repeat domain linked to a first reporter, and a second tau repeat domain linked to a second reporter, wherein in the aggregation-positive population of cells the first tau repeat domain linked to the first reporter and the second tau repeat domain linked to the second reporter stably present in an aggregated state, and wherein in the aggregation-negative population of cells the first tau repeat domain linked to the first reporter and the second tau repeat domain linked to the second reporter do not stably present in an aggregated state; (b) introducing into each population of cells a library comprising a plurality of unique guide RNAs that target a plurality of genes, wherein the plurality of unique guide RNAs form complexes with the chimeric Cas protein and the chimeric adaptor protein, and the complexes activate transcription of the plurality of genes resulting in increased gene expression; and (c) determining abundance of each of the plurality of unique guide RNAs at a plurality of time points over a time course in each population of cells, wherein depletion of a guide RNA in the aggregation-positive population of cells but not in the aggregation-negative population of cells or a more dramatic depletion pattern of a guide RNA over the time course in the aggregation-positive population of cells relative to the aggregation-negative population of cells indicates that activation of the gene targeted by the guide RNA exhibits synthetic lethality with tau protein aggregates and is a genetic vulnerability associated with tau aggregation or is a candidate genetic vulnerability associated tau aggregation (e.g., for further testing via secondary screens).

In some such methods, the first tau repeat domain and/or the second tau repeat domain is a human tau repeat domain. In some such methods, the first tau repeat domain and/or the second tau repeat domain comprises a pro-aggregation mutation. Optionally, the first tau repeat domain and/or the second tau repeat domain comprises a tau P301S mutation. In some such methods, the first tau repeat domain and/or the second tau repeat domain comprises a tau four-repeat domain. In some such methods, the first tau repeat domain and/or the second tau repeat domain comprises SEQ ID NO: 11. In some such methods, the first tau repeat domain and the second tau repeat domain are the same. In some such methods, the first tau repeat domain and the second tau repeat domain are the same and each comprises tau four-repeat domain comprising a tau P301S mutation.

In some such methods, the first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such methods, the Cas protein is a Cas9 protein. Optionally, the Cas protein is *Streptococcus pyogenes* Cas9. In some such methods, the chimeric Cas protein comprises the nuclease-inactive Cas protein fused to a VP64 transcriptional activation domain, optionally wherein the chimeric Cas protein comprises from N-terminus to C-terminus: the nuclease-inactive Cas protein; a nuclear localization signal; and the VP64 transcriptional activator domain. In some such methods, the adaptor protein is an MS2 coat protein, and the one or more transcriptional activation domains in the chimeric adaptor protein comprise a p65 transcriptional activation domain and an HSF1 transcriptional activation domain, optionally wherein the chimeric adaptor protein comprises from N-terminus to C-terminus: the MS2 coat protein; a nuclear localization signal; the p65 transcriptional activation domain; and the HSF1 transcriptional activation domain. In some such methods, the chimeric Cas protein comprises SEQ ID NO: 36, optionally wherein the chimeric Cas protein is encoded by a coding sequence comprising the sequence set forth in SEQ ID NO: 38. In some such methods, the chimeric adaptor protein comprises SEQ ID NO: 37, optionally wherein the chimeric adaptor protein is encoded by a coding sequence comprising the sequence set forth in SEQ ID NO: 39.

In some such methods, the chimeric Cas protein, the chimeric adaptor protein, the first tau repeat domain linked to the first reporter, and the second tau repeat domain linked to the second reporter are stably expressed in the population of cells. In some such methods, nucleic acids encoding the chimeric Cas protein, the chimeric adaptor protein, the first tau repeat domain linked to the first reporter, and the second tau repeat domain linked to the second reporter are genomically integrated in the populations of cells.

In some such methods, the cells are eukaryotic cells. Optionally, the cells are mammalian cells. Optionally, the cells are human cells. Optionally, the cells are HEK293T cells.

In some such methods, the plurality of unique guide RNAs are introduced at a concentration selected such that a majority of the cells receive only one of the unique guide RNAs. In some such methods, the plurality of unique guide RNAs target 100 or more genes, 1000 or more genes, or 10000 or more genes. In some such methods, the library is a genome-wide library. In some such methods, a plurality of target sequences are targeted on average in each of the targeted plurality of genes. Optionally, at least three target sequences are targeted on average in each of the targeted plurality of genes. Optionally, about three to about six target sequences (e.g., about three, about four, or about six) are targeted on average in each of the targeted plurality of genes. Optionally, about three target sequences are targeted on average in each of the targeted plurality of genes In some such methods, each guide RNA targets a guide RNA target sequence within 200 bp upstream of a transcription start site. In some such methods, each guide RNA comprises one or more adaptor-binding elements to which the chimeric adaptor protein can specifically bind. Optionally, each guide RNA comprises two adaptor-binding elements to which the chimeric adaptor protein can specifically bind. Optionally, a first adaptor-binding element is within a first loop of each of the one or more guide RNAs, and a second adaptor-binding element is within a second loop of each of the one or more guide RNAs. Optionally, the adaptor-binding element comprises the sequence set forth in SEQ ID NO: 33. Optionally, each of one or more guide RNAs is a single guide RNA comprising a CRISPR RNA (crRNA) portion fused to a transactivating CRISPR RNA (tracrRNA) portion, and the first loop is the tetraloop corresponding to residues 13-16 of SEQ ID NO: 17, 19, 30, or 31, and the second loop is the stem loop 2 corresponding to residues 53-56 of SEQ ID NO: 17, 19, 30, or 31.

In some such methods, the plurality of unique guide RNAs are introduced into the populations of cells by viral transduction. Optionally, each of the plurality of unique guide RNAs is in a separate viral vector. In some such methods, the plurality of unique guide RNAs are introduced into the populations of cells by lentiviral transduction. In some such methods, the populations of cells are infected at a multiplicity of infection of less than about 0.3.

In some such methods, the plurality of unique guide RNAs are introduced into the populations of cells together with a selection marker, and step (b) further comprises selecting cells that comprise the selection marker. Optionally, the selection marker imparts resistance to a drug. Optionally, the selection marker imparts resistance to puromycin or zeocin. Optionally, the selection marker is selected from neomycin phosphotransferase, hygromycin B phosphotransferase, puromycin-N-acetyltransferase, and blasticidin S deaminase. Optionally, the selection marker is selected from neomycin phosphotransferase, hygromycin B phosphotransferase, puromycin-N-acetyltransferase, blasticidin S deaminase, and bleomycin resistance protein.

In some such methods, the populations of cells into which the plurality of unique guide RNAs are introduced in step (b) each comprise greater than about 500 cells per unique guide RNA.

In some such methods, the time course in step (c) is more than about 1 week. Optionally, the time course in step (c) is more than about 2 weeks. In some such methods, the time course in step (c) comprises about 10 to about 15 cell doublings. In some such methods, the plurality of time points in step (c) comprises at least three time points. Optionally, the plurality of time points in step (c) comprises about four time points or about six time points. In some such methods, there is more than about 1 day between each time point in step (c). Optionally, there is more than about 2 days between each time point in step (c). Optionally, there is between about 3 to about 4 days between each time point in step (c).

In some such methods, a gene is considered to exhibit synthetic lethality with tau protein aggregates in step (c) (or is expected to exhibit synthetic lethality with tau protein aggregates) if a guide RNA targeting the gene is depleted in the aggregation-positive population of cells but not in the aggregation-negative population of cells. Optionally, a gene is considered to exhibit synthetic lethality with tau protein aggregates in step (c) (or is expected to exhibit synthetic lethality with tau protein aggregates) if a guide RNA targeting the gene has a more dramatic depletion pattern over the time course in the aggregation-positive population of cells relative to the aggregation-negative population of cells.

In some such methods, a guide RNA is considered depleted in step (c) if the abundance of the guide RNA at each time point is less than or equal to the abundance of the guide RNA at the preceding time point. In some such methods, a guide RNA is considered depleted in step (c) if the abundance of the guide RNA at each time point after the second time point is less than or equal to the abundance of the time point two time points prior.

In some such methods, a gene is considered to exhibit synthetic lethality with tau protein aggregates in step (c) (or is expected to exhibit synthetic lethality with tau protein aggregates) if more than about 30% of the guide RNAs in the library that target the gene are depleted in the aggregation-positive population of cells but not in the aggregation-negative population of cells. Optionally, a gene is considered to exhibit synthetic lethality with tau protein aggregates in step (c) (or is expected to exhibit synthetic lethality with tau protein aggregates) in any one of the following situations: (1) there is one guide RNA in the library that targets the gene, and the one guide RNA is depleted in the aggregation-positive population of cells but not in the aggregation-negative population of cells; (2) there are two guide RNAs in the library that target the gene, and at least one of the two guide RNAs is depleted in the aggregation-positive population of cells but not in the aggregation-negative population of cells; (3) there are three guide RNAs in the library that target the gene, and at least one of the three guide RNAs is depleted in the aggregation-positive population of cells but not in the aggregation-negative population of cells; (4) there are four guide RNAs in the library that target the gene, and at least two of the four guide RNAs is depleted in the aggregation-positive population of cells but not in the aggregation-negative population of cells; (5) there are five guide RNAs in the library that target the gene, and at least two of the five guide RNAs is depleted in the aggregation-positive population of cells but not in the aggregation-negative population of cells; and (6) there are six guide RNAs in the library that target the gene, and at least three of the six guide RNAs is depleted in the aggregation-positive population of cells but not in the aggregation-negative population of cells.

In some such methods, the method is repeated at least three times in at least three different experiments, and a gene is considered to exhibit synthetic lethality with tau protein aggregates (or is expected to exhibit synthetic lethality with tau protein aggregates) if it is considered to exhibit synthetic lethality with tau protein aggregates in more than about 50% of the at least three different experiments.

In some such methods, the time course in step (c) is more than about 2 weeks, wherein the plurality of time points in step (c) comprises about six time points, wherein there is between about 3 to about 4 days between each time point in step (c), wherein a guide RNA is considered depleted in step (c) if the abundance of the guide RNA at each time point after the second time point is less than or equal to the abundance of the time point two time points prior, and wherein a gene is considered to exhibit synthetic lethality with tau protein aggregates in step (c) (or is expected to exhibit synthetic lethality with tau protein aggregates) if more than about 30% of the guide RNAs in the library that target the gene are depleted in the aggregation-positive population of cells but not in the aggregation-negative population of cells.

In another aspect, provided are Cas-tau biosensor cells and population of such cells such as a population of one or more cells comprising a Cas protein, a first tau repeat domain linked to a first reporter, and a second tau repeat domain linked to a second reporter.

In some such cells, the first tau repeat domain and/or the second tau repeat domain is a human tau repeat domain. In some such cells, the first tau repeat domain and/or the second tau repeat domain comprises a pro-aggregation mutation. Optionally, the first tau repeat domain and/or the second tau repeat domain comprises a tau P301S mutation. In some such cells, the first tau repeat domain and/or the second tau repeat domain comprises a tau four-repeat domain. In some such cells, the first tau repeat domain and/or the second tau repeat domain comprises SEQ ID NO: 11. In some such cells, the first tau repeat domain and the second tau repeat domain are the same. In some such cells, the first tau repeat domain and the second tau repeat domain are the same and each comprises tau four-repeat domain comprising a tau P301S mutation.

In some such cells, the first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such cells, the Cas protein is a Cas9 protein. Optionally, the Cas protein is *Streptococcus pyogenes* Cas9. Optionally, the Cas protein comprises SEQ ID NO: 21. Optionally, the Cas protein is encoded by a coding sequence comprising the sequence set forth in SEQ ID NO: 22.

In some such cells, the Cas protein, the first tau repeat domain linked to the first reporter, and the second tau repeat domain linked to the second reporter are stably expressed in the cell. In some such cells, nucleic acids encoding the Cas protein, the first tau repeat domain linked to the first reporter, and the second tau repeat domain linked to the second reporter are genomically integrated in the cell.

Some such cells are eukaryotic cells. Optionally, the cells are mammalian cells. Optionally, the cells are human cells. Optionally, the cells are HEK293T cells. Optionally, the cells are in vitro.

In some such cells, the first tau repeat domain linked to the first reporter and the second tau repeat domain linked to the second reporter are not stably present in an aggregated state. In some such cells, the first tau repeat domain linked to the first reporter and the second tau repeat domain linked to the second reporter stably present in an aggregated state.

In another aspect, provided are SAM-tau biosensor cells and population of such cells such as a population of one or more cells comprising a chimeric Cas protein comprising a nuclease-inactive Cas protein (i.e., catalytically inactive Cas protein) fused to one or more transcriptional activation domains, a chimeric adaptor protein comprising an adaptor protein fused to one or more transcriptional activation domains, a first tau repeat domain linked to a first reporter, and a second tau repeat domain linked to a second reporter.

In some such cells, the first tau repeat domain and/or the second tau repeat domain is a human tau repeat domain. In some such cells, the first tau repeat domain and/or the second tau repeat domain comprises a pro-aggregation mutation. Optionally, the first tau repeat domain and/or the second tau repeat domain comprises a tau P301S mutation. In some such cells, the first tau repeat domain and/or the second tau repeat domain comprises a tau four-repeat domain. In some such cells, the first tau repeat domain and/or the second tau repeat domain comprises SEQ ID NO: 11. In some such cells, the first tau repeat domain and the second tau repeat domain are the same. In some such cells, the first tau repeat domain and the second tau repeat domain are the same and each comprises tau four-repeat domain comprising a tau P301S mutation.

In some such cells, the first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such cells, the Cas protein is a Cas9 protein. Optionally, the Cas protein is *Streptococcus pyogenes* Cas9. In some such cells, the chimeric Cas protein comprises the nuclease-inactive Cas protein fused to a VP64 transcriptional activation domain, optionally wherein the chimeric Cas protein comprises from N-terminus to C-terminus: the nuclease-inactive Cas protein; a nuclear localization signal; and the VP64 transcriptional activator domain. In some such cells, the adaptor protein is an MS2 coat protein, and the one or more transcriptional activation domains in the chimeric adaptor protein comprise a p65 transcriptional activation domain and an HSF1 transcriptional activation domain, optionally wherein the chimeric adaptor protein comprises from N-terminus to C-terminus: the MS2 coat protein; a nuclear localization signal; the p65 transcriptional activation domain; and the HSF1 transcriptional activation domain. In some such cells, the chimeric Cas protein comprises SEQ ID NO: 36, optionally wherein the chimeric Cas protein is encoded by a coding sequence comprising the sequence set forth in SEQ ID NO: 38. In some such cells, the chimeric adaptor protein comprises SEQ ID NO: 37, optionally wherein the chimeric adaptor protein is encoded by a coding sequence comprising the sequence set forth in SEQ ID NO: 39.

In some such cells, the chimeric Cas protein, the chimeric adaptor protein, the first tau repeat domain linked to the first reporter, and the second tau repeat domain linked to the second reporter are stably expressed in the cell. In some such cells, nucleic acids encoding the chimeric Cas protein, the chimeric adaptor protein, the first tau repeat domain linked to the first reporter, and the second tau repeat domain linked to the second reporter are genomically integrated in the cell.

Some such cells are eukaryotic cells. Optionally, the cells are mammalian cells. Optionally, the cells are human cells. Optionally, the cells are HEK293T cells. Optionally, the cells are in vitro.

In some such cells, the first tau repeat domain linked to the first reporter and the second tau repeat domain linked to the second reporter are not stably present in an aggregated state. In some such cells, the first tau repeat domain linked to the first reporter and the second tau repeat domain linked to the second reporter stably present in an aggregated state.

In another aspect, provided are in vitro cultures comprising any of the above populations of cells or any of the cells disclosed herein and a culture medium.

BRIEF DESCRIPTION OF THE FIGURES

FIG. 1 (not to scale) shows a schematic of tau isoform 2N4R. The tau biosensor lines include only tau4RD-YFP and tau4RD-CFP as transgenes, not the full 2N4R.

FIG. 2 shows a schematic of how aggregate formation is monitored by fluorescence resonance energy transfer (FRET) in Tau biosensor cell lines. The Tau$^{4RD}$-CFP protein is excited by violet light and emits blue light. The Tau$^{4RD}$-YFP fusion protein is excited by blue light and emits yellow light. If there is no aggregation, excitation by violet light will not lead to FRET. If there is Tau aggregation, excitation by violet light will lead to FRET and yellow light emission.

FIG. 15A) and three candidate synthetic lethal genes (Target Genes 1, 5, and 6 (TG1, TG5, and TG6); FIG. 15B).

DEFINITIONS

Figure 3A:
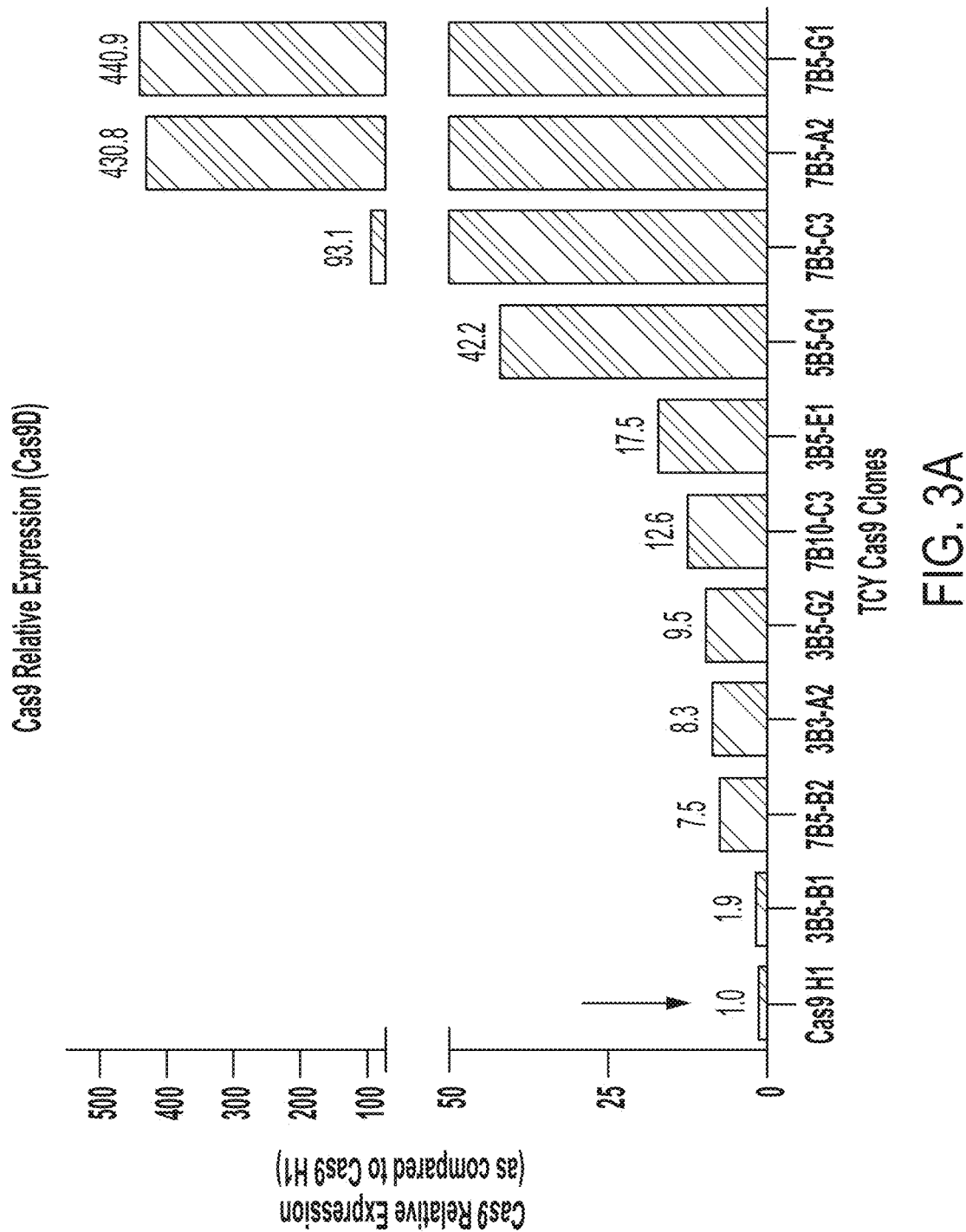
FIG. 3A shows relative Cas9 mRNA expression in Tau$^{4RD}$-CFP/Tau$^{4RD}$-YFP (TCY) biosensor cell clones transduced with lentiviral Cas9 expression constructs relative to clone Cas9H1, which is a control underperforming Cas9-expression TCY clone that was previously isolated.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells either ex vivo or in vivo. Numerous forms of viral vectors are known.

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or organism. For example, an endogenous MAPT sequence of a cell or organism refers to a native MAPT sequence that naturally occurs at the MAPT locus in the cell or organism.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

The term "locus" refers to a specific location of a gene (or significant sequence), DNA sequence, polypeptide-encoding sequence, or position on a chromosome of the genome of an organism. For example, a "MAPT locus" may refer to the specific location of a MAPT gene, MAPT DNA sequence, microtubule-associated-protein-tau-encoding sequence, or MAPT position on a chromosome of the genome of an organism that has been identified as to where such a sequence resides. A "MAPT locus" may comprise a regulatory element of a MAPT gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a human cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences refers to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

TABLE 1

Amino Acid Categorizations.

| Alanine | Ala | A | Nonpolar | Neutral | 1.8 |
|---------|-----|---|----------|---------|-----|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreen1), yellow fluorescent proteins (e.g., YFP, eYFP, Citrine, Venus, YPet, PhiYFP, and ZsYellow1), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p \leq 0.05$.

DETAILED DESCRIPTION

I. Overview

Cas-protein-ready tau biosensor cells and methods of making and using such cells to screen for genetic vulnerability associated with tau aggregation are provided. CRISPR/Cas synergistic activation mediator (SAM)-ready tau biosensor cells and methods of making and using such cells to screen for genetic vulnerability associated with tau aggregation are also provided.

To identify genes and pathways that exhibit synthetic lethality with disease-associated protein aggregates, a platform was developed for performing genome-wide screens with CRISPR nuclease (CRISPRn) sgRNA libraries. The platform identifies genes that, when disrupted, cause cell death specifically in the context of abnormal protein aggregation. To identify further genes and pathways that exhibit synthetic lethality with disease-associated protein aggregates, a platform was developed for performing genome-wide screens with CRISPR activation (CRISPRa) sgRNA libraries. The platform identifies genes that, when activated, cause cell death specifically in the context of abnormal protein aggregation. The identification of such genes may elucidate the mechanisms of aggregate-associated neurotoxicity, and genetic pathways that promote death of neurons in the context of neurodegenerative disease.

The screens employ a tau biosensor cell line (e.g., human cell line, or HEK293T) consisting of cells stably expressing tau repeat domain (e.g., tau four-repeat domain, tau_4RD) with a pathogenic mutation (e.g., the P301S pathogenic mutation), linked to unique reporters that can act together as an intracellular biosensor that produces a detectable signal when aggregated. In one non-limiting example, the cell lines contain two transgenes stably expressing disease-associated protein variants fused to the fluorescent protein CFP (e.g., eCFP) or the fluorescent protein YFP (e.g., eYFP): $tau^{4RD}$-CFP/$tau^{4RD}$-YFP (TCY), wherein the tau repeat domain (4RD) comprises the P301S pathogenic mutation. In these biosensor lines, tau-CFP/tau-YFP protein aggregation produces a fluorescence resonance energy transfer (FRET) signal, the result of a transfer of fluorescent energy from donor CFP to acceptor YFP. The term CFP (cyan fluorescent protein) when used herein includes eCFP (enhanced cyan fluorescent protein), and the term YFP (yellow fluorescent protein) when used herein includes eYFP (enhanced yellow fluorescent protein). FRET-positive cells, which contain tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal. Aggregate-containing cells can be isolated by FACS. Stably propagating aggregate-containing cell lines, Agg[+], can be isolated by clonal serial dilution of Agg[−] cell lines.

Several modifications were made to this tau biosensor cell line to make it useful for genetic screening using CRISPRn libraries. First, these tau biosensor cells were modified by introducing a Cas-expressing transgene (e.g., Cas9 or SpCas9) for use in the CRISPRn screens. Second, subclones of these Cas-expressing tau biosensor lines were derived in which tau protein is stably present in either a non-aggregated (the default state) (Agg[−]) or an aggregated state (Agg[+]).

These cell lines were used to develop a method of screening in which Cas-expressing tau biosensor cells, either with aggregates (Agg[+]) or without aggregates (Agg[−]), were transduced with a CRISPR guide RNA library to introduce knock-out mutations at each target gene. Screening was then done to identify not only essential genes, consisting of those genes whose targeting sgRNAs become depleted over time in both the Agg[+] and Agg[−] cell lines, but also synthetic lethal genes, consisting of genes whose targeting sgRNAs become depleted over time preferentially in the Agg[+] as compared to the Agg[−] cell lines. Depletion profiles were assessed using a newly defined time course analysis, in which guide RNAs with a consistent pattern of decreasing reads from the earliest time point to the final time point were considered to be depleted. This is a novel analytical approach to evaluating guide RNA depletion, as compared to the more conventional approach of simply comparing reads of the endpoint cell collection to the first passage.

Likewise, several modifications were made to this tau biosensor cell line to make it useful for genetic screening using CRISPRa libraries (e.g., for use with a CRISPR/Cas synergistic activation mediator (SAM) system). In an exemplary SAM system, several activation domains interact to cause a greater transcriptional activation than could be induced by any one factor alone. For example, an exemplary SAM system comprises a chimeric Cas protein comprising a nuclease-inactive Cas protein fused to one or more transcriptional activation domains (e.g., VP64) and a chimeric adaptor protein comprising an adaptor protein (e.g., MS2 coat protein (MCP)) fused to one or more transcriptional activation domains (e.g., fused to p65 and HSF1). The MCP naturally binds to MS2 stem loops. In an exemplary SAM system, MCP interacts MS2 stem loops engineered into the CRISPR-associated sgRNA and thereby shuttles the bound transcription factors to the appropriate genomic location.

First, these tau biosensor cells were modified by introducing one or more transgenes expressing the chimeric Cas protein comprising the nuclease-inactive Cas protein fused to one or more transcriptional activation domains (e.g., VP64) and the chimeric adaptor protein comprising the adaptor protein (e.g., MS2 coat protein (MCP)) fused to one or more transcriptional activation domains (e.g., fused to p65 and HSF1). Although SAM systems are described herein, other CRISPRa systems such as a nuclease-inactive Cas protein fused to one or more transcriptional activation domains, wherein such systems do not also include a chimeric adaptor protein, can also be used. In such cases, the tau biosensor cells would be modified by introducing a transgene expressing the chimeric Cas protein.

Second, subclones of these SAM-expressing (i.e., chimeric-Cas-expressing and chimeric-adaptor-expressing) tau biosensor lines were derived in which tau protein is stably present in either a non-aggregated (the default state) (Agg[−]) or an aggregated state (Agg[+]).

These cell lines were used to develop a method of screening in which SAM-expressing tau biosensor cells, either with aggregates (Agg[+]) or without aggregates (Agg[−]), were transduced with a CRISPRa guide RNA library to transcriptionally activate each target gene. Screening was then done to identify gene that when activated have a synthetic lethal effect. Specifically, sgRNAs that are depleted specifically in the Agg[+] cell line, while not or less-depleted in the Agg[−] cell line, may indicate a synthetic lethal effect, in which the activation of a specific target gene combines with the presence of Tau aggregates in the cell to induce cell death. Depletion profiles were assessed using a newly defined time course analysis, in which guide RNAs with a consistent pattern of decreasing reads from the earliest time point to the final time point were considered to be depleted. This is a novel analytical approach to evaluating guide RNA depletion, as compared to the more conventional approach of simply comparing reads of the endpoint cell collection to the first passage. These synthetic lethal genes are of interest as potential modifiers of tau-associated cell toxicity.

II. Cas/Tau Biosensor and SAM/Tau Biosensor Cell Lines and Methods of Generating A. Cas/Tau Biosensor Cells and SAM/Tau Biosensor Cells Disclosed herein are cells not only expressing a first tau repeat domain (e.g., comprising the tau microtubule binding domain (MBD)) linked to a first reporter and a second tau repeat domain linked to a second reporter, but also expressing a Cas protein, such as Cas9. Also disclosed herein are cells not only expressing a first tau repeat domain (e.g., comprising the tau microtubule binding domain (MBD)) linked to a first reporter and a second tau repeat domain linked to a second reporter, but also expressing a chimeric Cas protein comprising a nuclease-inactive Cas protein fused to one or more transcriptional activation domains and a chimeric adaptor protein comprising an adaptor protein fused to one or more transcriptional activation domains. The first tau repeat domain linked to the first reporter can be stably expressed, and the second tau repeat domain linked to the second reporter can be stably expressed. For example, DNA encoding the first tau repeat domain linked to the first reporter can be genomically integrated, and DNA encoding the second tau repeat domain linked to the second reporter can be genomically integrated. Similarly, the Cas protein can be stably expressed in the Cas/tau biosensor cells. For example, DNA encoding the Cas protein can be genomically integrated. Likewise, the chimeric Cas protein and/or the chimeric adaptor protein can be stably expressed in the SAM/tau biosensor cells. For example, DNA encoding the chimeric Cas protein can be genomically integrated and/or DNA encoding the chimeric adaptor protein can be genomically integrated.

1. Tau and Tau Repeat Domains Linked to Reporters

Microtubule-associated protein tau is a protein that promotes microtubule assembly and stability and is predominantly expressed in neurons. Tau has a role in stabilizing neuronal microtubules and thus in promoting axonal outgrowth. In Alzheimer disease (AD) and a family of related neurodegenerative diseases called tauopathies, tau protein is abnormally hyperphosphorylated and aggregated into bundles of filaments (paired helical filaments), which manifest as neurofibrillary tangles. Tauopathies are a group of heterogeneous neurodegenerative conditions characterized by deposition of abnormal tau in the brain.

The tau repeat domain can be from a tau protein from any animal or mammal, such as human, mouse, or rat. In one specific example, the tau repeat domain is from a human tau protein. An exemplary human tau protein is assigned UniProt accession number P10636. The tau proteins are the products of alternate splicing from a single gene that in humans is designated MAPT (microtubule-associated protein tau). The tau repeat domain carries the sequence motifs responsible for aggregation (i.e., it is the aggregation-prone domain from tau). Depending on splicing, the repeat domain of the tau protein has either three or four repeat regions that constitute the aggregation-prone core of the protein, which is often termed the repeat domain (RD). Specifically, the repeat domain of tau represents the core of the microtubule binding region and harbors the hexapeptide motifs in R2 and R3 that are responsible for Tau aggregation. In the human brain, there are six tau isoforms ranging from 352 to 441 amino acids in length. These isoforms vary at the carboxyl terminal according to the presence of either three repeat or four repeat domains (R1-R4), in addition to the presence or absence of one or two insert domains at the amino-terminus. The repeat domains, located at the carboxyl-terminal half of tau, are believed to be important for microtubule binding as well as for the pathological aggregation of tau into paired helical filaments (PHFs), which are the core constituents of the neurofibrillary tangles found in tauopathies. Exemplary sequences for the four repeat domains (R1-R4) are provided in SEQ ID NOS: 1-4, respectively. Exemplary coding sequences for the four repeat domains (R1-R4) are provided in SEQ ID NOS: 5-8. An exemplary sequence for the Tau four-repeat domain is provided in SEQ ID NO: 9. An exemplary coding sequence for the Tau four-repeat domain is provided in SEQ ID NO: 10. An exemplary sequence for the Tau four-repeat domain with the P301S mutation is provided in SEQ ID NO: 11. An exemplary coding sequence for the Tau four-repeat domain with the P301S mutation is provided in SEQ ID NO: 12.

The tau repeat domain used in the Cas/tau biosensor cells or the SAM/tau biosensor cells can comprise the tau microtubule binding domain (MBD). The tau repeat domain used in the Cas/tau biosensor cells or the SAM/tau biosensor cells can comprise one or more or all of the four repeat domains (R1-R4). For example, the tau repeat domain can comprise, consist essentially of, or consist of one or more or all of SEQ ID NOS: 1, 2, 3, and 4, or sequences at least about 90%, 91%, 92%, 93%, 94%, 95%, 96%, 97%, 98%, or 99% identical to SEQ ID NOS: 1, 2, 3, and 4. In one specific example, the tau repeat domain is the tau four-repeat domain (R1-R4) found in several tau isoforms. For example, the tau repeat domain can comprise, consist essentially of, or consist of SEQ ID NO: 9 or SEQ ID NO: 11 or a sequence at least about 90%, 91%, 92%, 93%, 94%, 95%, 96%, 97%, 98%, or 99% identical to SEQ ID NO: 9 or SEQ ID NO: 11. In one specific example, the nucleic acid encoding the tau repeat domain can comprise, consist essentially of, or consist of SEQ ID NO: 12 or a sequence at least about 90%, 91%, 92%, 93%, 94%, 95%, 96%, 97%, 98%, or 99% identical to SEQ ID NO: 12, optionally wherein the nucleic acid encodes a protein comprising, consisting essentially of, or consisting of SEQ ID NO: 11. In another specific example, the nucleic acid encoding the second tau repeat domain linked to the second reporter can comprise, consist essentially of, or consist of SEQ ID NO: 10 or a sequence at least about 90%, 91%, 92%, 93%, 94%, 95%, 96%, 97%, 98%, or 99% identical to SEQ ID NO: 10, optionally wherein the nucleic acid encodes a protein comprising, consisting essentially of, or consisting of SEQ ID NO: 9. The first and second tau repeat domains in the cells disclosed herein can be the same, similar, or different.

One or both of the first tau repeat domain linked to the first reporter and the second tau repeat domain linked to the second reporter can be stably expressed in the cells. For example, nucleic acids encoding one or both of the first tau repeat domain linked to the first reporter and the second tau repeat domain linked to the second reporter can be genomically integrated in the population of cells and operably linked to promoters active in the cell.

The tau repeat domains used in the cells disclosed herein can also comprise a tau pathogenic mutation, such as a pro-aggregation mutation. Such a mutation can be, for example, a mutation that is associated with (e.g., segregates with) or causes a tauopathy. As one example, the mutation can be an aggregation-sensitizing mutation that sensitizes tau to seeding but does not result in tau readily aggregating on its own. For example, the mutation can be the disease-associated P301S mutation. By P301S mutation is meant the human tau P301S mutation or a corresponding mutation in another tau protein when optimally aligned with the human tau protein. The P301S mutation in tau exhibits high sensitivity to seeding, but it does not readily aggregate on its own. Thus, although at baseline tau reporter proteins comprising the P301S mutation exist in a stable, soluble form within the cell, exposure to exogenous tau seeds leads to tau reporter protein aggregation. Other tau mutations include, for example, K280del, P301L, V337M, P301L/V337M, and K280del/I227P/I308P.

The first tau repeat domain can be linked to the first reporter and the second tau repeat domain can be linked to the second reporter by any means. For example, the reporter can be fused to the tau repeat domain (e.g., as part of a fusion protein).

The first reporter and second reporter can be and pair of unique reporters that can act together as an intracellular biosensor that produces a detectable signal when the first and second proteins are aggregated. As one example, the reporters can be fluorescent proteins, and fluorescence resonance energy transfer (FRET) can be used to measure protein aggregation. Specifically, the first and second reporters can be a FRET pair. Examples of FRET pairs (donor and acceptor fluorophores) are well known. See, e.g., Bajar et al. (2016) *Sensors* (*Basel*) 16(9):1488, herein incorporated by reference in its entirety for all purposes. Typical fluorescence microscopy techniques rely upon the absorption by a fluorophore of light at one wavelength (excitation), followed by the subsequent emission of secondary fluorescence at a longer wavelength. The mechanism of fluorescence resonance energy transfer involves a donor fluorophore in an excited electronic state, which may transfer its excitation energy to a nearby acceptor chromophore in a non-radiative fashion through long-range dipole-dipole interactions. For example, the FRET energy donor may be the first reporter, and the FRET energy acceptor may be the second reporter. Alternatively, the FRET energy donor may be the second reporter, and the FRET energy acceptor may be the first reporter. In a specific example, the first and second reporters are CFP and YFP. Exemplary protein and coding sequences for CFP are provided, e.g., in SEQ ID NOS: 13 and 14, respectively. Exemplary protein and coding sequences for YFP are provided, e.g., in SEQ ID NOS: 15 and 16, respectively. As a specific example, the CFP can comprise, consist essentially of, or consist of SEQ ID NO: 13 or a sequence at least about 90%, 91%, 92%, 93%, 94%, 95%, 96%, 97%, 98%, or 99% identical to SEQ ID NO: 13. As another specific example, the YFP can comprise, consist essentially of, or consist of SEQ ID NO: 15 or a sequence at least about 90%, 91%, 92%, 93%, 94%, 95%, 96%, 97%, 98%, or 99% identical to SEQ ID NO: 15.

As another example, a protein fragment complementation strategy can be used to detect aggregation. For example, a split-luciferase can be used to produce bioluminescence from a substrate, and the first and second reporters can be amino- (NLuc) and carboxy- (CLuc) terminal fragments of the luciferase. Examples of luciferase include *Renilla*, firefly, click beetle, and Metridia luciferase.

In one non-limiting example, the biosensor cells disclosed herein contain two transgenes stably expressing disease-associated tau protein variants fused to the fluorescent protein CFP or the fluorescent protein YFP, respectively (tau$^{4RD}$-CFP/tau$^{4RD}$-YFP (TCY)), wherein the tau four repeat domain (4RD) comprises the P301S pathogenic mutation. In these biosensor lines, tau-CFP/tau-YFP protein aggregation produces a FRET signal, the result of a transfer of fluorescent energy from donor CFP to acceptor YFP. FRET-positive cells, which contain tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal.

The Cas/tau biosensor cells disclosed herein can be aggregation-positive (Agg[+]) cells in which the tau repeat domain stably presents in an aggregated state, meaning that the tau repeat domain aggregates stably persist in all cells with growth and multiple passages over time. Alternatively, the Cas/tau biosensor cells disclosed herein can be aggregation-negative (Agg[−]).

2. Cas Proteins and Chimeric Cas Proteins

The Cas/tau biosensor cells disclosed herein also comprise nucleic acids (DNA or RNA) encoding Cas proteins. Optionally, the Cas protein is stably expressed. Optionally, the cells comprise a genomically integrated Cas coding sequence. Likewise, the SAM/tau biosensor cells disclosed herein also comprise nucleic acids (DNA or RNA) encoding chimeric Cas proteins comprising a nuclease-inactive Cas protein fused to one or more transcriptional activation domains (e.g., VP64). Optionally, the chimeric Cas protein is stably expressed. Optionally, the cells comprise a genomically integrated chimeric Cas coding sequence.

Cas proteins are part of Clustered Regularly Interspersed Short Palindromic Repeats (CRISPR)/CRISPR-associated (Cas) systems. CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). The methods and compositions disclosed herein can employ CRISPR/Cas systems by utilizing CRISPR complexes (comprising a guide RNA (gRNA) complexed with a Cas protein) for site-directed binding or cleavage of nucleic acids.

CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

Cas proteins generally comprise at least one RNA recognition or binding domain that can interact with guide RNAs. Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1

(CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp *Arthrospira maxima, Arthrospira platensis, Arthrospira* sp., *Lyngbya* sp., *Microcoleus chthonoplastes, Oscillatoria* sp *Petrotoga mobilis, Thermosipho africanus, Acaryochloris marina, Neisseria meningitidis*, or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Exemplary SpCas9 protein and coding sequence are set forth in SEQ ID NOS: 21 and 22, respectively. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9. Cas9 from *Neisseria meningitidis* (Nme2Cas9) is another exemplary Cas9 protein. See, e.g., Edraki et al. (2019) *Mol. Cell* 73(4):714-726, herein incorporated by reference in its entirety for all purposes. Cas9 proteins from *Streptococcus thermophilus* (e.g., *Streptococcus thermophilus* LMD-9 Cas9 encoded by the CRISPR1 locus (St1Cas9) or *Streptococcus thermophilus* Cas9 from the CRISPR3 locus (St3Cas9)) are other exemplary Cas9 proteins. Cas9 from *Francisella novicida* (FnCas9) or the RHA *Francisella novicida* Cas9 variant that recognizes an alternative PAM (E1369R/E1449H/R1556A substitutions) are other exemplary Cas9 proteins. These and other exemplary Cas9 proteins are reviewed, e.g., in Cebrian-Serrano and Davies (2017) *Mamm. Genome* 28(7):247-261, herein incorporated by reference in its entirety for all purposes.

As one example, the Cas protein can be a Cas9 protein. For example, the Cas9 protein can be a *Streptococcus pyogenes* Cas9 protein. As one specific example, the Cas protein can comprise, consist essentially of, or consist of SEQ ID NO: 21 or a sequence at least about 90%, 91%, 92%, 93%, 94%, 95%, 96%, 97%, 98%, or 99% identical to SEQ ID NO: 21. As another specific example, a chimeric Cas protein comprising a nuclease-inactive Cas protein and one or more transcriptional activation domains can comprise, consist essentially of, or consist of SEQ ID NO: 36 or a sequence at least about 90%, 91%, 92%, 93%, 94%, 95%, 96%, 97%, 98%, or 99% identical to SEQ ID NO: 36.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida*, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain double-strand-break-inducing activity. Assays for double-strand-break-inducing activity are known and generally measure the overall activity and specificity of the Cas protein on DNA substrates containing the cleavage site.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) Nature 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) Science 351(6268):84-88, herein incorporated by reference in its entirety for all purposes. Other SpCas9 variants include K855A and K810A/K1003A/R1060A. These and other modified Cas proteins are reviewed, e.g., in Cebrian-Serrano and Davies (2017) Mamm. Genome 28(7):247-261, herein incorporated by reference in its entirety for all purposes. Another example of a modified Cas9 protein is xCas9, which is a SpCas9 variant that can recognize an expanded range of PAM sequences. See, e.g., Hu et al. (2018) *Nature* 556:57-63, herein incorporated by reference in its entirety for all purposes.

Cas proteins can be modified to increase or decrease one or more of nucleic acid binding affinity, nucleic acid binding specificity, and enzymatic activity. Cas proteins can also be modified to change any other activity or property of the protein, such as stability. For example, a Cas protein can be truncated to remove domains that are not essential for the function of the protein or to optimize (e.g., enhance or reduce) the activity of or a property of the Cas protein. As another example, one or more nuclease domains of the Cas protein can be modified, deleted, or inactivated (e.g., for use in the SAM/tau biosensor cells comprising a nuclease-inactive Cas protein).

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Res.* 39(21):9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of xCas9 are the same as those described above for SpCas9. Examples of inactivating mutations in the catalytic domains of *Staphylococcus aureus* Cas9 proteins are also known. For example, the *Staphyloccocus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes. Examples of inactivating mutations in the catalytic domains of Nme2Cas9 are also known (e.g., combination of D16A and H588A). Examples of inactivating mutations in the catalytic domains of St1Cas9 are also known (e.g., combination of D9A, D598A, H599A, and N622A). Examples of inactivating mutations in the catalytic domains of St3Cas9 are also known (e.g., combination of D10A and N870A). Examples of inactivating mutations in the catalytic domains of CjCas9 are also known (e.g., combination of D8A and H559A). Examples of inactivating mutations in the catalytic domains of FnCas9 and RHA FnCas9 are also known (e.g., N995A).

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), *Lachnospiraceae bacterium* ND2006 (LbCpf1), and *Moraxella* bovoculi 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain, an epigenetic modification domain, a transcriptional activation domain, or a transcriptional repressor domain. See WO 2014/089290, herein incorporated by reference in its entirety for all purposes. For example, Cas proteins can be operably linked or fused to a transcriptional activation domain for use in the SAM/tau biosensor cells. Examples of transcriptional activation domains include a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, and an NFAT (nuclear factor of activated T-cells) activation domain. Other examples include activation domains from Oct1, Oct-2A, SP1, AP-2, CTF1, P300, CBP, PCAF, SRC1, PvALF, ERF-2, OsGAI, HALF-1, C1, AP1, ARF-5, ARF-6, ARF-7, ARF-8, CPRF1, CPRF4, MYC-RP/GP, TRAB1PC4, and HSF1. See, e.g., US 2016/0237456, EP3045537, and WO 2011/146121, each of which is incorporated by reference in its entirety for all purposes. In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) *Nature* 517(7536):583-588, herein incorporated by reference in its entirety for all purposes. Examples of transcriptional repressor domains include inducible cAMP early repressor (ICER) domains, Kruppel-associated box A (KRAB-A) repressor domains, YY1 glycine rich repressor domains, Sp1-like repressors, E(spl) repressors, IκB repressor, and MeCP2. Other examples include transcriptional repressor domains from A/B, KOX, TGF-beta-inducible early gene (TIEG), v-erbA, SID, SID4X, MBD2, MBD3, DNMT1, DNMG3A, DNMT3B, Rb, ROM2, See, e.g., EP3045537 and WO 2011/146121, each of which is incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

Cas proteins can also be operably linked to heterologous polypeptides as fusion proteins. As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalama1, GFPuv, Sapphire, T-sapphire), cyan fluorescent proteins (e.g., eCFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin.

Cas proteins can be provided in any form. For example, a Cas protein can be provided in the form of a protein. For example, a Cas protein can be provided as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. For example, the nucleic acid encoding the Cas protein can be codon optimized for expression in a human cell. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of a cell and operably linked to a promoter active in the cell. In one specific example, the nucleic acid encoding the Cas protein can comprise, consist essentially of, or consist of SEQ ID NO: 22 or a sequence at least about 90%, 91%, 92%, 93%, 94%, 95%, 96%, 97%, 98%, or 99% identical to SEQ ID NO: 22, optionally wherein the nucleic acid encodes a protein comprising, consisting essentially of, or consisting of SEQ ID NO: 21. In another specific example, the nucleic acid encoding a chimeric Cas protein comprising a nuclease-inactive Cas protein and one or more transcriptional activation domains can comprise, consist essentially of, or consist of SEQ ID NO: 38 or a sequence at least about 90%, 91%, 92%, 93%, 94%, 95%, 96%, 97%, 98%, or 99% identical to SEQ ID NO: 38, optionally wherein the nucleic acid encodes a protein comprising, consisting essentially of, or consisting of SEQ ID NO: 36. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters.

3. Chimeric Adaptor Proteins

The SAM/tau biosensor cells disclosed herein can comprise not only nucleic acids (DNA or RNA) encoding a chimeric Cas protein comprising a nuclease-inactive Cas protein fused to one or more transcriptional activation domains (e.g., VP64) but optionally also nucleic acids (DNA or RNA) encoding a chimeric adaptor protein comprising an adaptor protein (e.g., MS2 coat protein (MCP)) fused to one or more transcriptional activation domains (e.g., fused to p65 and HSF1). Optionally, the chimeric Cas protein and/or the chimeric adaptor protein is stably expressed. Optionally, the cells comprise a genomically integrated chimeric Cas protein coding sequence and/or a genomically integrated chimeric adaptor protein coding sequence.

Such chimeric adaptor proteins comprise: (a) an adaptor (i.e., adaptor domain or adaptor protein) that specifically binds to an adaptor-binding element within a guide RNA; and (b) one or more heterologous transcriptional activation domains. For example, such fusion proteins can comprise 1, 2, 3, 4, 5, or more transcriptional activation domains (e.g., two or more heterologous transcriptional activation domains or three or more heterologous transcriptional activation domains). In one example, such chimeric adaptor proteins can comprise: (a) an adaptor (i.e., an adaptor domain or adaptor protein) that specifically binds to an adaptor-binding element in a guide RNA; and (b) two or more transcriptional activation domains. For example, the chimeric adaptor protein can comprise: (a) an MS2 coat protein adaptor that specifically binds to one or more MS2 aptamers in a guide RNA (e.g., two MS2 aptamers in separate locations in a guide RNA); and (b) one or more (e.g., two or more transcriptional activation domains). For example, the two transcriptional activation domains can be p65 and HSF1 transcriptional activation domains or functional fragments or variants thereof. However, chimeric adaptor proteins in which the transcriptional activation domains comprise other transcriptional activation domains or functional fragments or variants thereof are also provided.

The one or more transcriptional activation domains can be fused directly to the adaptor. Alternatively, the one or more transcriptional activation domains can be linked to the adaptor via a linker or a combination of linkers or via one or more additional domains. Likewise, if two or more transcriptional activation domains are present, they can be fused directly to each other or can be linked to each other via a linker or a combination of linkers or via one or more additional domains. Linkers that can be used in these fusion proteins can include any sequence that does not interfere with the function of the fusion proteins. Exemplary linkers are short (e.g., 2-20 amino acids) and are typically flexible (e.g., comprising amino acids with a high degree of freedom such as glycine, alanine, and serine).

The one or more transcriptional activation domains and the adaptor can be in any order within the chimeric adaptor protein. As one option, the one or more transcriptional activation domains can be C-terminal to the adaptor and the adaptor can be N-terminal to the one or more transcriptional activation domains. For example, the one or more transcriptional activation domains can be at the C-terminus of the chimeric adaptor protein, and the adaptor can be at the N-terminus of the chimeric adaptor protein. However, the one or more transcriptional activation domains can be C-terminal to the adaptor without being at the C-terminus of the chimeric adaptor protein (e.g., if a nuclear localization signal is at the C-terminus of the chimeric adaptor protein). Likewise, the adaptor can be N-terminal to the one or more transcriptional activation domains without being at the N-terminus of the chimeric adaptor protein (e.g., if a nuclear localization signal is at the N-terminus of the chimeric adaptor protein). As another option, the one or more transcriptional activation domains can be N-terminal to the adaptor and the adaptor can be C-terminal to the one or more transcriptional activation domains. For example, the one or more transcriptional activation domains can be at the N-terminus of the chimeric adaptor protein, and the adaptor can be at the C-terminus of the chimeric adaptor protein. As yet another option, if the chimeric adaptor protein comprises two or more transcriptional activation domains, the two or more transcriptional activation domains can flank the adaptor.

Chimeric adaptor proteins can also be operably linked or fused to additional heterologous polypeptides. The fused or linked heterologous polypeptide can be located at the N-terminus, the C-terminus, or anywhere internally within the chimeric adaptor protein. For example, a chimeric adaptor protein can further comprise a nuclear localization signal. A specific example of such a protein comprises an MS2 coat protein (adaptor) linked (either directly or via an NLS) to a p65 transcriptional activation domain C-terminal to the MS2 coat protein (MCP), and HSF1 transcriptional activation domain C-terminal to the p65 transcriptional activation domain. Such a protein can comprise from N-terminus to C-terminus: an MCP; a nuclear localization signal; a p65 transcriptional activation domain; and an HSF1 transcriptional activation domain. For example, a chimeric adaptor protein can comprise, consist essentially of, or consist of an amino acid sequence at least 85%, 90%, 91%, 92%, 93%, 94%, 95%, 96%, 97%, 98%, 99%, or 100% identical to the MCP-p65-HSF1 chimeric adaptor protein sequence set forth in SEQ ID NO: 37. Likewise, a nucleic acid encoding a chimeric adaptor protein can comprise, consist essentially of, or consist of a sequence at least 85%, 90%, 91%, 92%, 93%, 94%, 95%, 96%, 97%, 98%, 99%, or 100% identical to the MCP-p65-HSF1 chimeric adaptor protein coding sequence set forth in SEQ ID NO: 39

Adaptors (i.e., adaptor domains or adaptor proteins) are nucleic-acid-binding domains (e.g., DNA-binding domains and/or RNA-binding domains) that specifically recognize and bind to distinct sequences (e.g., bind to distinct DNA and/or RNA sequences such as aptamers in a sequence-specific manner). Aptamers include nucleic acids that, through their ability to adopt a specific three-dimensional conformation, can bind to a target molecule with high affinity and specificity. Such adaptors can bind, for example, to a specific RNA sequence and secondary structure. These sequences (i.e., adaptor-binding elements) can be engineered into a guide RNA. For example, an MS2 aptamer can be engineered into a guide RNA to specifically bind an MS2 coat protein (MCP). For example, the adaptor can comprise, consist essentially of, or consist of an amino acid sequence at least 85%, 90%, 91%, 92%, 93%, 94%, 95%, 96%, 97%, 98%, 99%, or 100% identical to the MCP sequence set forth in SEQ ID NO: 40. Likewise, a nucleic acid encoding the adaptor can comprise, consist essentially of, or consist of an amino acid sequence at least 85%, 90%, 91%, 92%, 93%, 94%, 95%, 96%, 97%, 98%, 99%, or 100% identical to the MCP coding sequence set forth in SEQ ID NO: 41. Specific examples of adaptors and targets include, for example, RNA-binding protein/aptamer combinations that exist within the diversity of bacteriophage coat proteins. See, e.g., US 2019-0284572 and WO 2019/183123, each of which is herein incorporated by reference in its entirety for all purposes.

The chimeric adaptor proteins disclosed herein comprise one or more transcriptional activation domains. Such transcriptional activation domains can be naturally occurring transcriptional activation domains, can be functional fragments or functional variants of naturally occurring transcriptional activation domains, or can be engineered or synthetic transcriptional activation domains. Transcriptional activation domains that can be used include those described, for example, in US 2019-0284572 and WO 2019/183123, each of which is herein incorporated by reference in its entirety for all purposes.

4. Cell Types

The Cas/tau biosensor cells disclosed herein can be any type of cell and can be in vitro, ex vivo, or in vivo. A Cas/tau biosensor cell line or population of cells can be a monoclonal cell line or population of cells. Likewise, the SAM/tau biosensor cells disclosed herein can be any type of cell and can be in vitro, ex vivo, or in vivo. A SAM/tau biosensor cell line or population of cells can be a monoclonal cell line or population of cells. The cell can be from any source. For example, the cell can be a eukaryotic cell, an animal cell, a plant cell, or a fungal (e.g., yeast) cell. Such cells can be fish cells or bird cells, or such cells can be mammalian cells, such as human cells, non-human mammalian cells, rodent cells, mouse cells, or rat cells. Mammals include, for example, humans, non-human primates, monkeys, apes, cats dogs, horses, bulls, deer, bison, sheep, rodents (e.g., mice, rats, hamsters, guinea pigs), livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. In a specific example, the Cas/tau biosensor cells are human cells (e.g., HEK293T cells). Likewise, in a specific example, the SAM/tau biosensor cells are human cells (e.g., HEK293T cells).

The cell can be, for example, a totipotent cell or a pluripotent cell (e.g., an embryonic stem (ES) cell such as a rodent ES cell, a mouse ES cell, or a rat ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cell can also be a primary somatic cell, or a cell that is not a primary somatic cell. Somatic cells can include any cell that is not a gamete, germ cell, gametocyte, or undifferentiated stem cell. The cell can also be a primary cell. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

Such cells also include would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK293T cells), and mouse embryonic fibroblast cells (e.g., 3T3 cells). Numerous types of immortalized cells are well known. Immortalized or primary cells include cells that are typically used for culturing or for expressing recombinant genes or proteins.

The cell can also be a differentiated cell, such as a neuronal cell (e.g., a human neuronal cell).

B. Methods of Generating Cas/Tau Biosensor Cells and SAM/Tau Biosensor Cells

The Cas/tau biosensor cells disclosed herein can be generated by any known means. The first tau repeat domain linked to the first reporter, the second tau repeat domain linked to the second reporter, and the Cas protein can be introduced into the cell in any form (e.g., DNA, RNA, or protein) by any known means. Likewise, the SAM/tau biosensor cells disclosed herein can be generated by any known means. The first tau repeat domain linked to the first reporter, the second tau repeat domain linked to the second reporter, the chimeric Cas protein, and the chimeric adaptor protein can be introduced into the cell in any form (e.g., DNA, RNA, or protein) by any known means. "Introducing" includes presenting to the cell the nucleic acid or protein in such a manner that the sequence gains access to the interior of the cell. The methods provided herein do not depend on a particular method for introducing a nucleic acid or protein into the cell, only that the nucleic acid or protein gains access to the interior of a least one cell. Methods for introducing nucleic acids and proteins into various cell types are known and include, for example, stable transfection methods, transient transfection methods, and virus-mediated methods. Optionally, targeting vectors can be used.

Transfection protocols as well as protocols for introducing nucleic acids or proteins into cells may vary. Non-limiting transfection methods include chemical-based transfection methods using liposomes; nanoparticles; calcium phosphate (Graham et al. (1973) Virology 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell can also be accomplished by microinjection. Microinjection of an mRNA is preferably into the cytoplasm (e.g., to deliver mRNA directly to the translation machinery), while microinjection of a protein or a DNA encoding a protein is preferably into the nucleus. Alternatively, microinjection can be carried out by injection into both the nucleus and the cytoplasm: a needle can first be introduced into the nucleus and a first amount can be injected, and while removing the needle from the cell a second amount can be injected into the cytoplasm. Methods for carrying out microinjection are well known. See, e.g., Nagy et al. (Nagy A, Gertsenstein M, Vintersten K, Behringer R., 2003, Manipulating the Mouse Embryo. Cold Spring Harbor, N.Y.: Cold Spring Harbor Laboratory Press); Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. Methods of administering nucleic acids or proteins to a subject to modify cells in vivo are disclosed elsewhere herein.

In one example, the first tau repeat domain linked to the first reporter, the second tau repeat domain linked to the second reporter, and the Cas protein can be introduced via viral transduction such as lentiviral transduction.

Screening for cells comprising the first tau repeat domain linked to the first reporter, the second tau repeat domain linked to the second reporter, and the Cas protein can be performed by any known means.

As one example, reporter genes can be used to screen for cells that have the Cas protein, the first tau repeat domain linked to the first reporter, or the second tau repeat domain linked to the second reporter. Exemplary reporter genes include those encoding luciferase, 0-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. For example, if the first reporter and the second reporter are fluorescent proteins (e.g., CFP and YFP), cells comprising these reporters can be selected by flow cytometry to select for dual-positive cells. The dual-positive cells can then be combined to generate a polyclonal line, or monoclonal lines can be generated from single dual-positive cells.

As another example, selection markers can be used to screen for cells that have the Cas protein, the first tau repeat domain linked to the first reporter, or the second tau repeat domain linked to the second reporter. Exemplary selection markers include neomycin phosphotransferase ($neo^r$), hygromycin B phosphotransferase ($hyg^r$), puromycin-N-acetyltransferase ($puro^r$), blasticidin S deaminase ($bsr^r$), xanthine/guanine phosphoribosyl transferase (gpt), or herpes simplex virus thymidine kinase (HSV-k). Another exemplary selection marker is bleomycin resistance protein, encoded by the Sh ble gene (*Streptoalloteichus hindustanus* bleomycin gene), which confers zeocin (phleomycin D1) resistance.

Aggregation-positive (Agg[+]) cells in which the tau repeat domain stably presents in an aggregated state, meaning that the tau repeat domain aggregates stably persist in all cells with growth and multiple passages over time, can be generated, for example, by seeding with tau aggregates. For example, naïve aggregation-negative (Agg[−]) Cas/tau biosensor cells disclosed herein can be treated with recombinant fibrillized tau (e.g., recombinant fibrillized tau repeat domain) to seed the aggregation of the tau repeat domain protein stably expressed by these cells. Likewise, naïve aggregation-negative (Agg[−]) SAM/tau biosensor cells disclosed herein can be treated with recombinant fibrillized tau (e.g., recombinant fibrillized tau repeat domain) to seed the aggregation of the tau repeat domain protein stably expressed by these cells. The fibrillized tau repeat domain can be the same as, similar to, or different from the tau repeat domain stably expressed by the cells. Optionally, the recombinant fibrillized tau can be mixed with lipofectamine reagent. The seeded cells can then be serially diluted to obtain single-cell-derived clones and to identify clonal cell lines in which tau repeat domain aggregates stably persist in all cells with growth and multiple passages over time.

C. In Vitro Cultures

Also disclosed herein are in vitro cultures or compositions comprising the Cas/tau biosensor cells disclosed herein and medium for culturing those cells. Also disclosed herein are in vitro cultures or compositions comprising the SAM/tau biosensor cells disclosed herein and medium for culturing those cells. The cells can be Agg[−] cells or Agg[+] cells.

III. Guide RNA Knockout Libraries

The CRISPRn screening methods disclosed herein make use of CRISPR guide RNA (gRNA) knockout libraries such as genome-wide gRNA knockout libraries. Cas nucleases such as Cas9 can be programmed to induce double-strand breaks at specific genomic loci through gRNAs designed to target specific target sequences. Because the targeting specificity of Cas proteins is conferred by short gRNAs, pooled genome-scale functional screening is possible. Such libraries have several advantages over libraries such as shRNA libraries, which reduce protein expression by targeting mRNA. In contrast, gRNA libraries achieve knockout via frameshift mutations introduced in genomic coding regions of genes.

The CRISPRa screening methods disclosed herein make use of CRISPR guide RNA (gRNA) transcriptional activation libraries such as genome-wide gRNA transcriptional activation libraries. SAM systems can be programmed to activate transcription of genes at specific genomic loci through gRNAs designed to target specific target sequences. Because the targeting specificity of Cas proteins is conferred by short gRNAs, pooled genome-scale functional screening is possible.

The gRNAs in a library can target any number of genes. For example, the gRNAs can target about 50 or more genes, about 100 or more genes, about 200 or more genes, about 300 or more genes, about 400 or more genes, about 500 or more genes, about 1000 or more genes, about 2000 or more genes, about 3000 or more genes, about 4000 or more genes, about 5000 or more genes, about 10000 or more genes, or about 20000 or more genes. In some libraries, the gRNAs can be selected to target genes in a particular signaling pathway. Some libraries are genome-wide libraries.

The genome-wide libraries include one or more gRNAs (e.g., sgRNAs) targeting each gene in the genome. The genome being targeted can any type of genome. For example, the genome can be a eukaryotic genome, a mammalian genome, a non-human mammalian genome, a rodent genome, a mouse genome, a rat genome, or a human genome. In one example, the targeted genome is a human genome.

The gRNAs can target any number of sequences within each individual targeted gene. In some libraries, a plurality of target sequences are targeted on average in each of the targeted plurality of genes. For example, about 2 to about 10, about 2 to about 9, about 2 to about 8, about 2 to about 7, about 2 to about 6, about 2 to about 5, about 2 to about 4, or about 2 to about 3 unique target sequences can be targeted on average in each of the targeted plurality of genes. For example, at least about 2, at least about 3, at least about 4, at least about 5, or at least about 6 unique target sequences can be targeted on average in each of the targeted plurality of genes. As a specific example, about 6 target sequences can be targeted on average in each of the targeted plurality of genes. As another specific example, about 3 to about 6 or about 4 to about 6 target sequences are targeted on average in each of the targeted plurality of genes.

For example, the libraries can target genes with an average coverage of about 1, about 2, about 3, about 4, about 5, about 6, about 7, about 8, about 9, or about 10 gRNAs per gene. In a specific example a library can target genes with an average coverage of about 3-4 gRNAs per gene or about 6 gRNAs per gene.

The gRNAs can target any desired location in the target genes. The CRISPRn gRNAs can be designed to target coding regions of genes so that cleavage by the corresponding Cas protein will result in frameshift insertion/deletion (indel) mutations that result in a loss-of-function allele. More specifically, frameshift mutations can be achieved through targeted DNA double strand breaks and subsequent mutagenic repair via the non-homologous end joining (NHEJ) pathway, which produces indels at the site of break. The indel being introduced into the DSB is random, with some indels leading to frameshift mutations that cause premature termination of the gene.

In some CRISPRn libraries, each gRNA targets a constitutive exon if possible. In some CRISPRn libraries, each gRNA targets a 5' constitutive exon if possible. In some methods, each gRNA targets a first exon, a second exon, or a third exon (from the 5' end of the gene) if possible.

As one example, the gRNAs in the CRISPRn library can target constitutive exons. Constitutive exons are exons that are consistently conserved after splicing. Exons expressed across all tissues can be considered constitutive exons for gRNA targeting. The gRNAs in the library can target constitutive exons near the 5' end of each gene. Optionally, the first and last exons of each gene can be excluded as potential targets. Optionally, any exon containing an alternative splicing site can be excluded as potential targets. Optionally, the two earliest exons meeting the above criteria are selected as potential targets. Optionally, exons 2 and 3 are selected as potential targets (e.g., if no constitutive exons are identified). In addition, the gRNAs in the library can be selected and designed to minimize off-target effects.

In a specific example, the genome-wide CRISPRn gRNA library or libraries comprise sgRNAs targeting 5' constitutive exons of >18,000 genes in the human genome with an average coverage of ~6 sgRNAs per gene, with each target site was selected to minimize off-target modification.

The CRISPRa gRNAs can be designed to target sequences adjacent to the transcription start site of a gene. For example, the target sequence can be within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair of the transcription start site. For example, each gRNA in the CRISPRa library can target a sequence within 200 bp upstream of a transcription start site. Optionally, the target sequence is within the region 200 base pairs upstream of the transcription start site and 1 base pair downstream of the transcription start site (−200 to +1).

The gRNAs in the genome-wide library can be in any form. For example, the gRNA library can be packaged in a viral vector, such as retroviral vectors, lentiviral vectors, or adenoviral vectors. In a specific example, the gRNA library is packaged in lentiviral vectors. The vectors can further comprise reporter genes or selection markers to facilitate selection of cells that receive the vectors. Examples of such reporter genes and selection markers are disclosed elsewhere herein. As one example, the selection marker can be one that imparts resistance to a drug, such as neomycin phosphotransferase, hygromycin B phosphotransferase, puromycin-N-acetyltransferase, and blasticidin S deaminase. Another exemplary selection marker is bleomycin resistance protein, encoded by the Sh ble gene (*Streptoalloteichus hindustanus* bleomycin gene), which confers zeocin (phleomycin D1) resistance. For example, cells can be selected with a drug (e.g., puromycin) so that only cells transduced with a guide RNA construct are preserved for being used to carry out screening.

A. Guide RNAs

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO:

23). Any of the DNA-targeting segments disclosed herein can be joined to the 5' end of SEQ ID NO: 23 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of AGCAUAGCAAGUUAAAAUAAGGCUAGU-CCGUUAUCAACUUGAAAAAGUGGCACC GAGUCG-GUGCUUU (SEQ ID NO: 24). Other examples of tracrRNA sequences comprise, consist essentially of, or consist of any one of

```
                                                  (SEQ ID NO: 28)
AAACAGCAUAGCAAGUUAAAAUAAGGCUAGUCCGUUAUCAACUUGAAAAA

GUGGCACCGAGUCGGUGCUUUU, or (SEQ ID NO: 29)
GUUGGAACCAUUCAAAACAGCAUAGCAAGUUAAAAUAAGGCUAGUCCGUU

AUCAACUUGAAAAAGUGGCACCGAGUCGGUGC.
```

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment and a scaffold sequence (i.e., the protein-binding or Cas-binding sequence of the guide RNA). For example, such guide RNAs can have a 5' DNA-targeting segment joined to a 3' scaffold sequence. Exemplary scaffold sequences comprise, consist essentially of, or consist of: GUUUUAGAGC-UAGAAAUAGCAAGUUAAAAUAAGGCUAGU-CCGUUAUCAACUUGA AAAAGUGGCACCGAGUCGGUGCU (version 1; SEQ ID NO: 17); GUUGGAACCAUUCAAAACAG-CAUAGCAAGUUAAAAUAAGGCUAGU-CCGUUAUCA ACUUGAAAAAGUGGCACCGAGUCG-GUGC (version 2; SEQ ID NO: 18); GUUUUAGAGCUA-GAAAUAGCAAGUUAAAAUAAGGCUAGU-CCGUUAUCAACUUGA AAAAGUGGCACCGAGUCG-GUGC (version 3; SEQ ID NO: 19); and GUUUAAGAGCUAUGCUGGAAACAG-CAUAGCAAGUUUAAAUAAGGCUAGUCCGUU AUCAACUUGAAAAAGUGGCACCGAGUCGGUGC (version 4; SEQ ID NO: 20). Other exemplary scaffold sequences comprise, consist essentially of, or consist of:

GUUUUAGAGCUAGAAAUAGCAAGUUAAAAUAAGGCUAGUCCGUUAUCAAC

UUGAAAAAGUGGCACCGAGUCGGUGCUUUUUUU (version 5;

SEQ ID NO: 30);

GUUUUAGAGCUAGAAAUAGCAAGUUAAAAUAAGGCUAGUCCGUUAUCAAC

UUGAAAAAGUGGCACCGAGUCGGUGCUUUU (version 6;

SEQ ID NO: 31); or

GUUUAAGAGCUAUGCUGGAAACAGCAUAGCAAGUUUAAAUAAGGCUAGUC

CGUUAUCAACUUGAAAAAGUGGCACCGAGUCGGUGC (version 7;

SEQ ID NO: 32).

Guide RNAs targeting any of the guide RNA target sequences disclosed herein can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of the above scaffold sequences to form a single guide RNA (chimeric guide RNA).

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) Nature 517(7536):583-588, herein incorporated by reference in its entirety for all purposes.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs. For example, Cas mRNAs can be modified by depletion of uridine using synonymous codons.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Rep.* 22(9):2227-2235, each of which is herein incorporated by reference in its entirety for all purposes. Other possible modifications are described in more detail elsewhere herein. In a specific example, a guide RNA includes 2'-O-methyl analogs and 3' phosphorothioate internucleotide linkages at the first three 5' and 3' terminal RNA residues. Such chemical modifications can, for example, provide greater stability and protection from exonucleases to guide RNAs, allowing them to persist within cells for longer than unmodified guide RNAs. Such chemical modifications can also, for example, protect against innate intracellular immune responses that can actively degrade RNA or trigger immune cascades that lead to cell death.

In some guide RNAs (e.g., single guide RNAs), at least one loop (e.g., two loops) of the guide RNA is modified by insertion of a distinct RNA sequence that binds to one or more adaptors (i.e., adaptor proteins or domains). Such adaptor proteins can be used to further recruit one or more heterologous functional domains, such as transcriptional activation domains (e.g., for use in CRISPRa screening in the SAM/tau biosensor cells). Examples of fusion proteins comprising such adaptor proteins (i.e., chimeric adaptor proteins) are disclosed elsewhere herein. For example, an MS2-binding loop ggccAACAUGAGGAUCACCCAUGU-CUGCAGggcc (SEQ ID NO: 33) may replace nucleotides+13 to +16 and nucleotides+53 to +56 of the sgRNA scaffold (backbone) set forth in SEQ ID NO: 17 or SEQ ID NO: 19 (or SEQ ID NO: 30 or 31) or the sgRNA backbone for the S. pyogenes CRISPR/Cas9 system described in WO 2016/049258 and Konermann et al. (2015) Nature 517(7536):583-588, each of which is herein incorporated by reference in its entirety for all purposes. See also US 2019-0284572 and WO 2019/183123, each of which is herein incorporated by reference in its entirety for all purposes. The guide RNA numbering used herein refers to the nucleotide numbering in the guide RNA scaffold sequence (i.e., the sequence downstream of the DNA-targeting segment of the guide RNA). For example, the first nucleotide of the guide RNA scaffold is +1, the second nucleotide of the scaffold is +2, and so forth. Residues corresponding with nucleotides+13 to +16 in SEQ ID NO: 17 or SEQ ID NO: 19 (or SEQ ID NO: 30 or 31) are the loop sequence in the region spanning nucleotides+9 to +21 in SEQ ID NO: 17 or SEQ ID NO: 19 (or SEQ ID NO: 30 or 31), a region referred to herein as the tetraloop. Residues corresponding with nucleotides+53 to +56 in SEQ ID NO: 17 or SEQ ID NO: 19 (or SEQ ID NO: 30 or 31) are the loop sequence in the region spanning nucleotides +48 to +61 in SEQ ID NO: 17 or SEQ ID NO: 19 (or SEQ ID NO: 30 or 31), a region referred to herein as the stem loop 2. Other stem loop sequences in in SEQ ID NO: 17 or SEQ ID NO: 19 (or SEQ ID NO: 30 or 31) comprise stem loop 1 (nucleotides+33 to +41) and stem loop 3 (nucleotides+63 to +75). The resulting structure is an sgRNA scaffold in which each of the tetraloop and stem loop 2 sequences have been replaced by an MS2 binding loop. The tetraloop and stem loop 2 protrude from the Cas9 protein in such a way that adding an MS2-binding loop should not interfere with any Cas9 residues. Additionally, the proximity of the tetraloop and stem loop 2 sites to the DNA indicates that localization to these locations could result in a high degree of interaction between the DNA and any recruited protein, such as a transcriptional activator. Thus, in some sgRNAs, nucleotides corresponding to +13 to +16 and/or nucleotides corresponding to +53 to +56 of the guide RNA scaffold set forth in SEQ ID NO: 17 or SEQ ID NO: 19 (or SEQ ID NO: 30 or 31) or corresponding residues when optimally aligned with any of these scaffold/backbones are replaced by the distinct RNA sequences capable of binding to one or more adaptor proteins or domains. Alternatively or additionally, adaptor-binding sequences can be added to the 5' end or the 3' end of a guide RNA. An exemplary guide RNA scaffold comprising MS2-binding loops in the tetraloop and stem loop 2 regions can comprise, consist essentially of, or consist of the sequence set forth in SEQ ID NO: 34. An exemplary generic single guide RNA comprising MS2-binding loops in the tetraloop and stem loop 2 regions can comprise, consist essentially of, or consist of the sequence set forth in SEQ ID NO: 35.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis. For example, a guide RNA can be chemically synthesized to include 2'-O-methyl analogs and 3' phosphorothioate internucleotide linkages at the first three 5' and 3' terminal RNA residues.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein.

B. Guide RNA Target Sequences

Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

For CRISPRa and SAM systems, it can be preferable for the target sequence to be adjacent to the transcription start site of a gene. For example, the target sequence can be within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair of the transcription start site. Optionally, the target sequence is within the region 200 base pairs upstream of the transcription start site and 1 base pair downstream of the transcription start site (−200 to +1).

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-$CCN_2$-3', where N2 is any DNA nucleotide and is immediately 5' of the sequence to which the DNA-targeting segment of the guide RNA hybridizes on the complementary strand of the target DNA. In some such cases, $N_1$ and $N_2$ can be complementary and the $N_1$—$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can be A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are $GN_{19}NGG$ (SEQ ID NO: 25) or $N_{20}NGG$ (SEQ ID NO: 26). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., $GGN_{20}NGG$; SEQ ID NO: 27) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 25-27, including the 5' G or GG and the 3' GG or NGG. Yet other guide RNA target sequences plus PAMs can have between 14 and 20 nucleotides in length of SEQ ID NOS: 25-27.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-strand break. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

IV. Methods of Dropout Screening to Reveal Genetic Vulnerabilities Associated with Tau Aggregation The Cas/tau biosensor cell lines disclosed herein can be used in methods of dropout screening to reveal genetic vulnerabilities associated with tau aggregation. Such methods can comprise providing aggregation-positive and aggregation-negative populations of Cas/tau biosensor cells as disclosed elsewhere herein, introducing a library comprising a plurality of unique guide RNAs into each population, and determining abundance (e.g., read counts) of each of the plurality of unique guide RNAs at a plurality of time points over a time course in each population of cells.

As one example, a method can comprise providing an aggregation-positive population of cells and an aggregation-negative population of cells, wherein each population of cells comprises a Cas protein, a first tau repeat domain linked to a first reporter, and a second tau repeat domain linked to a second reporter as disclosed elsewhere herein. In the aggregation-positive population of cells the first tau repeat domain linked to the first reporter and the second tau repeat domain linked to the second reporter stably present in an aggregated state, whereas in the aggregation-negative population of cells the first tau repeat domain linked to the first reporter and the second tau repeat domain linked to the second reporter do not stably present in an aggregated state. The method can then comprise introducing into each population of cells a library comprising a plurality of unique guide RNAs that target a plurality of genes. The plurality of unique guide RNAs form complexes with the Cas protein, and the Cas protein cleaves the plurality of genes resulting in knockout of gene function. Finally, abundance of each of the plurality of unique guide RNAs can be determined at a plurality of time points over a time course in each population of cells. Depletion of a guide RNA in the aggregation-positive population of cells but not in the aggregation-negative population of cells can indicate that the gene targeted by the guide RNA exhibits synthetic lethality with tau protein aggregates and is a genetic vulnerability associated with tau aggregation or is a candidate genetic vulnerability associated tau aggregation (e.g., for further testing via secondary screens), wherein disruption of the gene targeted by the guide RNA is expected to exhibit synthetic lethality with tau protein aggregates. Alternatively, a more dramatic depletion pattern of a guide RNA over the time course in the aggregation-positive population of cells relative to the aggregation-negative population of cells can indicate that the gene targeted by the guide RNA exhibits synthetic lethality with tau protein aggregates and is a genetic vulnerability associated with tau aggregation or is a candidate genetic vulnerability associated tau aggregation (e.g., for further testing via secondary screens), wherein disruption of the gene targeted by the guide RNA is expected to exhibit synthetic lethality with tau protein aggregates. A more dramatic depletion pattern means that the guide RNA is depleted at a faster rate over the time course (e.g., a distinguishable depletion pattern using a differential test on fitted exponential decay rates).

Similarly, the SAM/tau biosensor cell lines disclosed herein can be used in methods of dropout screening to reveal genetic vulnerabilities associated with tau aggregation. Such methods can comprise providing aggregation-positive and aggregation-negative populations of SAM/tau biosensor cells as disclosed elsewhere herein, introducing a library comprising a plurality of unique guide RNAs into each population, and determining abundance (e.g., read counts) of each of the plurality of unique guide RNAs at a plurality of time points over a time course in each population of cells.

As one example, a method can comprise providing an aggregation-positive population of cells and an aggregation-negative population of cells, wherein each population of cells comprises a chimeric Cas protein comprising a nuclease-inactive Cas protein fused to one or more transcriptional activation domains, a chimeric adaptor protein comprising an adaptor protein fused to one or more transcriptional activation domains, a first tau repeat domain linked to a first reporter, and a second tau repeat domain linked to a second reporter as disclosed elsewhere herein. In the aggregation-positive population of cells the first tau repeat domain linked to the first reporter and the second tau repeat domain linked to the second reporter stably present in an aggregated state, whereas in the aggregation-negative population of cells the first tau repeat domain linked to the first reporter and the second tau repeat domain linked to the second reporter do not stably present in an aggregated state. The method can then comprise introducing into each population of cells a library comprising a plurality of unique guide RNAs that target a plurality of genes. The plurality of unique guide RNAs form complexes with the chimeric Cas protein and the chimeric adaptor protein, and the complexes activate transcription of the plurality of genes resulting in increased gene expression. Finally, abundance of each of the plurality of unique guide RNAs can be determined at a plurality of time points over a time course in each population of cells. Depletion of a guide RNA in the aggregation-positive population of cells but not in the aggregation-negative population of cells can indicate that the gene targeted by the guide RNA, when transcriptionally activated, exhibits synthetic lethality with tau protein aggregates and is a genetic vulnerability associated with tau aggregation or is a candidate genetic vulnerability associated tau aggregation (e.g., for further testing via secondary screens), wherein transcriptional activation of the gene targeted by the guide RNA is expected to exhibit synthetic lethality with tau protein aggregates. Alternatively, a more dramatic depletion pattern of a guide RNA over the time course in the aggregation-positive population of cells relative to the aggregation-negative population of cells can indicate that the gene targeted by the guide RNA, when transcriptionally activated, exhibits synthetic lethality with tau protein aggregates and is a genetic vulnerability associated with tau aggregation or is a candidate genetic vulnerability associated tau aggregation (e.g., for further testing via secondary screens), wherein transcriptional activation of the gene targeted by the guide RNA is expected to exhibit synthetic lethality with tau protein aggregates. A more dramatic depletion pattern means that the guide RNA is depleted at a faster rate over the time course (e.g., a distinguishable depletion pattern using a differential test on fitted exponential decay rates).

The Cas/tau biosensor cells used in the method can be any of the Cas/tau biosensor cells disclosed elsewhere herein. Likewise, the SAM/tau biosensor cells used in the method can be any of the SAM/tau biosensor cells disclosed elsewhere herein. The first tau repeat domain and the second tau repeat domain can be different or can be similar or the same. The tau repeat domain can be any of the tau repeat domains disclosed elsewhere herein. For example, the first tau repeat domain and/or the second tau repeat domain can be a wild type tau repeat domain or can comprise a pro-aggregation mutation, such as a tau P301S mutation. The first tau repeat domain and/or the second tau repeat domain can comprise a tau four-repeat domain. As one specific example, the first tau repeat domain and/or the second tau repeat domain can comprise, consist essentially of, or consist of SEQ ID NO: 11 or a sequence at least about 90%, 91%, 92%, 93%, 94%, 95%, 96%, 97%, 98%, or 99% identical to SEQ ID NO: 11. In one specific example, the nucleic acid encoding the tau repeat domain can comprise, consist essentially of, or consist of SEQ ID NO: 12 or a sequence at least about 90%, 91%, 92%, 93%, 94%, 95%, 96%, 97%, 98%, or 99% identical to SEQ ID NO: 12, optionally wherein the nucleic acid encodes a protein comprising, consisting essentially of, or consisting of SEQ ID NO: 11.

The first tau repeat domain can be linked to the first reporter and the second tau repeat domain can be linked to the second reporter by any means. For example, the reporter can be fused to the tau repeat domain (e.g., as part of a fusion protein). The reporter proteins can be any pair of reporter proteins that produce a detectable signal when the first tau repeat domain linked to the first reporter is aggregated with the second tau repeat domain linked to the second reporter. As one example, the first and second reporters can be a split luciferase protein. As another example, the first and second reporter proteins can be a fluorescence resonance energy transfer (FRET) pair. FRET is a physical phenomenon in which a donor fluorophore in its excited state non-radiatively transfers its excitation energy to a neighboring acceptor fluorophore, thereby causing the acceptor to emit its characteristic fluorescence. Examples of FRET pairs (donor and acceptor fluorophores) are well known. See, e.g., Bajar et al. (2016) *Sensors* (*Basel*) 16(9):1488, herein incorporated by reference in its entirety for all purposes. As one specific example of a FRET pair, the first reporter can be cyan fluorescent protein (CFP) and the second reporter can be yellow fluorescent protein (YFP). As a specific example, the CFP can comprise, consist essentially of, or consist of SEQ ID NO: 13 or a sequence at least about 90%, 91%, 92%, 93%, 94%, 95%, 96%, 97%, 98%, or 99% identical to SEQ ID NO: 13. As another specific example, the YFP can comprise, consist essentially of, or consist of SEQ ID NO: 15 or a sequence at least about 90%, 91%, 92%, 93%, 94%, 95%, 96%, 97%, 98%, or 99% identical to SEQ ID NO: 15.

For the Cas/tau biosensor cells, the Cas protein can be any Cas protein disclosed elsewhere herein. As one example, the Cas protein can be a Cas9 protein. For example, the Cas9 protein can be a *Streptococcus pyogenes* Cas9 protein. As one specific example, the Cas protein can comprise, consist essentially of, or consist of SEQ ID NO: 21 or a sequence at least about 90%, 91%, 92%, 93%, 94%, 95%, 96%, 97%, 98%, or 99% identical to SEQ ID NO: 21.

One or more or all of the Cas protein, the first tau repeat domain linked to the first reporter, and the second tau repeat domain linked to the second reporter can be stably expressed in the population of cells. For example, nucleic acids encoding one or more or all of the Cas protein, the first tau repeat domain linked to the first reporter, and the second tau repeat domain linked to the second reporter can be genomically integrated in the population of cells. In one specific example, the nucleic acid encoding the Cas protein can comprise, consist essentially of, or consist of SEQ ID NO: 22 or a sequence at least about 90%, 91%, 92%, 93%, 94%, 95%, 96%, 97%, 98%, or 99% identical to SEQ ID NO: 22, optionally wherein the nucleic acid encodes a protein comprising, consisting essentially of, or consisting of SEQ ID NO: 21.

For the SAM/tau biosensor cells, the Cas protein can be any Cas protein disclosed elsewhere herein. As one example, the Cas protein can be a Cas9 protein. For example, the Cas9 protein can be a *Streptococcus pyogenes* Cas9 protein. As one specific example, the chimeric Cas protein can comprise the nuclease-inactive Cas protein fused to a VP64 transcriptional activation domain. For example, the chimeric Cas protein can comprise from N-terminus to C-terminus: the nuclease-inactive Cas protein; a nuclear localization signal; and the VP64 transcriptional activator domain. As one specific example, the adaptor protein can be an MS2 coat protein, and the one or more transcriptional activation domains in the chimeric adaptor protein can comprise a p65 transcriptional activation domain and an HSF1 transcriptional activation domain. For example, the chimeric adaptor protein can comprise from N-terminus to C-terminus: the MS2 coat protein; a nuclear localization signal; the p65 transcriptional activation domain; and the HSF1 transcriptional activation domain. In one specific example, the nucleic acid encoding the chimeric Cas protein can comprise, consist essentially of, or consist of SEQ ID NO: 38 or a sequence at least about 90%, 91%, 92%, 93%, 94%, 95%, 96%, 97%, 98%, or 99% identical to SEQ ID NO: 38, optionally wherein the nucleic acid encodes a protein comprising, consisting essentially of, or consisting of SEQ ID NO: 36. In one specific example, the nucleic acid encoding the chimeric adaptor protein can comprise, consist essentially of, or consist of SEQ ID NO: 39 or a sequence at least about 90%, 91%, 92%, 93%, 94%, 95%, 96%, 97%, 98%, or 99% identical to SEQ ID NO: 39, optionally wherein the nucleic acid encodes a protein comprising, consisting essentially of, or consisting of SEQ ID NO: 37.

One or more or all of the chimeric Cas protein, the chimeric adaptor protein, the first tau repeat domain linked to the first reporter, and the second tau repeat domain linked to the second reporter can be stably expressed in the population of cells. For example, nucleic acids encoding one or more or all of the chimeric Cas protein, the chimeric adaptor protein, the first tau repeat domain linked to the first reporter, and the second tau repeat domain linked to the second reporter can be genomically integrated in the population of cells.

As disclosed elsewhere herein, the cells can be any type of cells. For example, the cells can be eukaryotic cells, mammalian cells, or human cells (e.g., HEK293T cells or neuronal cells).

The plurality of unique guide RNAs can be introduced into the populations of cells by any known means. In some methods, the guide RNAs are introduced into the populations of cells by viral transduction, such as retroviral, adenoviral, or lentiviral transduction. In a specific example, the guide RNAs can be introduced by lentiviral transduction. Each of the plurality of unique guide RNAs can be in a separate viral vector. The populations of cells can be infected at any multiplicity of infection. For example, the multiplicity of infection can be between about 0.1 and about 1.0, between about 0.1 and about 0.9, between about 0.1 and about 0.8, between about 0.1 and about 0.7, between about 0.1 and about 0.6, between about 0.1 and about 0.5, between about 0.1 and about 0.4, or between about 0.1 and about 0.3. Alternatively, the multiplicity of infection can be less than about 1.0, less than about 0.9, less than about 0.8, less than about 0.7, less than about 0.6, less than about 0.5, less than about 0.4, less than about 0.3, or less than about 0.2. In a specific example, the multiplicity of infection can be less than about 0.3.

The guide RNAs can be introduced into the populations of cells together with a selection marker or reporter gene to select for cells that have the guide RNAs, and the method can further comprise selecting cells that comprise the selection marker or reporter gene. Examples of selection markers and reporter genes are provided elsewhere herein. As one example, the selection marker can be one that imparts resistance to a drug, such as neomycin phosphotransferase, hygromycin B phosphotransferase, puromycin-N-acetyl-transferase, and blasticidin S deaminase. Another exemplary selection marker is bleomycin resistance protein, encoded by the Sh ble gene (*Streptoalloteichus hindustanus* bleomycin gene), which confers zeocin (phleomycin D1) resistance. For example, cells can be selected with a drug (e.g., puromycin) so that only cells transduced with a guide RNA construct are preserved for being used to carry out screening. For example, the drug can be puromycin or zeocin (phleomycin D1).

In some methods, the plurality of unique guide RNAs are introduced at a concentration selected such that a majority of the cells receive only one of the unique guide RNAs. For example, if the guide RNAs are being introduced by viral transduction, the cells can be infected at a low multiplicity of infection to ensure that most cells receive only one viral construct with high probability. As one specific example, the multiplicity of infection can be less than about 0.3.

The populations of cells into which the plurality of unique guide RNAs is introduced can be any suitable number of cells. For example, the populations of cells can comprise greater than about 50, greater than about 100, greater than about 200, greater than about 300, greater than about 400, greater than about 500, greater than about 600, greater than about 700, greater than about 800, greater than about 900, or greater than about 1000 cells per unique guide RNA. In a specific example, the populations of cells comprise greater than about 300 cells or greater than about 500 cells per unique guide RNA.

The plurality of unique guide RNAs can target any number of genes. For example, the plurality of unique guide RNAs can target about 50 or more genes, about 100 or more genes, about 200 or more genes, about 300 or more genes, about 400 or more genes, about 500 or more genes, about 1000 or more genes, about 2000 or more genes, about 3000 or more genes, about 4000 or more genes, about 5000 or more genes, about 10000 or more genes, or about 20000 or more genes. In some methods, the guide RNAs can be selected to target genes in a particular signaling pathway. In some methods, the library of unique guide RNAs is a genome-wide library.

The plurality of unique guide RNAs can target any number of sequences within each individual targeted gene. In some methods, a plurality of target sequences are targeted on average in each of the targeted plurality of genes. For example, about 2 to about 10, about 2 to about 9, about 2 to about 8, about 2 to about 7, about 2 to about 6, about 2 to about 5, about 2 to about 4, or about 2 to about 3 unique target sequences can be targeted on average in each of the targeted plurality of genes. For example, at least about 2, at least about 3, at least about 4, at least about 5, or at least about 6 unique target sequences can be targeted on average in each of the targeted plurality of genes. As a specific example, about 6 target sequences can be targeted on average in each of the targeted plurality of genes. As another specific example, about 3 to about 6 or about 4 to about 6 target sequences are targeted on average in each of the targeted plurality of genes.

The guide RNAs can target any desired location in the target genes. In some CRISPRn methods using the Cas/tau biosensor cells, each guide RNA targets a constitutive exon if possible. In some methods, each guide RNA targets a 5' constitutive exon if possible. In some methods, each guide RNA targets a first exon, a second exon, or a third exon (from the 5' end of the gene) if possible. In some CRISPRa methods using the SAM/tau biosensor cells, each guide RNA can target a guide RNA target sequence within 200 bp upstream of a transcription start site, if possible. In some CRISPRa methods using the SAM/tau biosensor cells, wherein each guide RNA can comprise one or more adaptor-binding elements to which the chimeric adaptor protein can specifically bind. In one example, each guide RNA comprises two adaptor-binding elements to which the chimeric adaptor protein can specifically bind, optionally wherein a first adaptor-binding element is within a first loop of each of the one or more guide RNAs, and a second adaptor-binding element is within a second loop of each of the one or more guide RNAs. For example, the adaptor-binding element can comprise the sequence set forth in SEQ ID NO: 33. In a specific example, each of one or more guide RNAs is a single guide RNA comprising a CRISPR RNA (crRNA) portion fused to a transactivating CRISPR RNA (tracrRNA) portion, and the first loop is the tetraloop corresponding to residues 13-16 of SEQ ID NO: 17, 19, 30, or 31, and the second loop is the stem loop 2 corresponding to residues 53-56 of SEQ ID NO: 17, 19, 30, or 31.

Abundance of guide RNAs can be determined by any suitable means. In a specific example, abundance is determined by next-generation sequencing. Next-generation sequencing refers to non-Sanger-based high-throughput DNA sequencing technologies. For example, determining abundance of a guide RNA can comprise measuring read counts of the guide RNA.

The time course in step (c) can be any suitable length of time. For example, the time course can be at least about 1 week, at least about 2 weeks, more than about 1 week, or more than about 2 weeks. For example, the time course can be between about 6 days and about 28 days, between about 9 days and about 25 days, between about 12 days and about 22 days, between about 15 days and about 19 days, or about 17 days. Similarly, the time course in step (c) can comprise any suitable number of cell passages or cell doublings. The time course can comprise about 5 to about 20, about 6 to about 19, about 7 to about 18, about 8 to about 17, about 9 to about 16, about 10 to about 15, about 11 to about 14, about 12 to about 13, or about 12 cell doublings. Alternatively, the time course can comprise about 2 to about 8, about 2 to about 7, about 2 to about 6, about 3 to about 5, about 3 to about 6, about 3 to about 7, about 3 to about 8, or about 4 cell passages. For example, there can be about 10 to about 15 cell doublings. In a specific example, there can be about 12 cell doublings between the first collection at day 3 and day 17 (i.e., about 4 cell passages). In some methods, to maintain a good representation of the genome wide gRNA library, the cells are not diluted too much at each passage. For example, the cells can be passaged about ¹⁄₁₀, about ⅑, about ⅛, about ⅐, about ⅙, about ⅕, about ¼, about ⅓, or about ½. In a specific example, the cells are passaged at about ⅕ (e.g., so that ≥2 cell doublings).

The tau biosensor cells described herein are primed for aggregation. That is, they are at a tipping point of aggregation. We have found that tau aggregates cause a strong and consistent change in the transcriptional profile of tau biosensor cells. We hypothesized that these aggregation-positive cells may be selectively vulnerable to certain genetic insults in a way that aggregation-negative cells are not. We also hypothesized that any "mutation" in the CRISPRn screening that would trigger "specific" cell death in aggregate-containing cells may also have a lesser deleterious effect on non-aggregate-containing cells. Likewise, any gene activation in the CRISPRa screening that would trigger "specific" cell death in aggregate-containing cells may also have a lesser deleterious effect on non-aggregate-containing cells. Assessment at a plurality of time points allows us to identify this type of target by identifying RNA depletion profiles (depletion rate or steepness of gRNA depletion) over time rather than only at the last passage as compared to the first passage, in which case this type of target would be missed. For example, this type of depletion profile was observed with Target Gene 1. We identified this type of depletion profiles for our lead target, Target Gene 1.

The plurality of time points in step (c) can be any suitable number of time points. For example, the plurality of time points in step (c) can be at least about 2 time points, at least about 3 time points, at least about 4 time points, at least about 5 time points at least about 6 time points, more than about 2 time points, more than about 3 time points, more than about 4 time points, more than about 5 time points, or more than about 6 time points. For example, there can be between about 3 and about 9 time points, between about 4 and about 8 time points, between about 5 and about 7 time points, or about 6 time points. As another example, there can be between about 2 and about 6 time points, between about 3 and about 5 time points, or about 4 time points.

Each time point can correspond to passaging the cells. The period of time between each successive time point can be any suitable time period. For example, there can be at least about 12 hours, at least about 1 day, at least about 2 days, at least about 3 days, more than about 12 hours, more than about 1 day, more than about 2 days, or more than about 3 days between each time point. For example, there can be about 1 day and about 6 days, about 2 days to about 5 days, or about 3 days to about 4 days between each successive time point. As a specific example, there can be at least about 2 days or about 3 days to about 4 days between each successive time point (i.e., between successive passages of the cells).

The first time point can be at any suitable time point after the guide RNAs are introduced into the populations of cells. For example, with CRISPRn screening methods using the Cas/tau biosensor cells, the first time point can be after a sufficient amount of time for the guide RNAs to form complexes with the Cas protein, and for the Cas protein to cleave the plurality of genes resulting in knockout of gene function. Likewise, with CRISPRa screening methods using the SAM/tau biosensor cells, the first time point can be after a sufficient amount of time for the guide RNAs to form complexes with the chimeric Cas protein and the chimeric adaptor protein, and for the complexes to activate transcription of the plurality of genes resulting in increased gene expression. For example, the first time point can be at least about 1 day, at least about 2 days, at least about 3 days, more than about 1 day, more than about 2 days, or more than about 3 days after introduction of the guide RNAs into the cells. Alternatively, the first time point can be between about 0 days and about 6 days, between about 1 day and about 5 days, between about 2 days and about 4 days, or about 3 days after introduction of the guide RNAs into the cells.

In one specific example, abundance of guide RNAs is assessed at days 3, 6 or 7, 10 or 11, 13 or 14, and 17 following introduction of the guide RNAs on day 0. For example, abundance of guide RNAs can be assessed at days 3, 7, 10, 14, and 17 following introduction of the guide RNAs on day 0.

Whether a guide RNA is considered depleted over the time course can involve different assessments. As one example, a guide RNA can be considered depleted if the abundance of the guide RNA at each time point is less than or equal to the abundance of the guide RNA at the preceding time point. As another example, a guide RNA can be considered depleted in step (c) if the abundance of the guide RNA at each time point after the second time point is less than or equal to the abundance of the time point two time points prior (i.e., the time point before the preceding time point, such as time point 3 compared to time point 1, time point 4 compared to time point 2, time point 5 compared to time point 3, and so on). In one specific example, abundance of guide RNAs is assessed at days 3, 6 or 7, 10 or 11, 13 or 14, and 17 following introduction of the guide RNAs on day 0, and a guide RNA is considered depleted if its abundance at day 10 or 11 is less than at day 3, its abundance at day 13 or 14 is less than at day 6 or 7, and its abundance at day 17 is less than at day 10 or 11.

The assessment in the methods disclosed herein can also consider the trend among all guide RNAs in the library that target a particular gene. For example, a gene can be considered to exhibit synthetic lethality with tau protein aggregates if at least about 30%, at least about 33%, at least about 35%, at least about 40%, at least about 45%, at least about 50%, at least about 60%, at least about 65%, at least about 70%, at least about 75%, more than about 30%, more than about 33%, more than about 35%, more than about 40%, more than about 45%, more than about 50%, more than about 60%, more than about 65%, more than about 70%, or more than about 75% (e.g., at least about 30% or more than about 30%) of the guide RNAs in the library that target the gene are depleted in the aggregation-positive population of cells but not in the aggregation-negative population of cells. As some specific non-limiting examples, a gene can be considered to exhibit synthetic lethality with tau protein aggregates (or is expected to exhibit synthetic lethality with tau protein aggregates) in the following situations: (1) if there is one guide RNA in the library that targets the gene, the one guide RNA is depleted in the aggregation-positive population of cells but not in the aggregation-negative population of cells; (2) if there are two guide RNAs in the library that target the gene, at least one of the two guide RNAs is depleted in the aggregation-positive population of cells but not in the aggregation-negative population of cells; (3) if there are three guide RNAs in the library that target the gene, at least one of the three guide RNAs is depleted in the aggregation-positive population of cells but not in the aggregation-negative population of cells; (4) if there are four guide RNAs in the library that target the gene, at least two of the four guide RNAs is depleted in the aggregation-positive population of cells but not in the aggregation-negative population of cells; (5) if there are five guide RNAs in the library that target the gene, at least two of the five guide RNAs is depleted in the aggregation-positive population of cells but not in the aggregation-negative population of cells; and (6) if there are six guide RNAs in the library that target the gene, at least three of the six guide RNAs is depleted in the aggregation-positive population of cells but not in the aggregation-negative population of cells.

The assessment in the methods disclosed herein can also consider the trend of guide RNAs in the library that target a particular gene over multiple experiments. For example, the method can be repeated at least about 2 times, at least about 3 times, at least about 4 times, at least about 5 times, at least about 6 times, more than about 1 time, more than about 2 times, more than about 3 times, more than about 4 times, more than about 5 times, or more than about 6 times. For example, a gene can be considered to exhibit synthetic lethality with tau protein aggregates if it is selected (i.e., if it is considered to exhibit synthetic lethality with tau protein aggregates) in at least about 30%, at least about 35%, at least about 40%, at least about 45%, at least about 50%, at least about 55%, at least about 60%, at least about 65%, at least about 70%, at least about 75%, more than about 30%, more than about 35%, more than about 40%, more than about 45%, more than about 50%, more than about 55%, more than about 60%, more than about 65%, more than about 70%, or more than about 75% of all experiments. For example, a gene can be considered to exhibit synthetic lethality with tau protein aggregates if it is selected (i.e., if it is considered to exhibit synthetic lethality with tau protein aggregates) in more than about 50% or more than about 60% of all experiments. As a specific example, the methods can be repeated in three experiments, and the gene can be considered to exhibit synthetic lethality with tau protein aggregates (or can be selected as a candidate for exhibiting synthetic lethality with tau protein aggregates (e.g., for further testing in secondary screens)) if it is selected (i.e., if it is considered to exhibit synthetic lethality with tau protein aggregates) in at least two out of the three experiments.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | Protein | Tau R1 Repeat Domain |
| 2 | Protein | Tau R2 Repeat Domain |
| 3 | Protein | Tau R3 Repeat Domain |
| 4 | Protein | Tau R4 Repeat Domain |
| 5 | DNA | Tau R1 Repeat Domain Coding Sequence |
| 6 | DNA | Tau R2 Repeat Domain Coding Sequence |
| 7 | DNA | Tau R3 Repeat Domain Coding Sequence |
| 8 | DNA | Tau R4 Repeat Domain Coding Sequence |
| 9 | Protein | Tau Four-Repeat Domain (R1-R4; amino acids 243-375 of full-length (P10636-8) Tau) |
| 10 | DNA | Coding Sequence for Tau Four-Repeat Domain (R1-R4; coding sequence for amino acids 243-375 of full-length (P10636-8) Tau) |
| 11 | Protein | Tau Four-Repeat Domain (R1-R4) with P301S Mutation |
| 12 | DNA | Coding Sequence for Tau Four-Repeat Domain (R1-R4) with P301S Mutation |
| 13 | Protein | eCFP |
| 14 | DNA | eCFP Coding Sequence |
| 15 | Protein | eYFP |
| 16 | DNA | eYFP Coding Sequence |
| 17 | RNA | Guide RNA Scaffold V1 |
| 18 | RNA | Guide RNA Scaffold V2 |
| 19 | RNA | Guide RNA Scaffold V3 |
| 20 | RNA | Guide RNA Scaffold V4 |
| 21 | Protein | Cas9 |
| 22 | DNA | Cas9 Coding Sequence |
| 23 | RNA | crRNA Tail |
| 24 | RNA | TracrRNA |
| 25 | DNA | Guide RNA Target Sequence Plus PAM V1 |
| 26 | DNA | Guide RNA Target Sequence Plus PAM V2 |
| 27 | DNA | Guide RNA Target Sequence Plus PAM V3 |
| 28 | RNA | TracrRNA v2 |
| 29 | RNA | TracrRNA v3 |
| 30 | RNA | Guide RNA Scaffold V5 |
| 31 | RNA | Guide RNA Scaffold V6 |
| 32 | RNA | Guide RNA Scaffold V7 |
| 33 | RNA | MS2-binding loop |
| 34 | RNA | Guide RNA Scaffold with MS2-Binding Loops |
| 35 | RNA | Generic sgRNA with MS2-Binding Loops |
| 36 | Protein | dCas9-VP64 chimeric Cas protein |
| 37 | Protein | MCP-p65-HSF1 chimeric adaptor protein |
| 38 | DNA | DNA Encoding dCas9-VP64 chimeric Cas protein |
| 39 | DNA | DNA Encoding MCP-p65-HSF1 chimeric adaptor protein |
| 40 | Protein | MCP |
| 41 | DNA | DNA Encoding MCP |
| 42 | DNA | Lenti dCas9-VP64 |
| 43 | DNA | Lenti MCP-p65-HSF1_Hygro |

EXAMPLES

Example 1. Development of Genome-Wide CRISPR/Cas9 Screening Platform to Identify Genetic Vulnerabilities Associated with Tau Aggregation Abnormal aggregation or fibrillization of proteins is a defining feature of many diseases, notably including a number of neurodegenerative diseases such as Alzheimer's disease (AD), Parkinson's disease (PD), frontotemporal dementia (FTD), amyotrophic lateral sclerosis (ALS), chronic traumatic encephalopathy (CTE), Creutzfeldt-Jakob disease (CJD), and others. In many of these diseases, the fibrillization of certain proteins into insoluble aggregates is not only a hallmark of disease, but has also been implicated as a causative factor of neurotoxicity. Furthermore, these diseases are characterized by propagation of aggregate pathology through the central nervous system following stereotypical patterns, a process which correlates with disease progression. The identification of genes and genetic pathways that modify the processes of abnormal protein aggregation, or cell-to-cell propagation of aggregates, are therefore of great value in better understanding neurodegenerative disease etiology as well as in devising strategies for therapeutic intervention.

To identify genes and pathways that exhibit synthetic lethality with disease-associated protein aggregates, a platform was developed for performing genome-wide screens with CRISPR nuclease (CRISPRn) sgRNA libraries. The platform identifies genes that, when disrupted, cause cell death specifically in the context of abnormal protein aggregation. The identification of such genes may elucidate the mechanisms of aggregate-associated neurotoxicity, and genetic pathways that promote death of neurons in the context of neurodegenerative disease.

The screen employed a Tau biosensor human cell line consisting of HEK293T cells stably expressing Tau four-repeat domain, Tau 4RD, comprising the Tau microtubule binding domain (MBD) with the P301S pathogenic mutation, fused to either CFP or YFP. That is, the HEK293T cell lines contain two transgenes stably expressing disease-associated protein variants fused to the fluorescent protein CFP or the fluorescent protein YFP: Tau$^{4RD}$-CFP/Tau$^{4RD}$-YFP (TCY), wherein the Tau repeat domain (4RD) comprises the P301S pathogenic mutation. See FIG. 1. In these biosensor lines, Tau-CFP/Tau-YFP protein aggregation produces a FRET signal, the result of a transfer of fluorescent energy from donor CFP to acceptor YFP. See FIG. 2. FRET-positive cells, which contain Tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal. Aggregate-containing cells can be isolated by FACS. Stably propagating aggregate-containing cell lines, Agg[+], can be isolated by clonal serial dilution of Agg[−] cell lines.

Figure 3B:
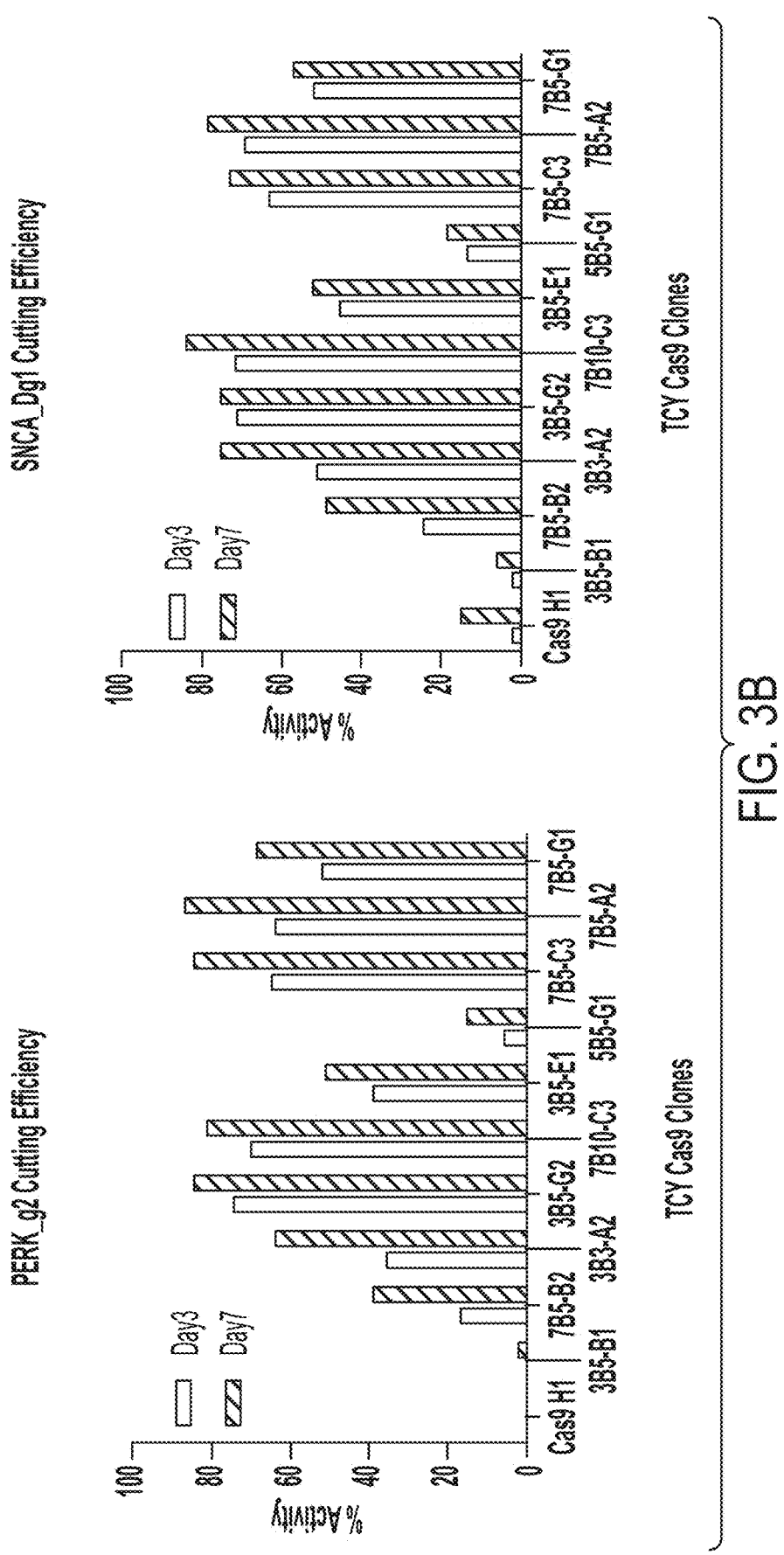
FIG. 3B shows cutting efficiency at the PERK locus and the SNCA locus in the Cas9 TCY clones three and seven days after transduction with sgRNAs targeting PERK and SNCA respectively.

Several modifications were made to this Tau biosensor cell line to make it useful for genetic screening. First, these Tau biosensor cells were modified by introducing a Cas9-expressing transgene via a lentiviral vector. Clonal transgenic cell lines expressing Cas9 were selected with blasticidin and isolated by clonal serial dilution to obtain single-cell-derived clones. Clones were evaluated for level of Cas9 expression by qRT-PCR (FIG. 3A) and for DNA cleavage activity by digital PCR (FIG. 3B). Relative Cas9 expression levels are also shown in Table 3.

TABLE 3

Relative Cas9 Expression Levels.

| Clone Name | Cas9D Ct rep1 | rep2 | rep3 | rep4 | Cas9D AVG Ct | B2m AVG Ct | Cas9D-B2m delta Ct |
|---|---|---|---|---|---|---|---|
| 3B5-B1 | 26.22 | 26.31 | 26.36 | 26.45 | 26.33 | 22.01 | 4.33 |
| 3B5-G2 | 23.68 | 23.85 | 24.39 | 23.61 | 23.88 | 21.51 | 2.38 |
| 7B5-B2 | 23.63 | 23.60 | 24.12 | 23.50 | 23.71 | 21.38 | 2.34 |
| 3B3-A2 | 24.05 | 23.95 | 24.02 | 24.47 | 24.12 | 21.94 | 2.19 |
| 7B10-C3 | 22.58 | 22.71 | 22.67 | 23.20 | 22.79 | 21.19 | 1.59 |
| 3B5-E1 | 24.12 | 24.32 | 24.75 | 24.05 | 24.31 | 22.81 | 1.50 |
| 3B5-G1 | 21.16 | 21.14 | 21.09 | 21.43 | 21.20 | 21.35 | −0.15 |
| 7B5-C3 | 19.98 | 19.99 | 19.86 | 19.97 | 19.95 | 21.24 | −1.29 |
| 7B5-A2 | 18.84 | 18.74 | 19.33 | 18.99 | 18.97 | 22.10 | −3.12 |
| 7B5-G1 | 19.01 | 18.88 | 19.61 | 19.18 | 19.17 | 22.33 | −3.16 |

Specifically, Cas9 mutation efficiency was assessed by digital PCR 3 and 7 days after transduction of lentiviruses encoding gRNAs against two selected target genes. Cutting efficiency was limited by Cas9 levels in lower-expressing clones. A clone with an adequate level of Cas9 expression was needed to achieve maximum activity. Several derived clones with lower Cas9 expression were not able to cut target sequences efficiently, whereas clones with higher expression (including those used for screening) were able to generate mutations at target sequences in the genes PERK and SNCA with approximately 80% efficiency after three days in culture. Efficient cutting was observed already at 3 days after gRNA transduction with only marginal improvement after 7 days. Clone 7B10-C3 was selected as a high-performing clone to use for subsequent library screens.

Figure 5:
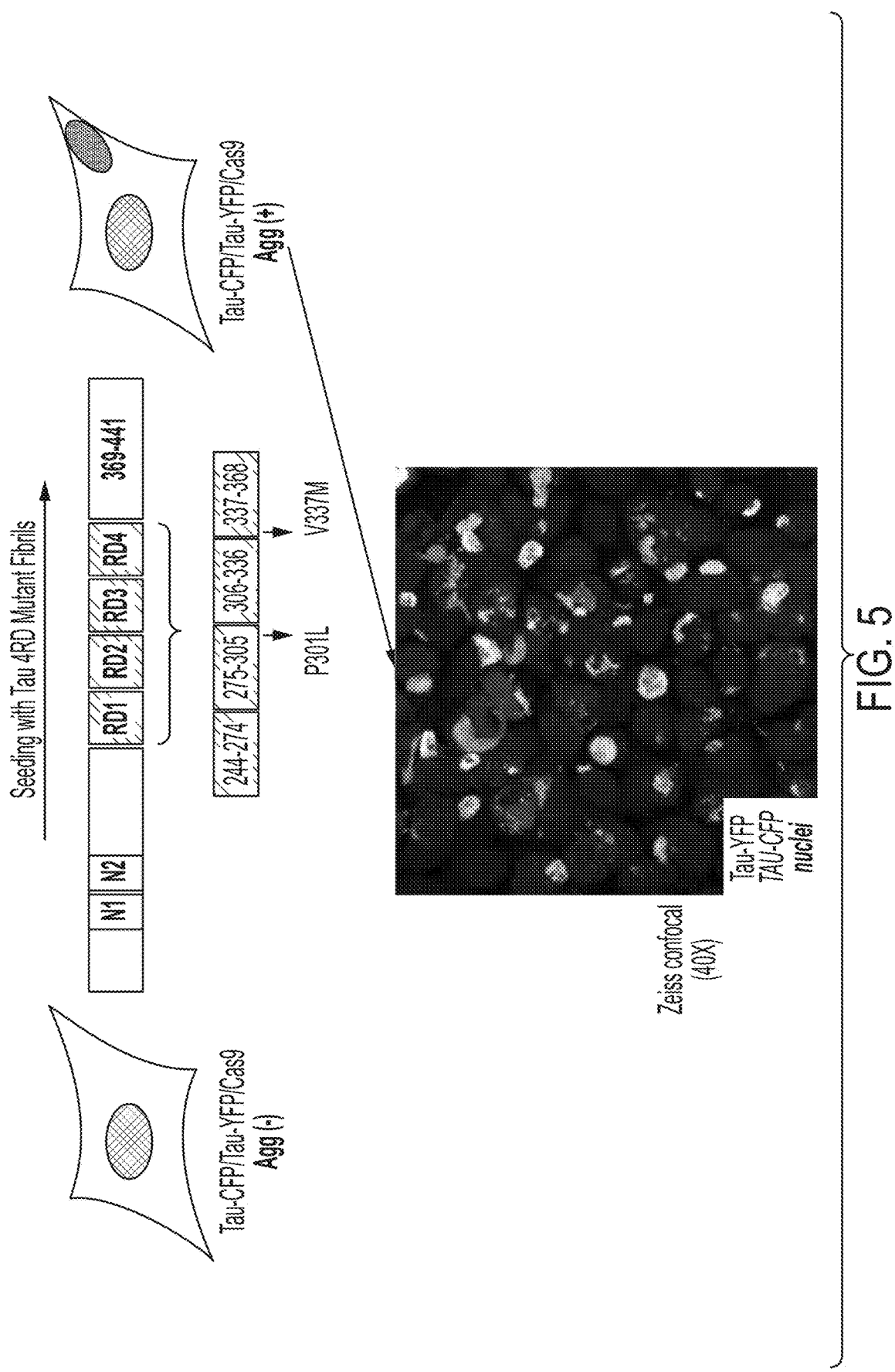
FIG. 5 is a schematic showing derivation of Tau$^{4RD}$-CFP/Tau$^{4RD}$-YFP/Cas9 Agg[+] subclones containing stably propagating Tau aggregates. A FRET microscopy image showing the subclone with Tau aggregates is also shown.

Second, sub-clones of these Cas9-expressing Tau-CFP/Tau-YFP (TCY) biosensor cell lines in which Tau protein is stably present in either a non-aggregated (the default state) (Agg[−]) or an aggregated state (Agg[+]) were obtained. To obtain cell lines in which Tau protein is stably and persistently present in an aggregated state, the Cas9-expressing cells were treated with recombinant fibrillized Tau mixed with lipofectamine reagent in order to "seed" the aggregation of the Tau protein transgenically expressed by these cells. See FIG. 5. The "seeded" cells were then serially diluted to obtain single cell-derived clones, and these clones were then expanded to identify those clonal cell lines in which Tau aggregates stably persist in all cells with growth and multiple passages over time.

Figure 7:
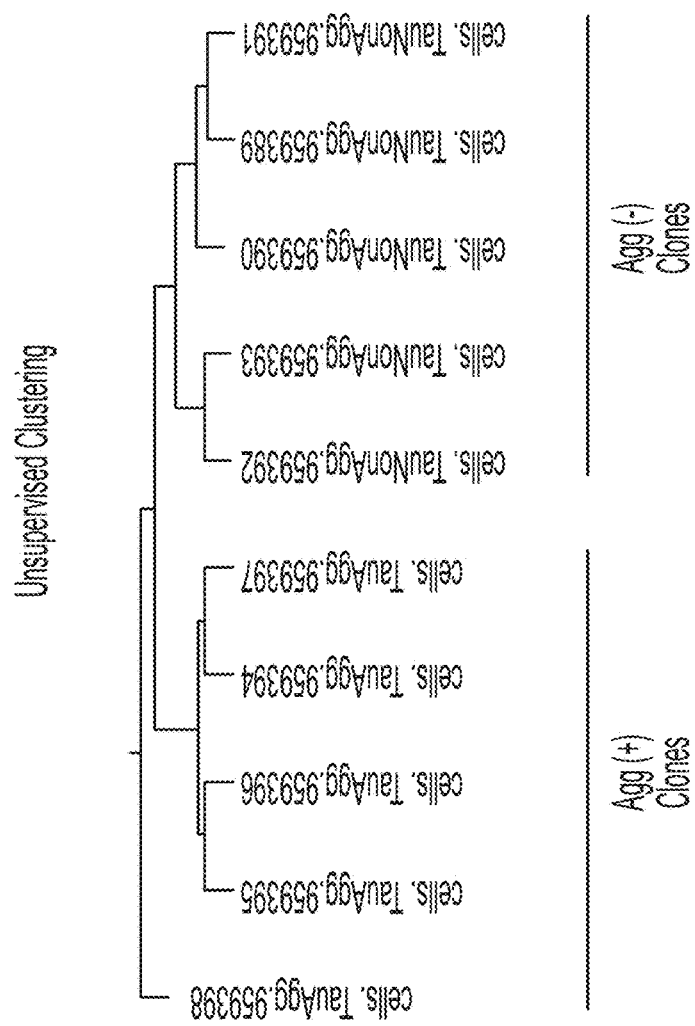
FIG. 7 shows results from unsupervised clustering that indicate that Agg[+] clone samples and Agg[−] clone samples are distinct by aggregation status (clustering procedure: log transformation of reads per kilobase million (RPKM); distance metric: 1−absolute value of Pearson correlation coefficient; hierarchical clustering).
Figure 6:
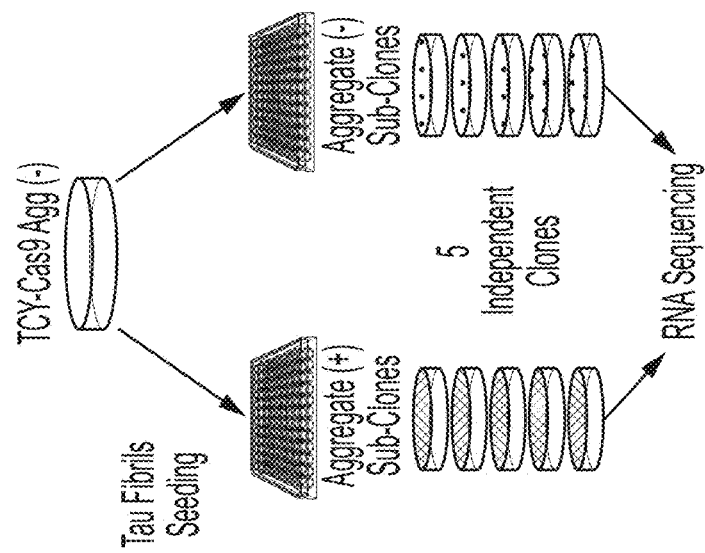
FIG. 6 is a schematic of an experiment to assess genes perturbed by Tau aggregation.

We then analyzed the Agg[+] and Agg[−] subclones to determine whether certain genes were perturbed by Tau aggregation. See FIG. 6. Unsupervised clustering indicated that the Agg[+] subclones and Agg[−] subclones were distinct by aggregation status (clustering procedure: log transformation of reads per kilobase million (RPKM); distance metric: 1−absolute value of Pearson correlation coefficient; hierarchical clustering). See FIG. 7. Unsupervised clustering refers to clustering samples without any prior knowledge about the samples (e.g., what cell line a sample is from (Agg[+] or Agg[−])) such that the cluster formation among samples is completely driven by the data itself. The procedure was as follows: (1) add 1 to the expression level of all genes (unit is RPKM) in each sample; (2) log 2 transform the RPKM+1 values; (3) calculate pair-wise Pearson correlation coefficient among all samples; (4) calculate similarity between ever pair of samples as 1-absolute value of the Pearson correlation coefficient; and (5) apply standard hierarchical clustering algorithm on values from (4). The data showed that samples from Agg[+] and Agg[−] cell lines form distinctly separated clusters solely based on their gene expression profiles, suggesting Agg[+] and Agg[−] cell lines are different at the gene expression level.

Figure 8:
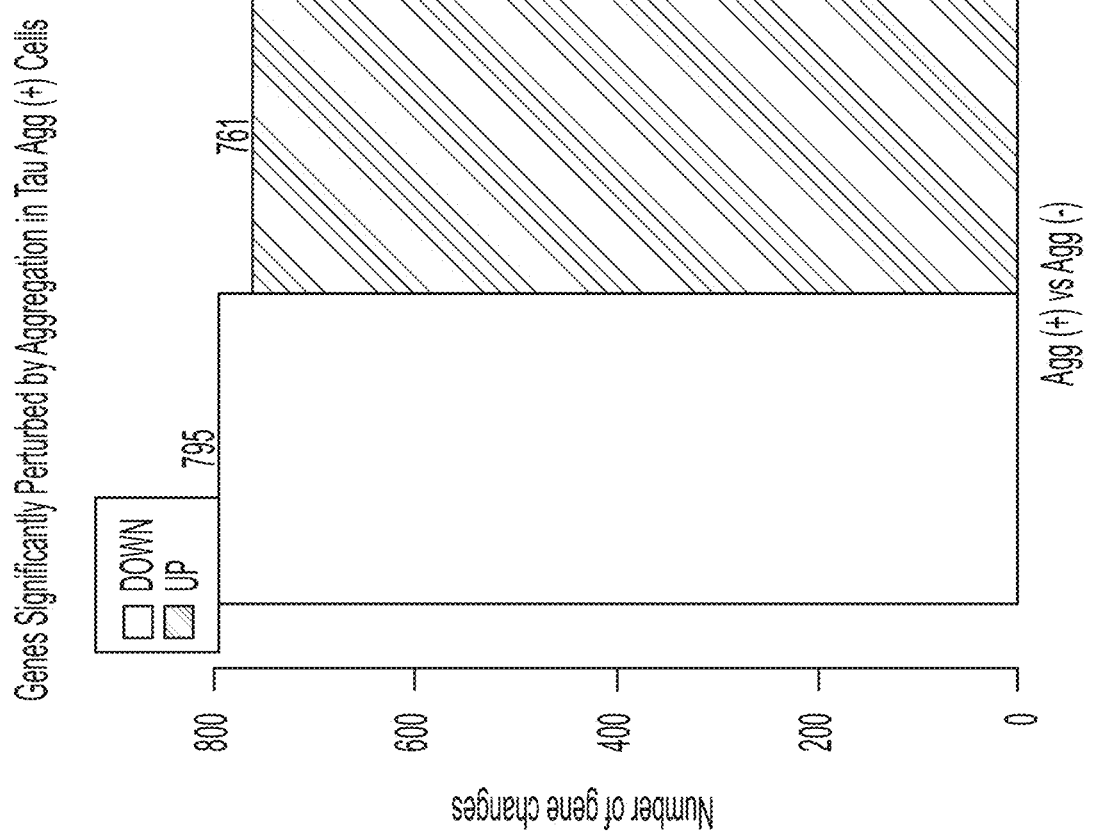
FIG. 8 shows genes significantly perturbed by aggregation in Tau Agg[+] cells (significantly perturbed genes defined as fold change ≥1.5 (either up or down) and p value ≤0.01.

RNA sequencing of Tau biosensor Agg[+] and Agg[−] subclones revealed that >1500 genes are perturbed by Tau aggregation. See FIG. 8. Significantly perturbed genes were defined as those having a fold change ≥1.5 in either direction and a p value ≤0.01. RNAseq of five Agg[+] sub-clones and five Agg[−] sub-clones demonstrated that the presence of Tau aggregates causes a strong and consistent change in the transcriptional profile of Agg[+] sub-clones as compared to Agg[−] sub-clones. Thus, Agg[+] sub-clones may be selectively vulnerable to certain genetic insults in a way that Agg[−] sub-clones are not. As explained in Example 2, we probed these vulnerabilities using CRISPR libraries to perform a dropout screen and identify sgRNAs that cause synthetic lethality when in combination with Tau aggregates.

Figure 4:
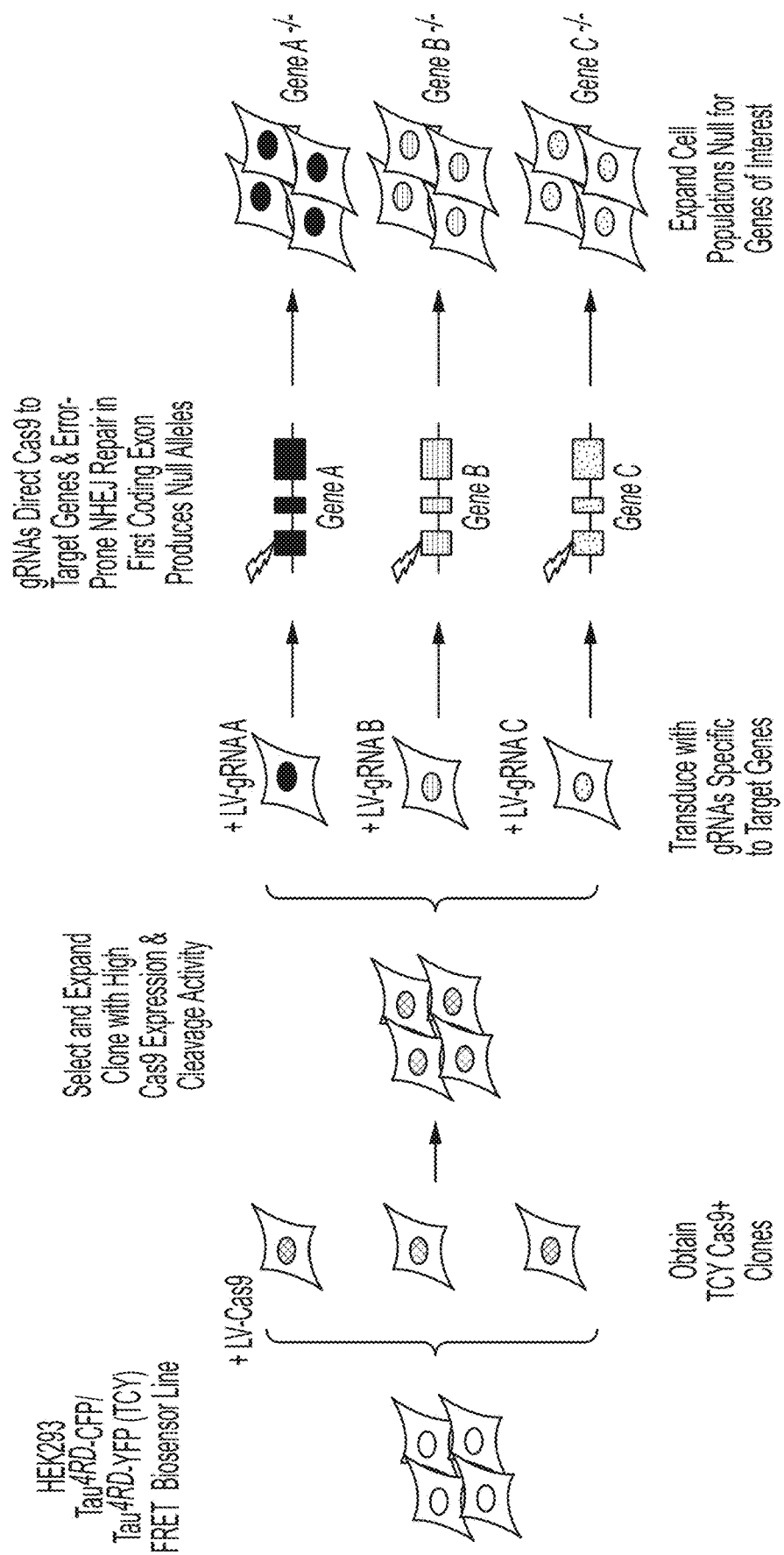
FIG. 4 shows a schematic of the strategy for disruption of target genes in Cas9 TCY biosensor cell using a genome-wide CRISPR/Cas9 sgRNA library.
Figure 9:
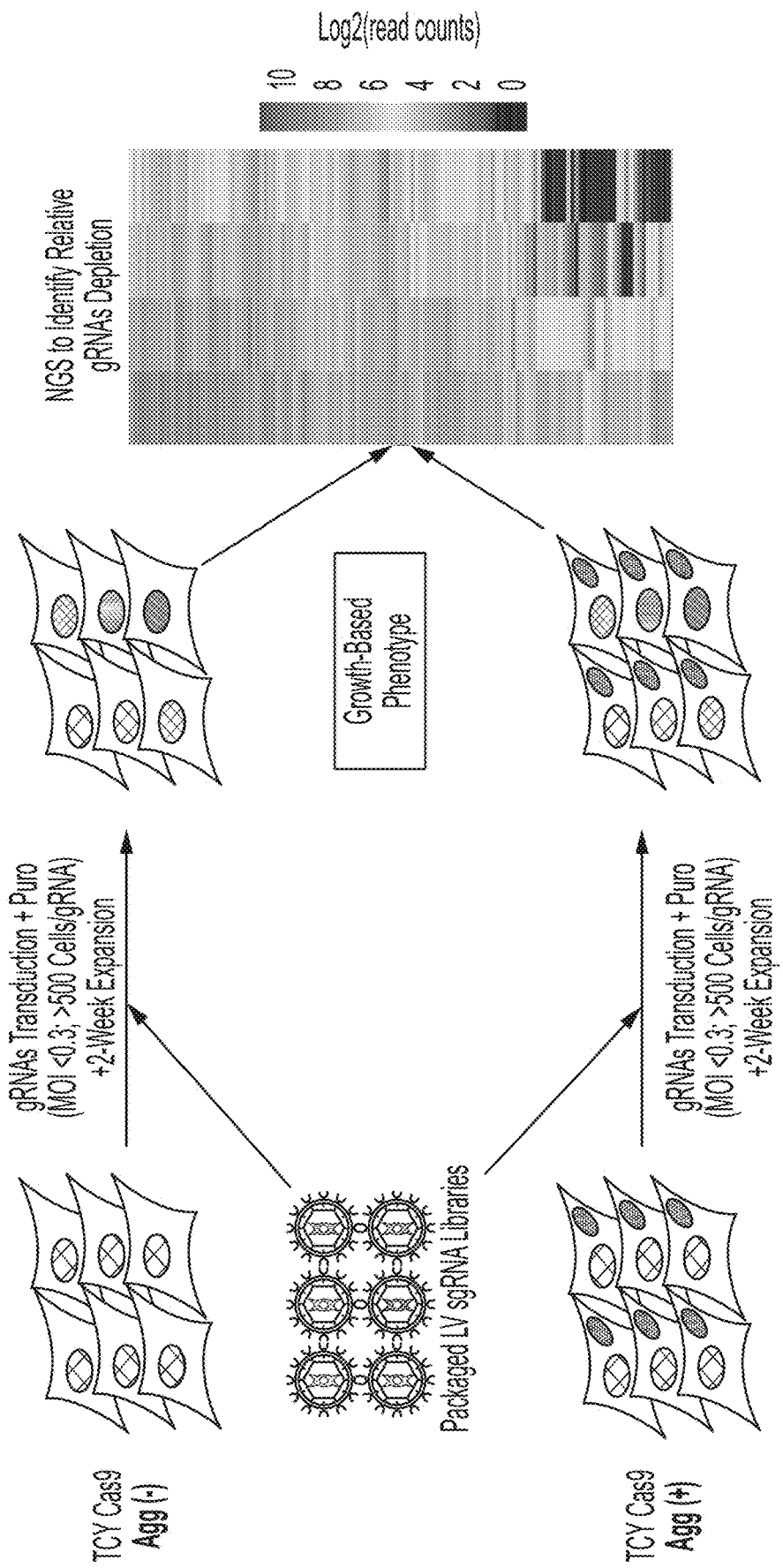
FIG. 9 shows a general schematic of the pooled genome-wide CRISPR nuclease (CRISPRn) screen to reveal genetic vulnerabilities associated with Tau aggregation.

Example 2. Genome-Wide CRISPR/Cas9 Screening to Identify Genetic Vulnerabilities Associated with Tau Aggregation To probe the vulnerabilities identified in Example 1, a pooled genome-wide CRISPR nuclease (CRISPRn) screen was performed to reveal genetic vulnerabilities associated with Tau aggregation. Specifically, the Cas9-expressing Tau-CFP/Tau-YFP biosensor cells, either with aggregates (Agg [+]) or without aggregates (Agg[−]), were transduced with two human genome-wide CRISPR sgRNA libraries using a lentiviral delivery approach to introduce knock-out mutations at each target gene at a representation of 500× cells per sgRNA. See FIGS. 4 and 9. The CRISPR sgRNA libraries target 5' constitutive exons for functional knock-out with an average coverage of 3-4 sgRNAs per gene. The sgRNAs were designed to avoid off-target effects by avoiding sgRNAs with two or fewer mismatches to off-target genomic sequences. The libraries cover 19,050 human genes and 1864 miRNA with 1000 non-targeting control sgRNAs. The libraries were transduced at a multiplicity of infection (MOI)<0.3 at a coverage of >500 cells per sgRNA. Tau biosensor cells were grown under puromycin selection to select cells with integration and expression of a unique sgRNA per cell. Puromycin selection began 24 h after transduction at 1 μg/mL.

Figure 10A:
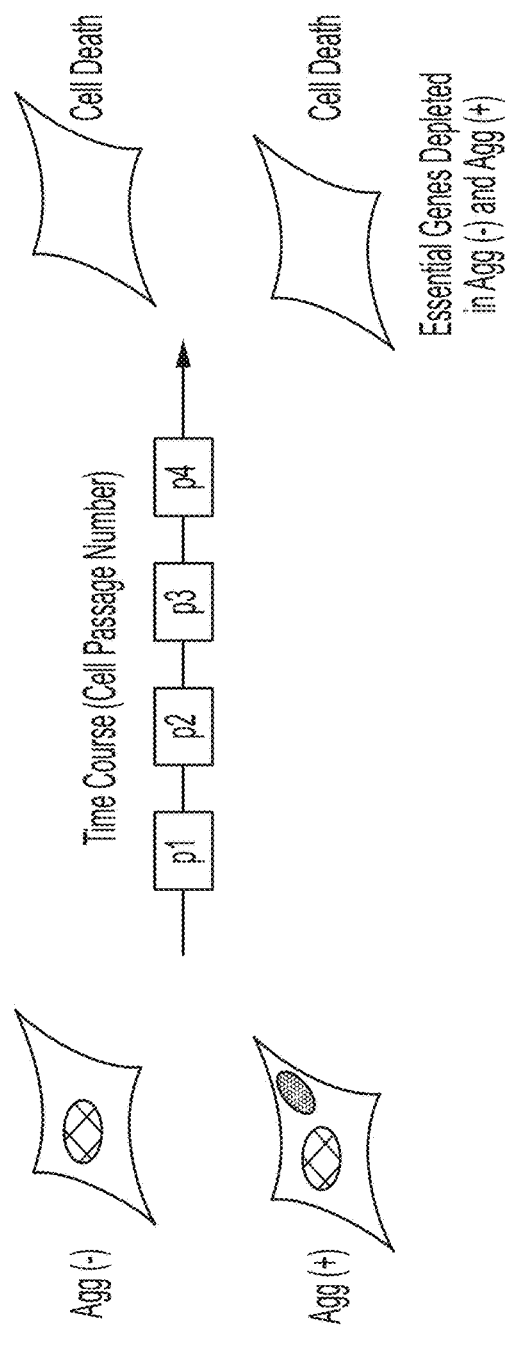
FIG. 10A shows a general schematic of the identification of essential genes (sgRNAs targeting those genes that are depleted in both Agg[+] and Agg[−]).
Figure 10B:
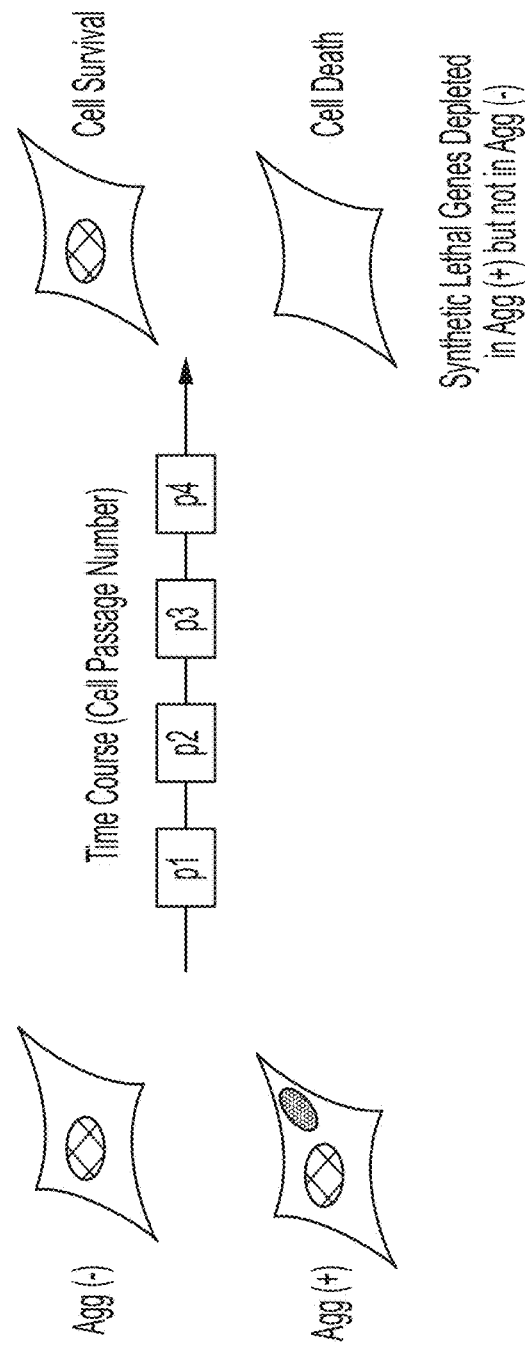
FIG. 10B shows a general schematic of the identification of synthetic lethal genes (sgRNAs targeting those genes that are depleted in Agg[+] but not in Agg[−]).
Figure 12:
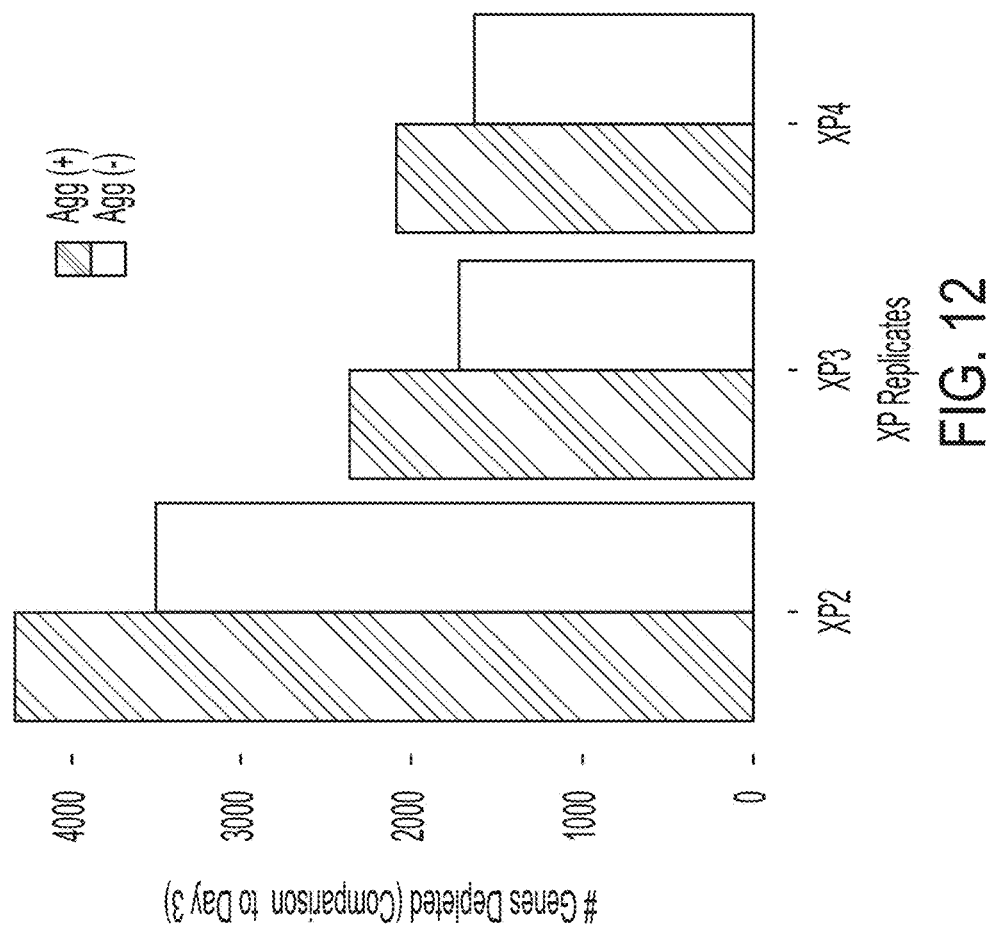
FIG. 12 shows the number of genes for which sgRNAs were depleted in Agg[+] and Agg[−] samples.

Samples of (Agg[+]) and (Agg[−]) cells were collected at five time points: Days 3, 6-7, 10-11, 13-14, and 17 post-transduction. DNA isolation and PCR amplification of the integrated sgRNA constructs allowed a characterization by next generation sequencing (NGS) of the sgRNA repertoire in each cell line at each time point. The screening consisted of 3 replicated experiments. Analysis of the NGS data enabled the identification of essential genes, consisting of those genes whose targeting sgRNAs become depleted over time in both the Agg[+] and Agg[−] cell lines. See FIG. 10A. More importantly, this screening method enabled the identification of synthetic lethal genes, consisting of genes whose targeting sgRNAs become depleted over time preferentially in the Agg[+] as compared to the Agg[−] cell lines. See FIG. 10B.

Figure 11:
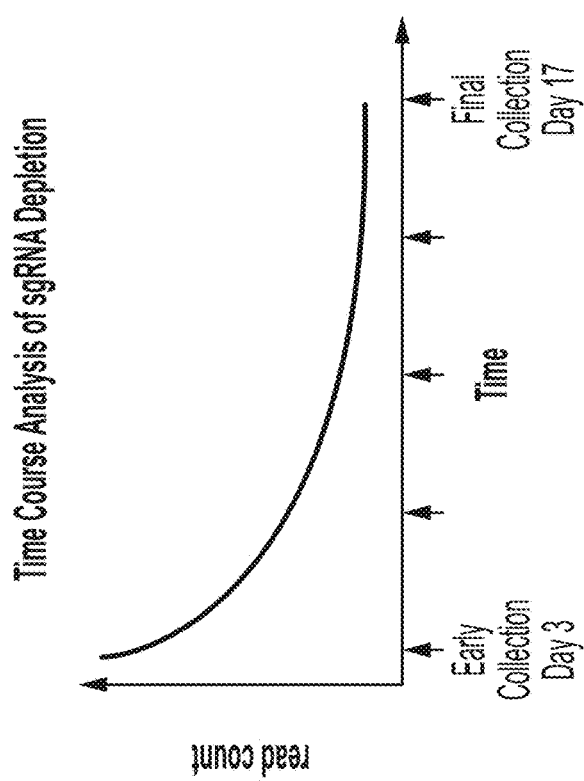
FIG. 11 shows a schematic of the full time course approach to identify genes for which there is a sgRNA depletion pattern over time.

Depletion profiles were assessed using a newly defined time course analysis in which sgRNAs with a consistent pattern of decreasing NGS reads from the earliest time point (Day 3) to the final time point (Day 17) were considered to be depleted. See FIG. 11 and Table 4.

TABLE 4

Time Course Strategy for CRISPRn Dropout Screen.

| Tau Biosensor Lines | LV Library | Samples Collected from 3 Replicate Experiments | | | | |
|---|---|---|---|---|---|---|
| | | Passage 1 | Passage 2 | Passage 3 | Passage 4 | Final Collection |
| Agg[−] | Library A Library B | Day 3 | Day 6-7 | Day 10-11 | Day 13-14 | Day 17 |
| Agg[+] | Library A Library B | Day 3 | Day 6-7 | Day 10-11 | Day 13-14 | Day 17 |

This is a novel analytical approach to evaluating sgRNA depletion, as compared to the more conventional approach of simply comparing the NGS reads of the endpoint cell collection to the first passage. In comparison, other published genome-wide CRISPRn screens for depletion have compared CRISPR scores as the ratio of read counts between final collection and early passage. In contrast, our approach was to examine the full time course to identify genes that exhibit a pattern of sgRNA depletion over time. Time course analysis identified more genes sgRNAs depleted in the Agg[+] subset than in the Agg[−] subset in all three repeat experiments.

The first analysis steps included quality control (non-targeted sgRNAs), normalization (by total reads per sample), and flagging "presence"/"absence" per sgRNA per sample with a detection cutoff of 30 reads. First, non-targeting sgRNAs were tested. It was confirmed that there was no strong or systematic perturbation or depletion of the 1000 non-targeting control sgRNAs. Second, experiments were done to show that the plasmid sgRNA library and the Day 3 samples were very similar with respect to read counts of the sgRNAs (no significant sgRNA depletion had occurred at Day 3). This was validation for using Day 3 as the reference point for the time course analysis.

Depleted genes were then identified via time course analysis. In each repeat, depleted sgRNAs with non-increasing temporal patterns (read count at Day 10≤at Day 3; read count at Day 14≤at Day 6; and read count Day 17≤at Day 10) relative to Day 3 were selected. sgRNAs already depleted at Day3 (i.e., below the detection limit of 30 at Day 3 and staying below the detection limit through the rest of the time points) were kept. Fluctuation close to the detection limit was ignored (i.e., if the read count of a sgRNA was less than or equal to the mean read counts of sgRNAs that are below the detection limit+2*standard deviation of the read counts of sgRNAs that are below the detection limit, the sgRNA was considered not detected). Genes were selected if they had sufficient numbers of sgRNAs depleted (1 out of 1 total sgRNAs, 1 out of 2 total sgRNAs, 1 out of 3 total sgRNAs, 2 out of 4 total sgRNAs, 2 out of 5 total sgRNAs, or 3 out of 6 total sgRNAs). Genes were retained if selected in at least 2 out of 3 repeat time course experiments. Next, genes were identified as "essential" if sgRNAs targeting those genes were depleted in both Agg[+] and Agg[−]. Genes were identified as "synthetic lethal" if sgRNAs targeting those genes were depleted in Agg[+] but not Agg[−] (no depletion in Agg[−] as compared to Agg[+]; refinement based on multiple repeats and manual inspection). By refinement is meant taking the genes that presented in all three repeated time-course experiments in the Agg[+] cell line and then excluding any gene that presented in at least one experiment in the Agg[−] cell line. Manual inspection involved reviewing the guide RNAs shown to be depleted in one of the Agg[+] experiments, looking for guide RNAs depleted in all Agg[+] experiments but in no Agg[−] experiments or in only one Agg[−] experiment, and confirming that no targets were missed.

There was no strong or systematic perturbation with the 1000 non-targeting control sgRNAs (data not shown). Specifically, for each of Days 6, 7, 10, 11, 13, 14, and 17 versus Day 3, all experimental repeats were combined from both Agg[+] and Agg[−]. P-values (adjusted for multiple testing) of changes in read counts were calculated. No gRNA at any time point had a p value <0.05.

Figure 13:
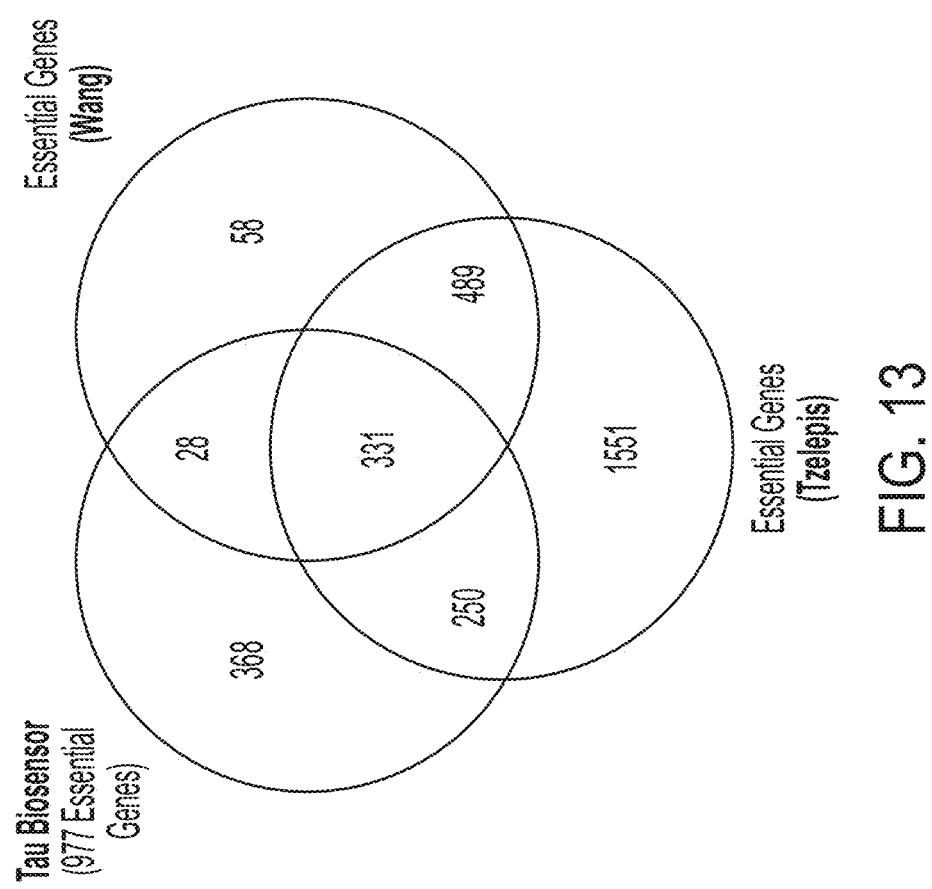
FIG. 13 is a graph showing the overlap of essential genes identified in the Tau biosensor screen compared to other published reports.

Time course analysis revealed 977 genes as "essential" genes with sgRNAs having temporal patterns of depletion in both Agg[+] and Agg[−] subclones (data not shown). These genes identified as "essential" significantly overlap with genes identified as essential in public datasets (see, e.g., Tzelepis et al. (2016) Cell Reports 17:1193-1205 and Wang et al. (2015) Science 350(6264):1096-1101, each of which is herein incorporated by references in its entirety for all purposes). See FIG. 13 and Table 5.

TABLE 5

Overlap of Essential Genes with Public Datasets.

| Public Dataset | # Genes Overlapping with Tau Biosensor Essential Genes | P-Value |
|---|---|---|
| Essential in Wang | 359 | 2e−249 |
| Essential in Tzelepis | 581 | 9e−276 |
| Essential shared by Wang & Tzelepis | 331 | 5e−231 |

Figure 14:
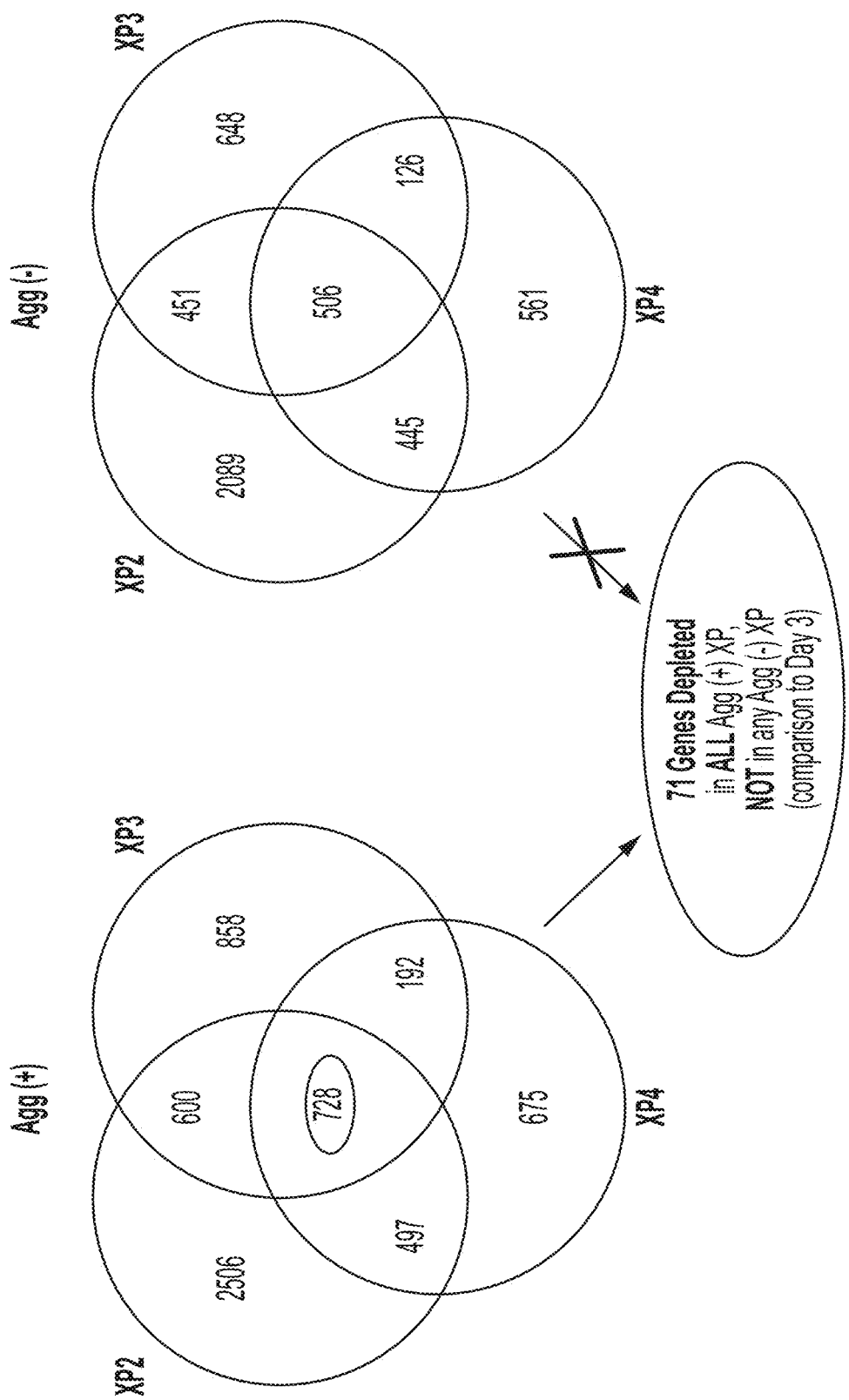
FIG. 14 is a graph showing the identification of 71 genes with uniquely depleted sgRNAs over time in comparison to Day 3 in Agg[+] samples compared to Agg[−] samples in three repeat experiments.
Figure 15A:
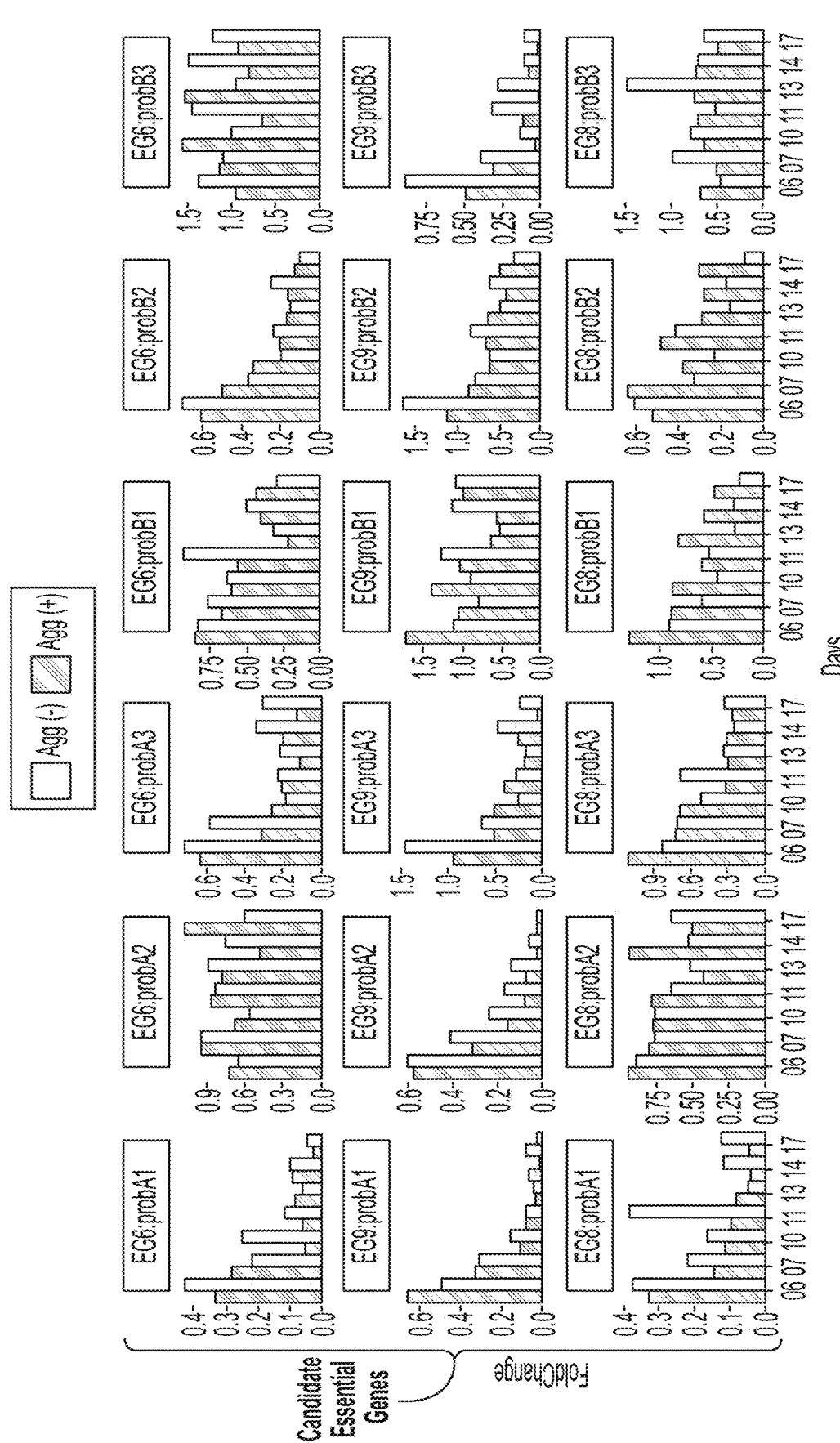
FIGS. 15A and 15B show the fold change over time (sgRNA depletion) relative to Day 3 in Agg[+] and Agg[−] cells for sgRNAs targeting three candidate essential genes (Essential Genes 6, 8, and 9 (EG6, EG8, and EG9)
Figure 15B:
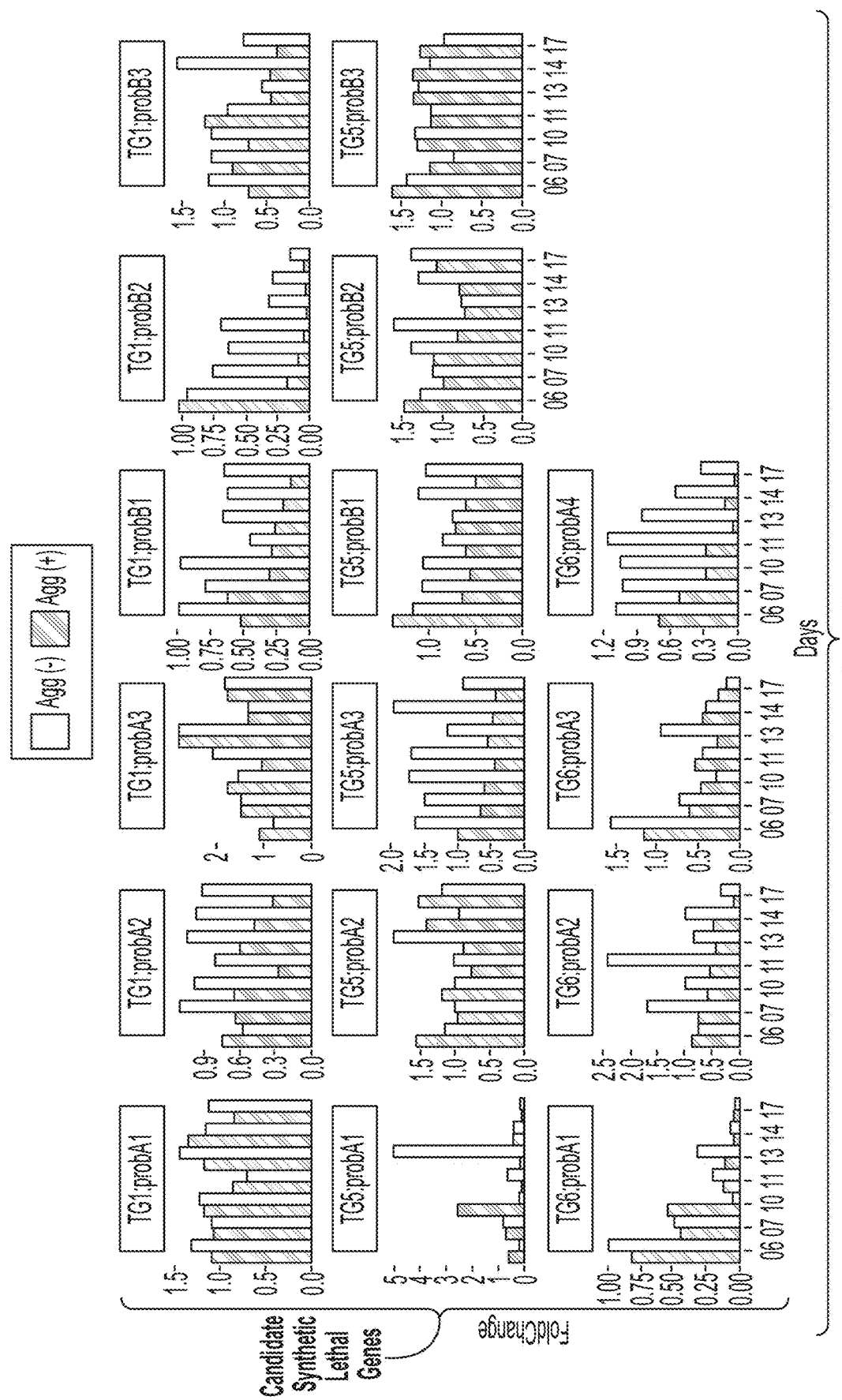

Genes targeted by multiple sgRNAs exhibiting a pattern of depletion in multiple replicate screens in Agg[+] but not in Agg[−] were selected for further validation in a secondary screen as "synthetic lethal" genes. Seventy-one genes were identified as being depleted in all Agg[+] experimental replicates in comparison to Day 3 but not in any Agg[−] experimental replicates. See FIG. 14. The data for three target genes (Target Gene 1, Target Gene 5, and Target Gene 6) are shown in FIG. 15B.

Figure 16:
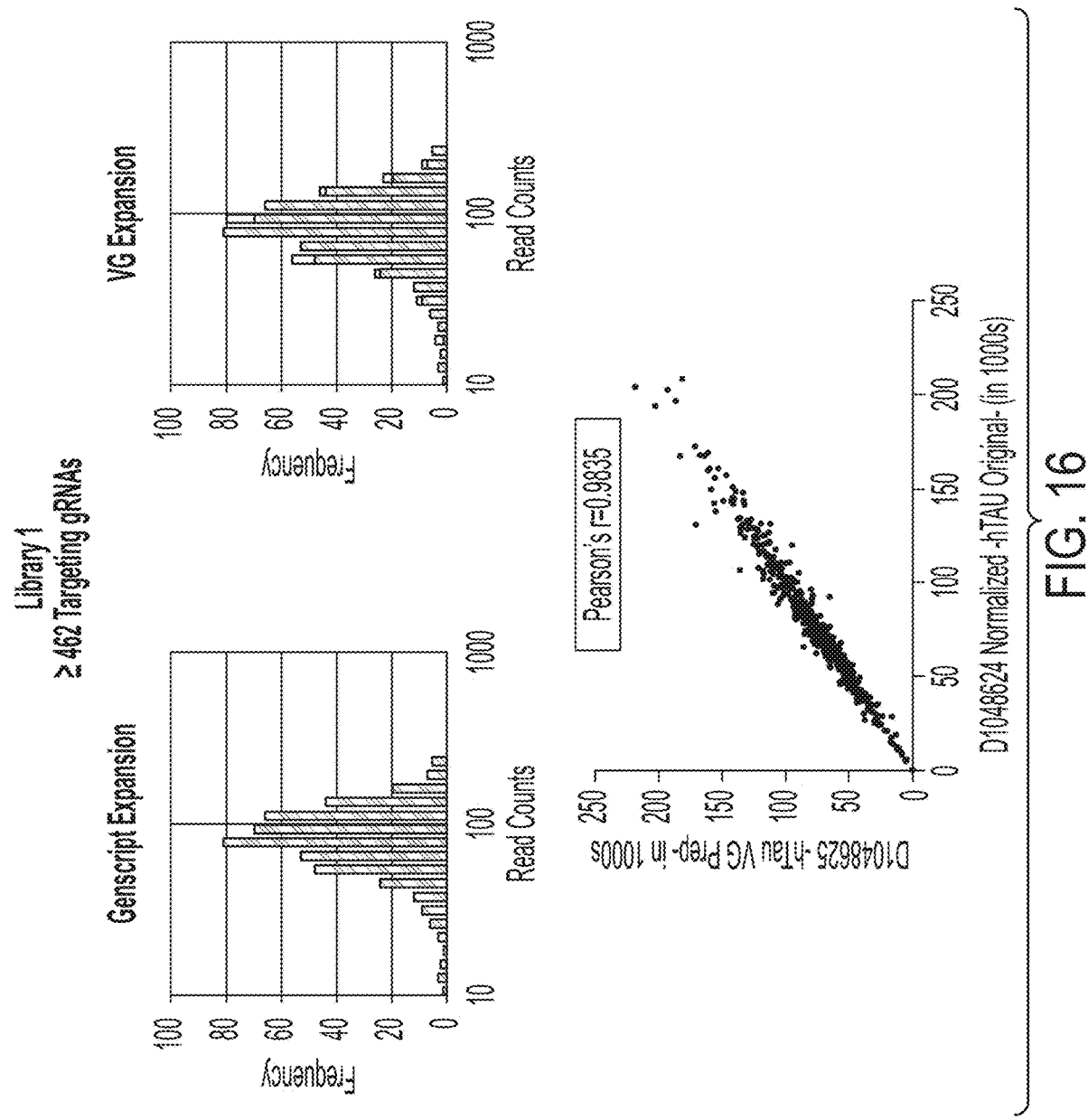
FIG. 16 shows read count distribution of the custom sgRNA library consisting of 462 unique targeting sgRNAs targeting 71 putative synthetic lethal genes (for which sgRNAs were selectively depleted in Agg[+] cells in the primary screening) and 10 putative essential genes (for which sgRNAs were depleted in both Agg[+] and Agg[−] cells in the primary screening).
Figure 17:
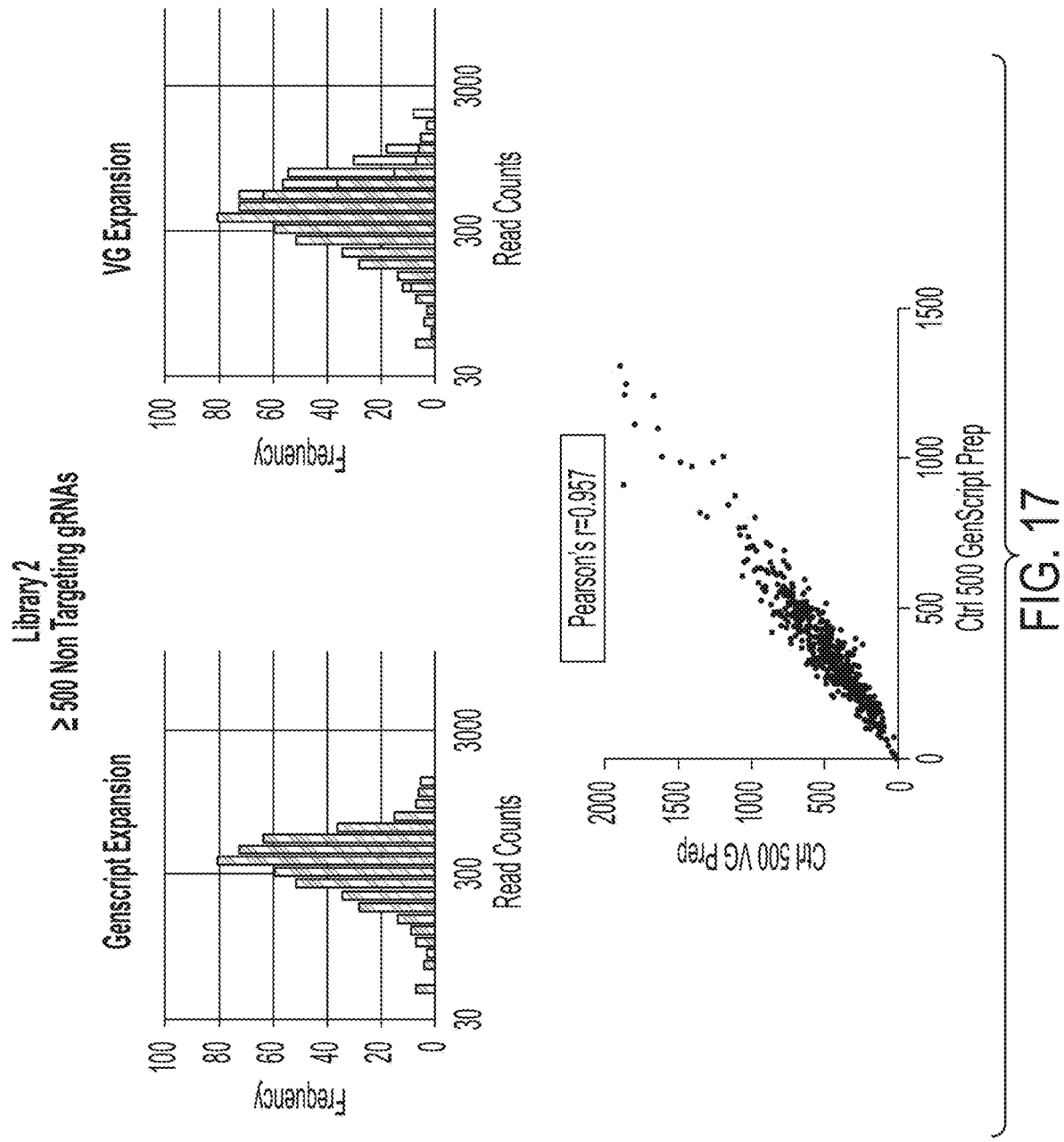
FIG. 17 shows read count distribution of a sgRNA library consisting of 500 unique non-targeting control sgRNAs (non-specific sgRNAs that were not altered over time in the primary screening).

These 71 genes were identified by analysis of sgRNA depletion in three replicates, depletion of sgRNAs over multiple time points, and visual inspection of data. Custom GenScript mini-libraries were then generated. Library 1 contained 462 unique targeting sgRNAs (targeting the 71 putative synthetic lethal genes with sgRNAs identified as selectively depleted in Agg[+] cells and 10 putative essential genes with sgRNAs identified as depleted in both Agg[+] and Agg[−] cells, each targeted by ~6 unique sgRNAs). Library 2 contained 500 unique non-targeting control sgRNAs that were not altered over the time course experiment. Read count distribution of the two libraries is shown in FIGS. 16 and 17, respectively. This shows that the representation of the two libraries is maintained after expansion. Pearson's r describe the statistical correlation between the original library and after expansion.

Figure 18:
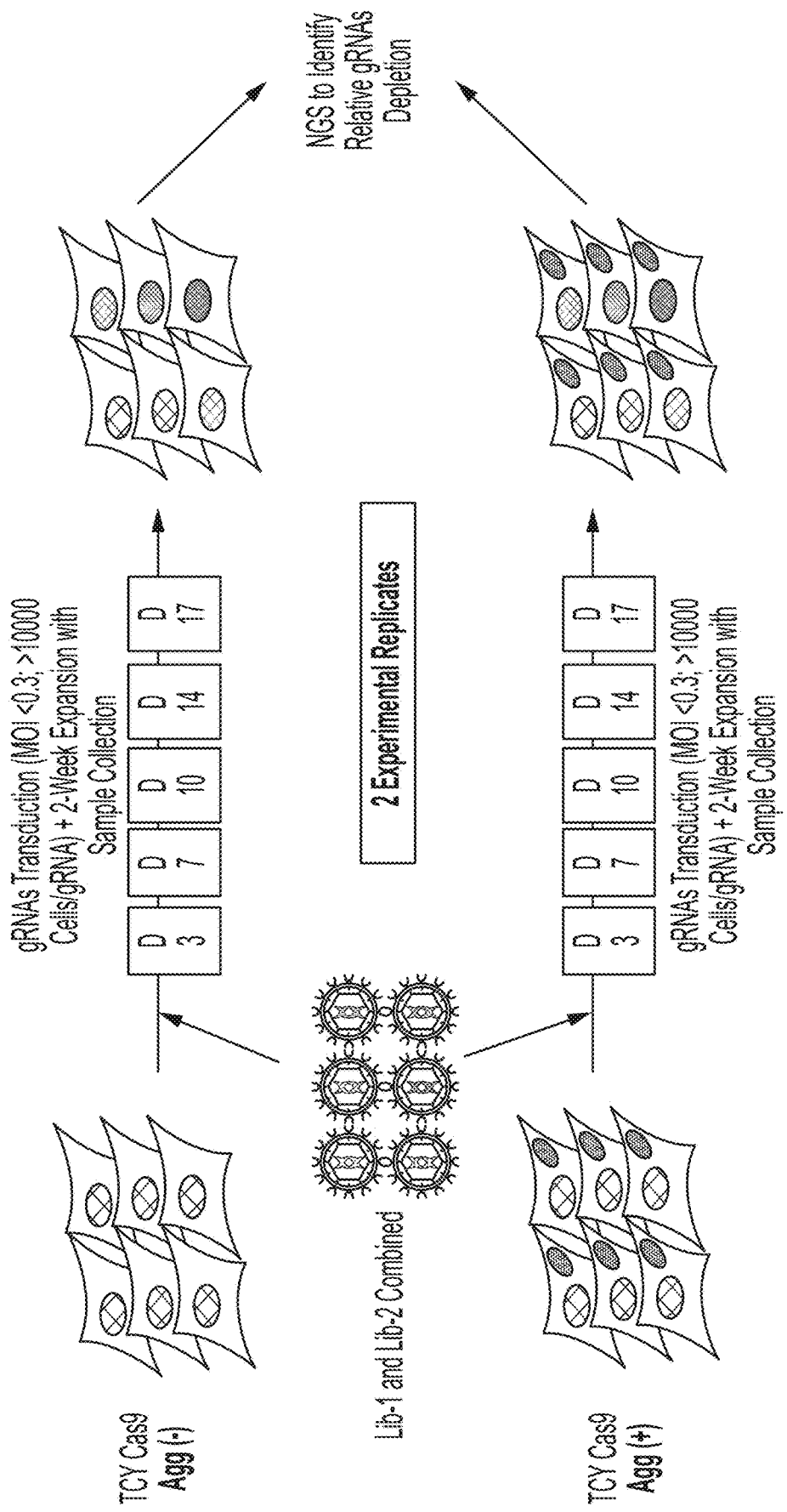
FIG. 18 shows a general schematic of the secondary screen to validate the 71 putative synthetic lethal genes and the 10 putative essential genes using the custom sgRNA libraries.
Figure 19A:
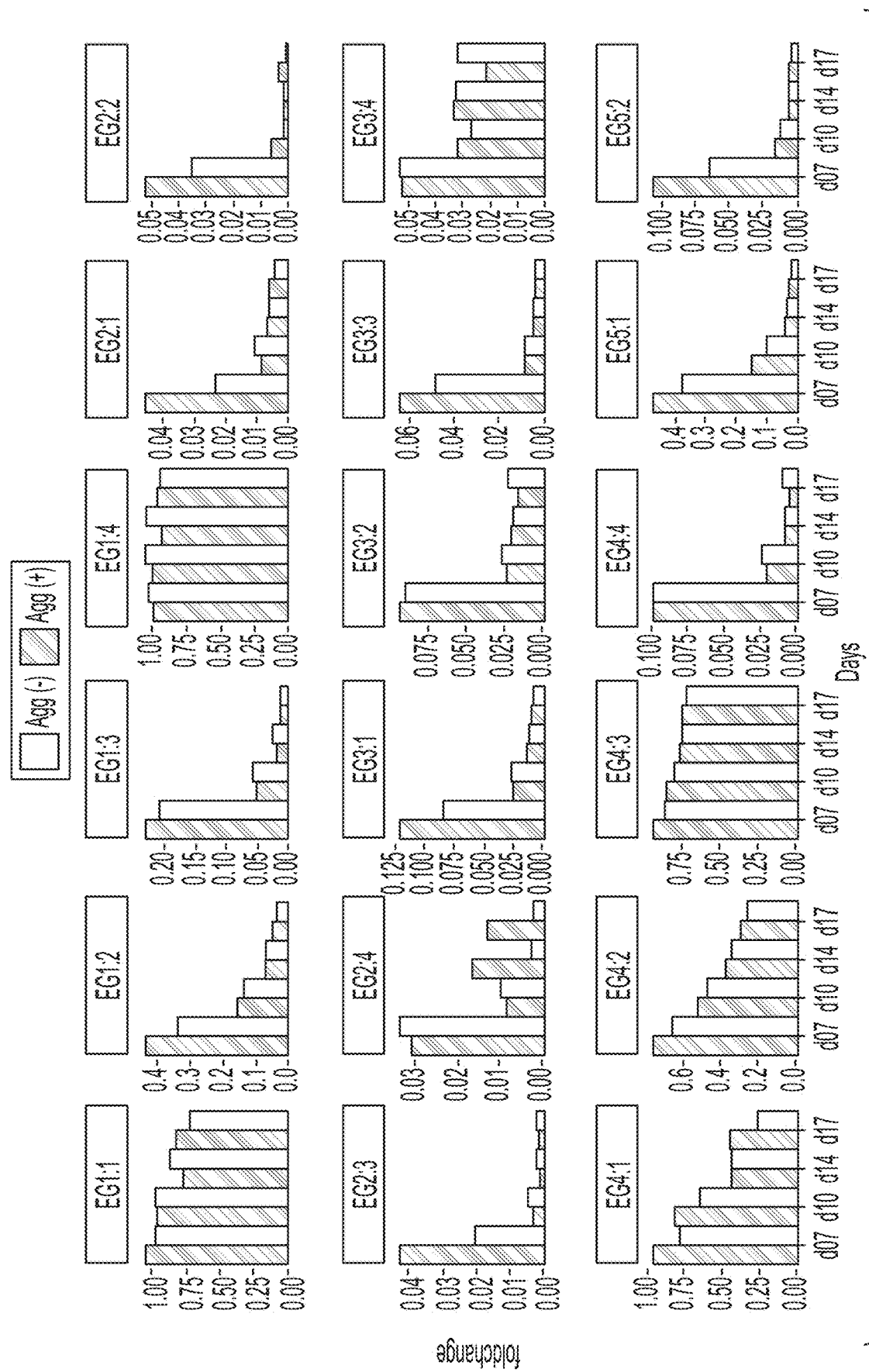
FIGS. 19A-19C show the fold change over time (sgRNA depletion) relative to Day 3 in Agg[+] and Agg[−] cells for sgRNAs targeting ten candidate essential genes (EG1-EG10) in the secondary screen.
Figure 19B:
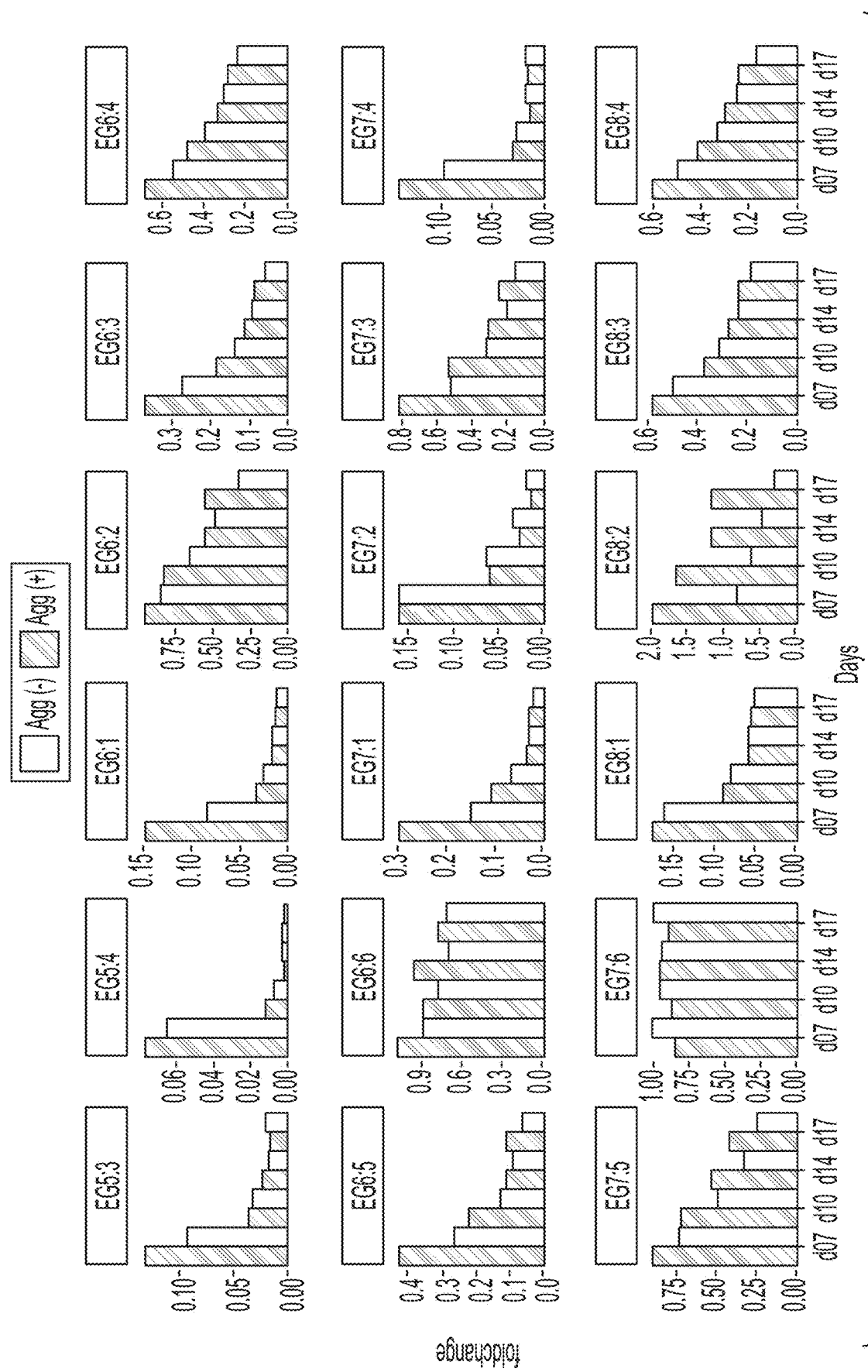
Figure 19C:
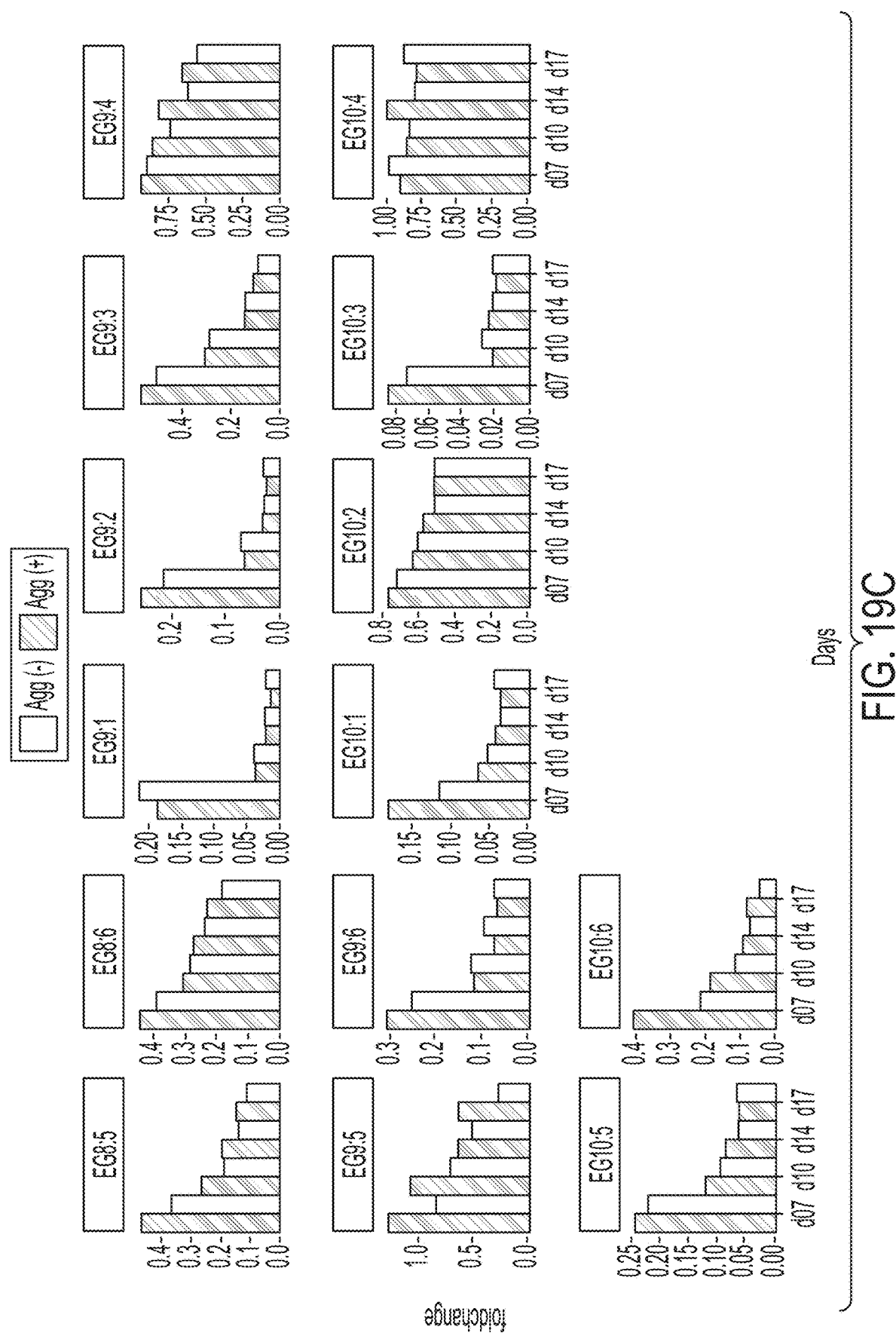

The libraries were then used for a secondary screen of the candidate targets. See FIG. 18. Depletion of targeting sgRNAs relative to non-targeting control sgRNAs was assessed throughout a 17-day time-course approach in (Agg[+]) and (Agg[−]) clones at a high representation of 10,000× cells per sgRNA. Depletion of sgRNAs to target genes relative to control sgRNAs was assessed throughout the time course in both Agg[+] and Agg[−] clones. First, read counts were normalized by the sum of the non-targeting sgRNAs. The normalization involved multiplying a scalar number to each sample (different samples can have different scalar numbers) such that after the normalization the total read counts over all non-targeting sgRNAs per sample were the same. After such normalization, non-targeting sgRNAs showed no change as expected, and many targeting sgRNAs showed time-wise depletion patterns. Using normalization by sum of the non-targeting sgRNAs, only a small number of non-targeting sgRNAs showed perturbation (perturbation criteria: p value ≤0.01; fold change ≥1.2). The pattern was random, and the magnitude was small. Besides visually (qualitatively) showing no perturbations in the non-targeting sgRNAs, this showed by statistical analysis (p value and fold change) at Day 7 versus Day 3, Day 10 versus Day 3, Day 14 versus Day 3, and Day 17 versus Day 3 that only a small number of non-targeting sgRNAs were perturbed. In addition, which sgRNAs at which time point were perturbed (relative to Day 3) was rather random because the heat map did not show a temporal pattern for any of these perturbed sgRNAs (data not shown). Next, the 10 putative "essential" genes were validated by assessing sgRNA depletion in both Agg[+] and Agg[−] samples. Time course data from replicates for sgRNAs for the ten genes are shown in FIGS. 19A-19C.

Figure 20:
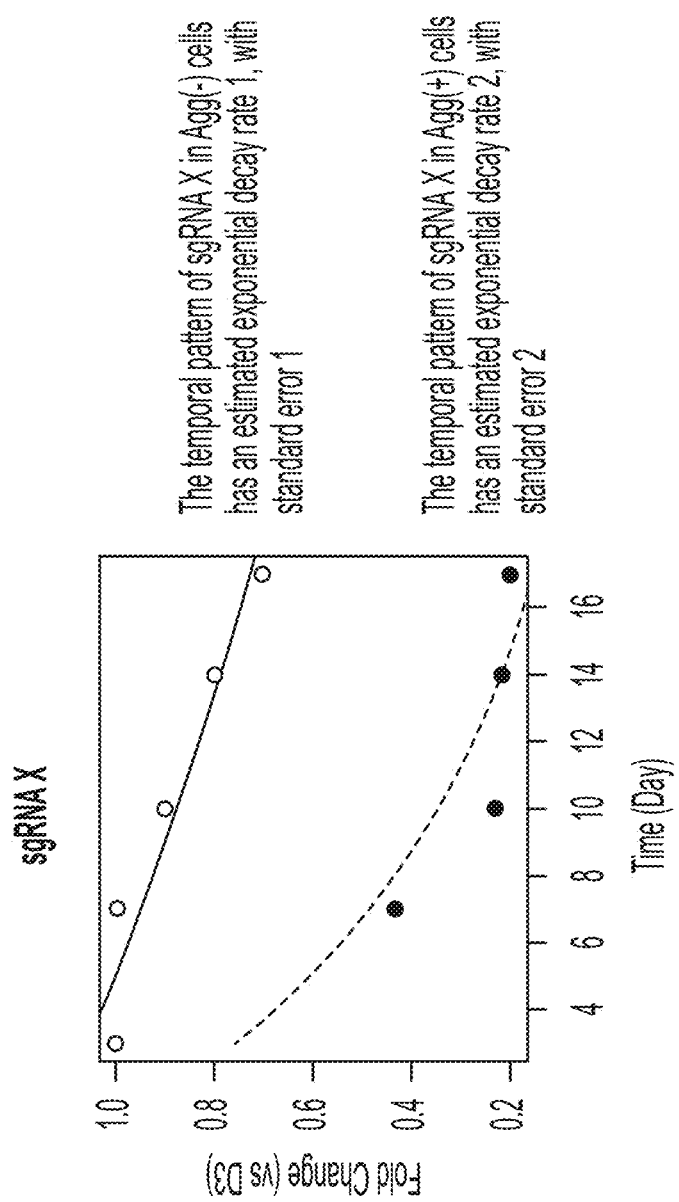
FIG. 20 shows an example of a graph showing a distinguishable depletion pattern for a sgRNA between Agg[+] cells and Agg[−] cells (i.e., more dramatic depletion in Agg[+] cells).

Next, patterns of depletion were assessed for the candidate synthetic lethal genes. For each sgRNA, the significance (p value) of the time factor was calculated (two experiments were used as repeats per time point). A standard general linear regression model (GLM) was used: y beta*t, where y=read count and t=time, was applied to the data (two repeated experiments at the five time points (Day 3 to Day 17)). Solving the GLM resulted in a p-value for beta that defines how significantly beta is apart from 0 (i.e., the significance of the time factor). In addition, each sgRNA was marked if it had a depleting pattern in every experiment (Day 10<Day 3; AND Day 14<Day 7, AND Day 17<Day 10). sgRNAs were selected if they had a significant time course p value ($\leq 1e^{-3}$) and a depleting pattern in every experiment. sgRNAs were then selected if they had a distinguishable depletion pattern between Agg[+] and Agg [−] (differential test on fitted exponential decay rates). To determine whether there was a distinguishable depletion pattern, the following steps were used: (1) in both Agg[+] and Agg[−] cells, for each sgRNA X, average its read counts over two repeated experiments at each time point; (2) fit the five-time-point data from (1) to an exponential decay model: Read count=exp(−rate*t) to estimate the rate, resulting in an expected value of the rate (e.g., rate 1) and its associated standard error (e.g., standard error 1); and (3) if [rate 1]/[rate 2]≥1.5 or ≤1/1.5, and ([rate 1]−[rate 2])/sqrt([standard error 1]$^2$+[standard error 2]$^2$)≥1.96 or ≤−1.96, then rate1 and rate2 are statistically different. An example of a distinguishable depletion pattern (i.e., a more dramatic or sharper depletion pattern in Agg[+] cells) is shown in FIG. 20. Genes were then selected based on the number of sgRNAs selected (2 out of 4 total sgRNAs targeting a gene, or 3 out of 6 total sgRNAs targeting a gene).

Figure 21:
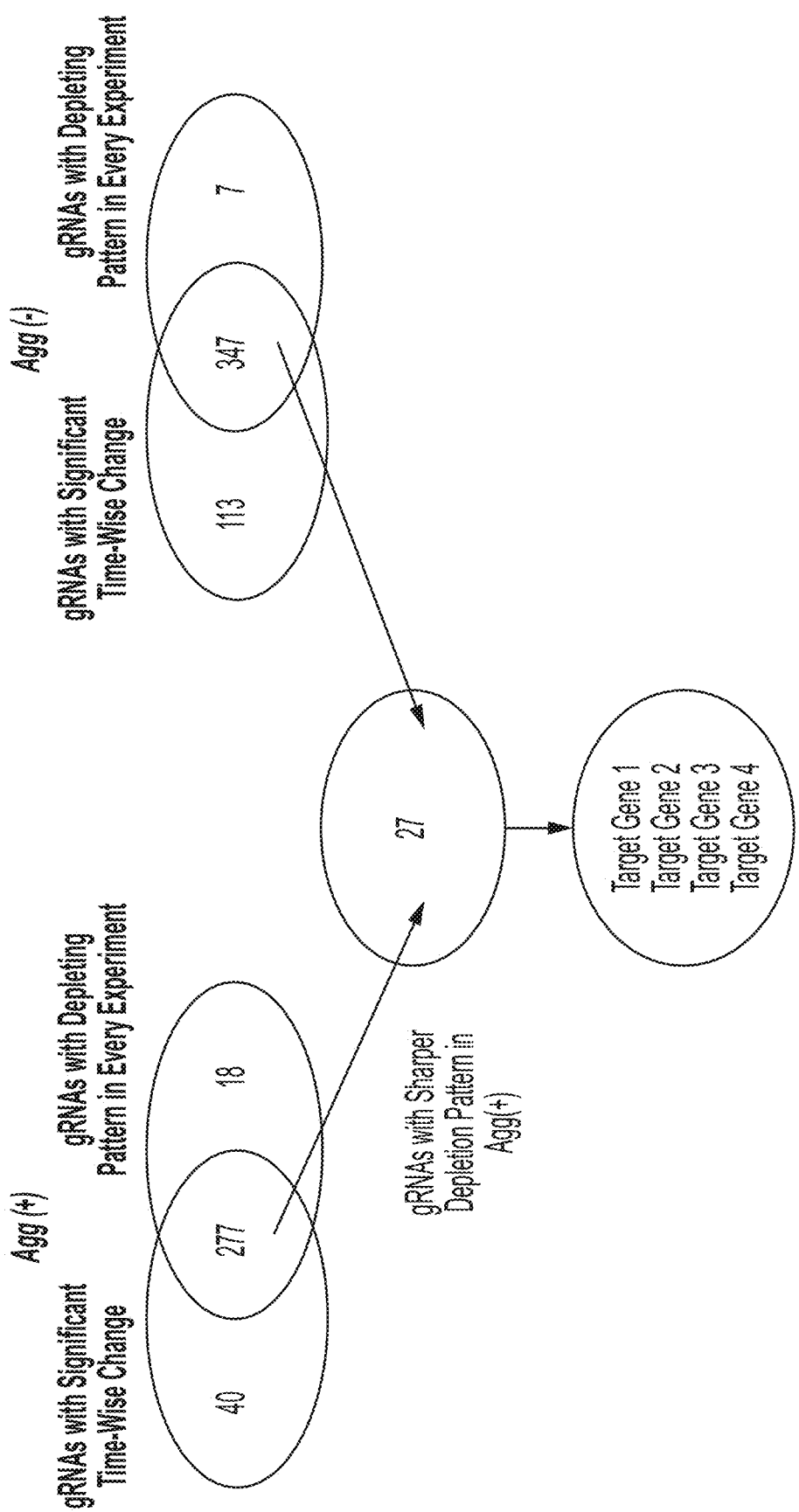
FIG. 21 shows a general schematic for identification of synthetic lethal genes in the secondary screen by identifying sgRNAs that demonstrate both a significant time course p-value and a depleting pattern in every experiment (Day 10<Day 3, Day 14<Day 7, and Day 17<Day 10).
Figure 22A:
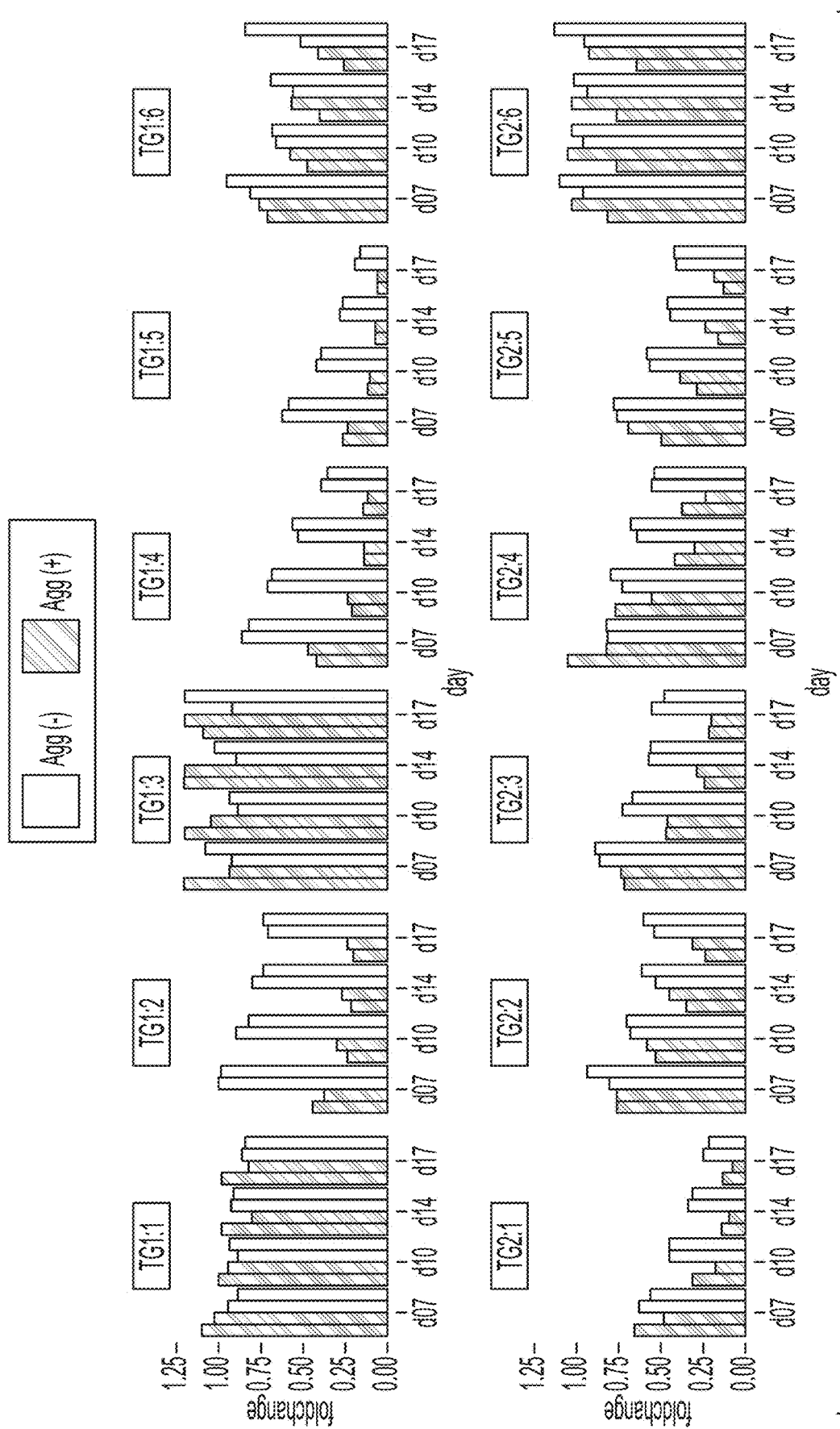
FIG. 22A shows the fold change over time (sgRNA depletion) in Agg[+] and Agg[−] cells for six sgRNAs targeting Target Gene 1 (TG1) and six sgRNAs Target Gene 2 (TG2).
Figure 22B:
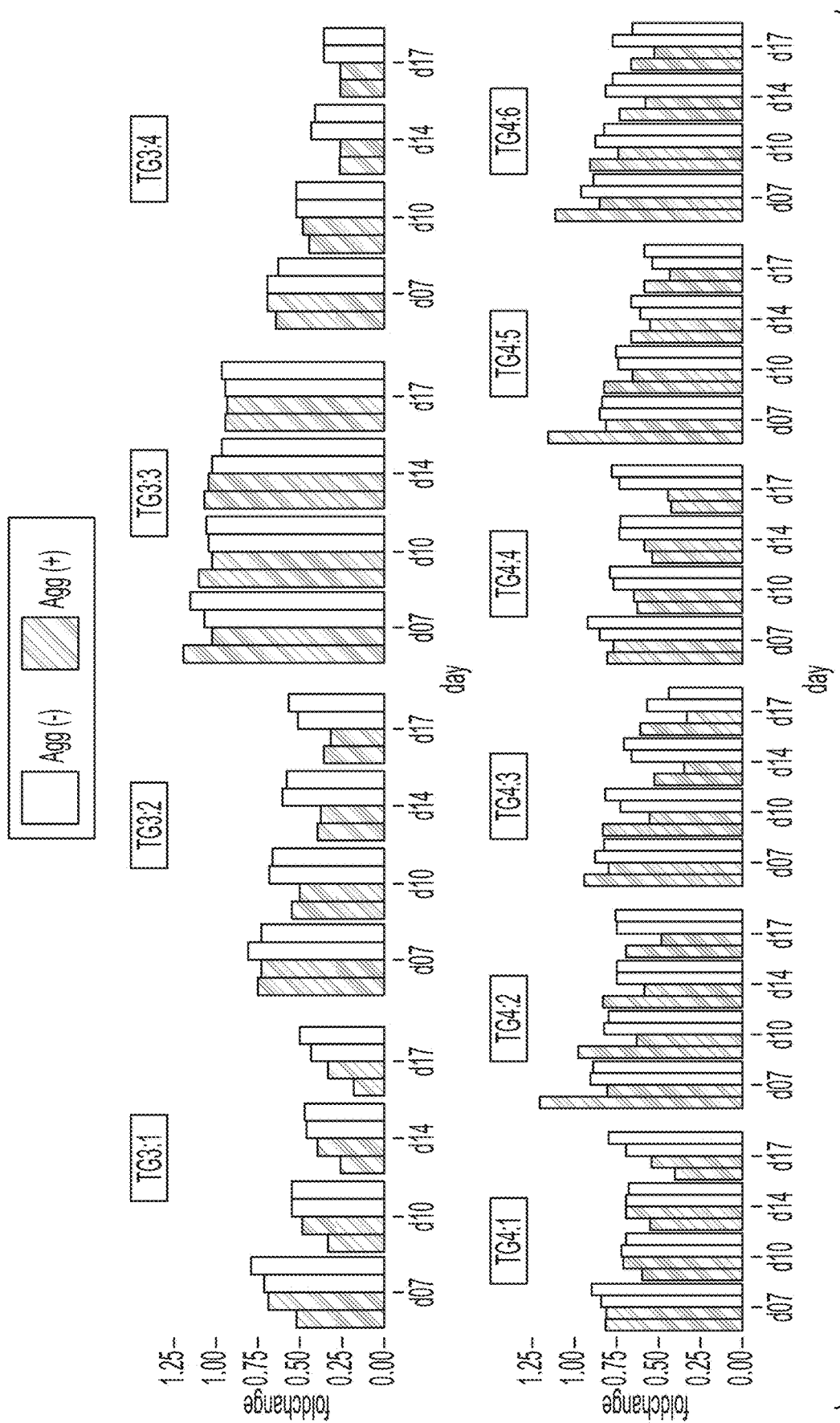
FIG. 22B shows the fold change over time (sgRNA depletion) in Agg[+] and Agg[−] cells for six sgRNAs targeting Target Gene 3 (TG3) and six sgRNAs Target Gene 4 (TG4).

Twenty-seven sgRNAs were identified as having sharper depletion patterns in Agg[+] compared to Agg[−]. See FIG. 21. Of these, four target genes were selected for further validation (Target Gene 1, Target Gene 2, Target Gene 3, and Target Gene 4) based on the number of sgRNAs selected (2 out of 4 total sgRNAs targeting a gene, or 3 out of 6 total sgRNAs targeting a gene). The validation for Target Genes 1 and 2 is shown in FIG. 22A, and the validation for Target Genes 3 and 4 is shown in FIG. 22B. The 10 essential genes were also validated by a secondary screening method (data not shown).

Figure 25:
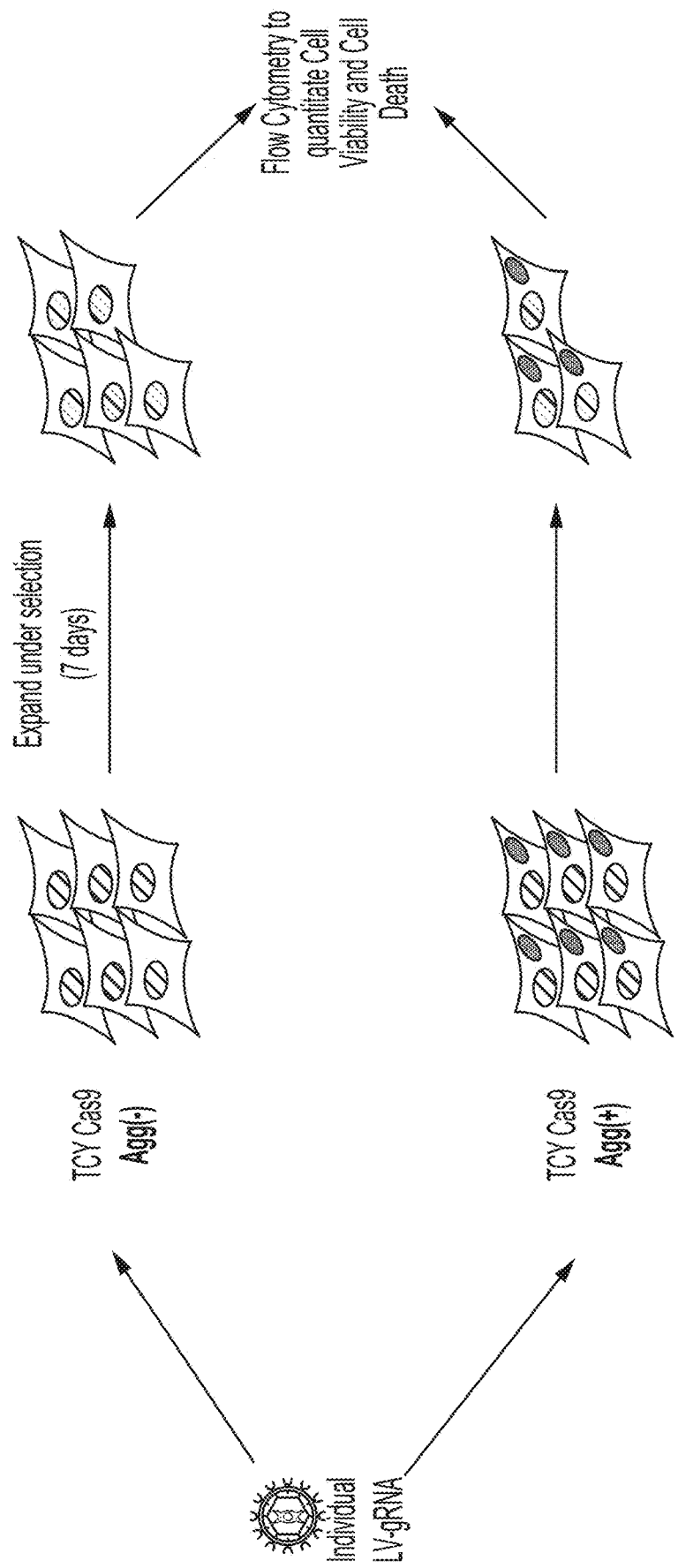
FIG. 25 shows a schematic for further validating Target Genes 1, 2, and 4, using flow cytometry to quantitate cell viability and cell death in Agg[+] cells and Agg[−] cells following transduction with lentiviral vectors delivering sgRNAs targeting Target Genes 1, 2, and 4.
Figure 26:
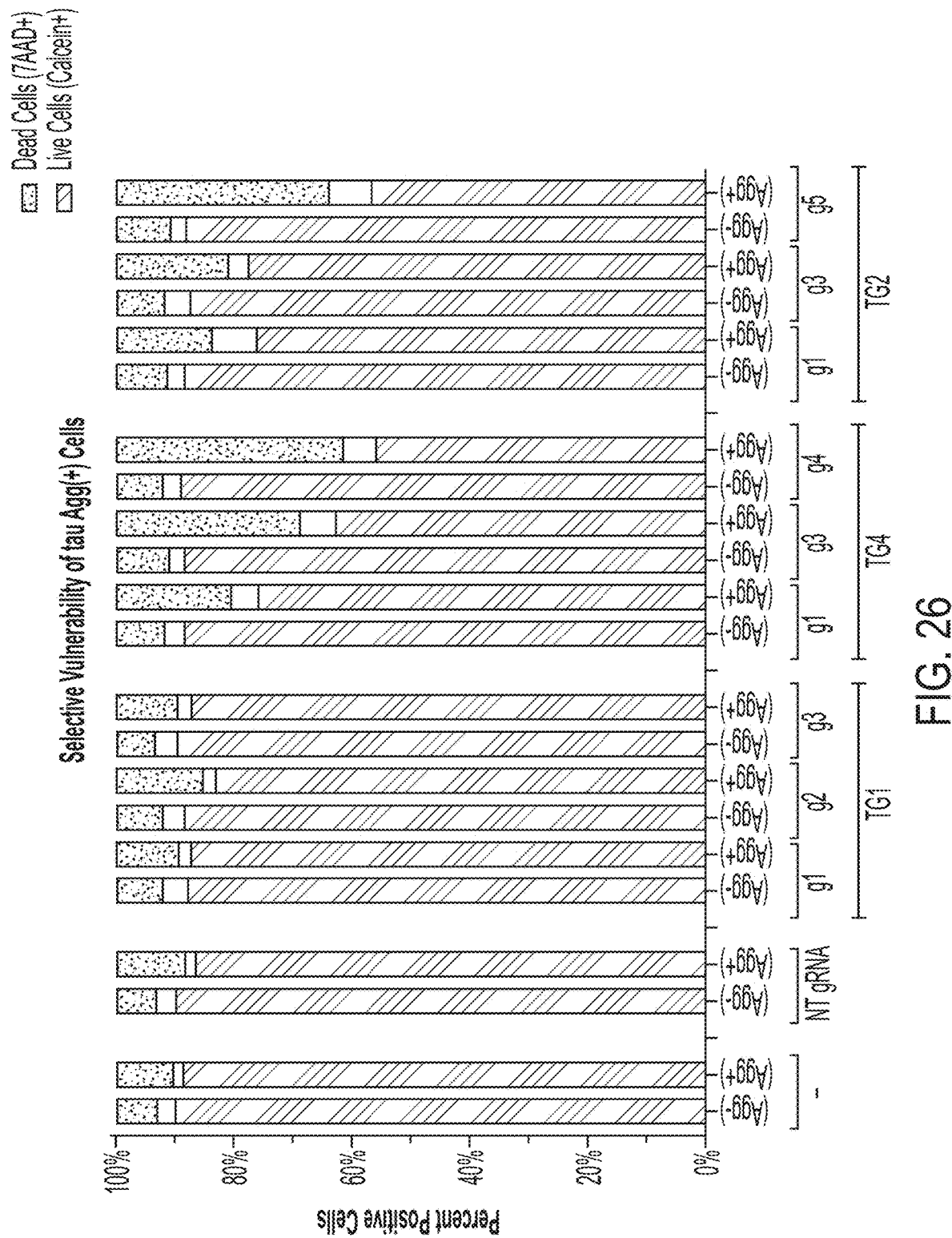
FIG. 26 shows cell viability and cell death in Agg[+] cells and Agg[−] cells following transduction with lentiviral vectors delivering sgRNAs targeting Target Genes 1, 2, and 4.

For further validation, the Cas9-expressing Tau-CFP/Tau-YFP biosensor cells, either with aggregates (Agg[+]) or without aggregates (Agg[−]), were transduced with sgRNAs targeting Target Gene 1, Target Gene 2, and Target Gene 4 using a lentiviral delivery approach to introduce knock-out mutations at each target gene (FIG. 25). Following expansion under selection for 7 days, cell viability and cell death was assessed and quantified by flow cytometry (FIG. 26), and decreases in expression of the target genes was assessed and confirmed (data not shown). The sgRNAs targeting Target Gene 1, Target Gene 2, and Target Gene 4 caused selective cell death in the Agg[+] cells but not in the Agg[−] cells.

Example 3. Development of a Genome-Wide CRISPR/Cas9 Screening Platform to Identify Genetic Modifiers of Tau Affecting Cell Viability Using a Transcriptional Activation CRISPR/Cas9 Library To identify genes that when transcriptionally activated exhibit synthetic lethality with disease-associated protein aggregates, a platform was developed for performing genome-wide screens with transcriptional activation (hSAM) CRISPRa sgRNA libraries. The platform identifies genes that, upon transcriptional activation, cause cell death specifically in the context of abnormal protein aggregation. The identification of such genes may elucidate the mechanisms of aggregate-associated neurotoxicity, and genetic pathways that promote death of neurons in the context of neurodegenerative disease.

The screen employed a Tau biosensor human cell line consisting of HEK293T cells stably expressing Tau four-repeat domain, Tau 4RD, comprising the Tau microtubule binding domain (MBD) with the P301S pathogenic mutation, fused to either CFP or YFP. That is, the HEK293T cell lines contain two transgenes stably expressing disease-associated protein variants fused to the fluorescent protein CFP or the fluorescent protein YFP: Tau$^{4RD}$-CFP/Tau$^{4RD}$-YFP (TCY), wherein the Tau repeat domain (4RD) comprises the P301S pathogenic mutation. See FIG. 1. In these biosensor lines, Tau-CFP/Tau-YFP protein aggregation produces a FRET signal, the result of a transfer of fluorescent energy from donor CFP to acceptor YFP. See FIG. 2. FRET-positive cells, which contain Tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal. Aggregate-containing cells can be isolated by FACS. Stably propagating aggregate-containing cell lines, Agg[+], can be isolated by clonal serial dilution of Agg[−] cell lines.

Several modifications were made to this Tau biosensor cell line to make it useful for genetic screening. First, this biosensor cell line was further transgenically modified to express the components of the CRISPR/Cas SAM transcriptional activation system: dCas9-VP64 and MS2-P65-HSF1. Lentiviral dCas9-VP64 and MS2-P65-HSF1 constructs are provided in SEQ ID NOS: 42 and 43, respectively. Clone DC11 was selected as a high-performing clone to use for subsequent library screens. This clone was validated for its efficacy in activating selected target genes.

Second, sub-clones of these SAM-expressing Tau-CFP/Tau-YFP (TCY) biosensor cell lines in which Tau protein is stably present in either a non-aggregated (the default state) (Agg[−]) or an aggregated state (Agg[+]) were obtained. To obtain cell lines in which Tau protein is stably and persistently present in an aggregated state, the SAM-expressing cells were treated with recombinant fibrillized Tau mixed with lipofectamine reagent in order to "seed" the aggregation of the Tau protein transgenically expressed by these cells. The "seeded" cells were then serially diluted to obtain single cell-derived clones, and these clones were then expanded to identify those clonal cell lines in which Tau aggregates stably persist in all cells with growth and multiple passages over time. One of these aggregate-positive Agg[+] stable clones, DC11-B6, was selected for expansion and use in screening.

Example 4. Genome-Wide CRISPR/Cas9 Screening Platform to Identify Genetic Modifiers of Tau Affecting Cell Viability Using a Transcriptional Activation CRISPR/Cas9 Library A pooled genome-wide transcriptional activation (hSAM) CRISPRa screen was performed to reveal genetic modifiers of Tau affecting cell viability using the clonal cell lines developed in Example 3. Specifically, the SAM-expressing (i.e., dCas9-VP64/MS2-P65-HSF1-expressing) Tau-CFP/Tau-YFP biosensor cells, either with aggregates (Agg[+]) or without aggregates (Agg[−]), were transduced with a human genome-wide CRISPR hSAM sgRNA library using a lentiviral delivery approach to transcriptionally activate each target gene at a representation of 500× cells per sgRNA. The CRISPR hSAM sgRNA library targets sites within 200 bp upstream of the transcription start site with an average coverage of 3-4 sgRNAs per gene. The sgRNAs were designed to avoid off-target effects by avoiding sgRNAs with two or fewer mismatches to off-target genomic sequences. The library covers 18,946 human genes. The library was transduced at a multiplicity of infection (MOI) <0.3 at a coverage of >500 cells per sgRNA. Tau biosensor cells were grown under zeocin selection to select cells with integration and expression of a unique sgRNA per cell.

Samples of (Agg[+]) and (Agg[−]) cells were collected at five time points: Days 3, 6, 7, 14, and 17 post-transduction. DNA isolation and PCR amplification of the integrated sgRNA constructs allowed a characterization by next generation sequencing (NGS) of the sgRNA repertoire in each cell line at each time point. The screening consisted of 4 replicated experiments. Analysis of the NGS data enabled the identification of genes which, upon transcriptional activation, lead to cell death. sgRNAs that are depleted in both cell lines are likely disrupting some cell process essential for cell viability, while sgRNAs that are depleted specifically in the Agg[+] cell line, while not or less-depleted in the Agg[−] cell line, may indicate a synthetic lethal effect, in which the activation of a specific target gene combines with the presence of Tau aggregates in the cell to induce cell death. These synthetic lethal genes are of interest as potential modifiers of Tau-associated cell toxicity.

The data analysis mirrored the approach used in Example 2 and included (1) sgRNA profiling in two cell population Agg[+] and Agg[−] throughout a time-course of 17 days and (2) sgRNA profiling in Agg[+] compared to Agg[−] at different time points or at the final time point compared to Day 3. Because the data analysis mirrored the approach used in Example 2, not all of the details from Example 2 are repeated here.

As explained in Example 2, this is a novel analytical approach to evaluating sgRNA depletion, as compared to the more conventional approach of simply comparing the NGS reads of the endpoint cell collection to the first passage. In comparison, other published genome-wide CRISPR screens for depletion have compared CRISPR scores as the ratio of read counts between final collection and early passage. In contrast, our approach was to examine the full time course to identify genes that exhibit a pattern of sgRNA depletion over time.

Depleted genes were then identified via time course analysis. In each repeat, depleted sgRNAs with non-increasing temporal patterns (read count at Day 10≤at Day 3; read count at Day 14≤at Day 7; and read count Day 17≤at Day 10) relative to Day 3 were selected. sgRNAs already depleted at Day3 (i.e., below the detection limit of 30 at Day 3 and staying below the detection limit through the rest of the time points) were kept. Fluctuation close to the detection limit was ignored (i.e., if the read count of a sgRNA was less than or equal to the mean read counts of sgRNAs that are below the detection limit+2*standard deviation of the read counts of sgRNAs that are below the detection limit, the sgRNA was considered not detected). Genes were selected if they had sufficient numbers of sgRNAs depleted (1 out of 1 total sgRNAs, 1 out of 2 total sgRNAs, 1 out of 3 total sgRNAs, 2 out of 4 total sgRNAs, 2 out of 5 total sgRNAs, or 3 out of 6 total sgRNAs). Next, genes were identified as "essential" if sgRNAs targeting those genes were depleted in both Agg[+] and Agg[−]. Genes were identified as "synthetic lethal" if sgRNAs targeting those genes were depleted in Agg[+] but not Agg[−] (no depletion in Agg[−] as compared to Agg[+]; refinement based on multiple repeats and manual inspection). By refinement is meant taking the genes that presented in all three repeated time-course experiments in the Agg[+] cell line and then excluding any gene that presented in at least one experiment in the Agg[−] cell line. Manual inspection involved reviewing the guide RNAs shown to be depleted in one of the Agg[+] experiments, looking for guide RNAs depleted in all Agg[+] experiments but in no Agg[−] experiments or in only one Agg[−] experiment, and confirming that no targets were missed.

Genes targeted by multiple sgRNAs exhibiting a pattern of depletion in multiple replicate screens in Agg[+] but not in Agg[−] were identified as candidate "synthetic lethal" genes. Next, patterns of depletion were assessed for the candidate synthetic lethal genes. For each sgRNA, the significance (p value) of the time factor was calculated (two experiments were used as repeats per time point). A standard general linear regression model (GLM) was used: y beta*t, where y=read count and t=time, was applied to the data (two repeated experiments at the five time points (Day 3 to Day 17)). Solving the GLM resulted in a p-value for beta that defines how significantly beta is apart from 0 (i.e., the significance of the time factor). In addition, each sgRNA was marked if it had a depleting pattern in every experiment (Day 10<Day 3; AND Day 14<Day 7, AND Day 17<Day 10). sgRNAs were selected if they had a significant time course p value ($\leq 1e^{-3}$) and a depleting pattern in every experiment. sgRNAs were then selected if they had a distinguishable depletion pattern between Agg[+] and Agg[−] (differential test on fitted exponential decay rates). To determine whether there was a distinguishable depletion pattern, the following steps were used: (1) in both Agg[+] and Agg[−] cells, for each sgRNA X, average its read counts over two repeated experiments at each time point; (2) fit the five-time-point data from (1) to an exponential decay model: Read count=exp(−rate*t) to estimate the rate, resulting in an expected value of the rate (e.g., rate 1) and its associated standard error (e.g., standard error 1); and (3) if [rate 1]/[rate 2]≥1.5 or ≤1/1.5, and ([rate 1]−[rate 2])/sqrt([standard error 1]$^2$+[standard error 2]$^2$)≥1.96 or ≤−1.96, then rate1 and rate2 are statistically different. An example of a distinguishable depletion pattern (i.e., a more dramatic or sharper depletion pattern in Agg[+] cells) is shown in FIG. 20.

Figure 23:
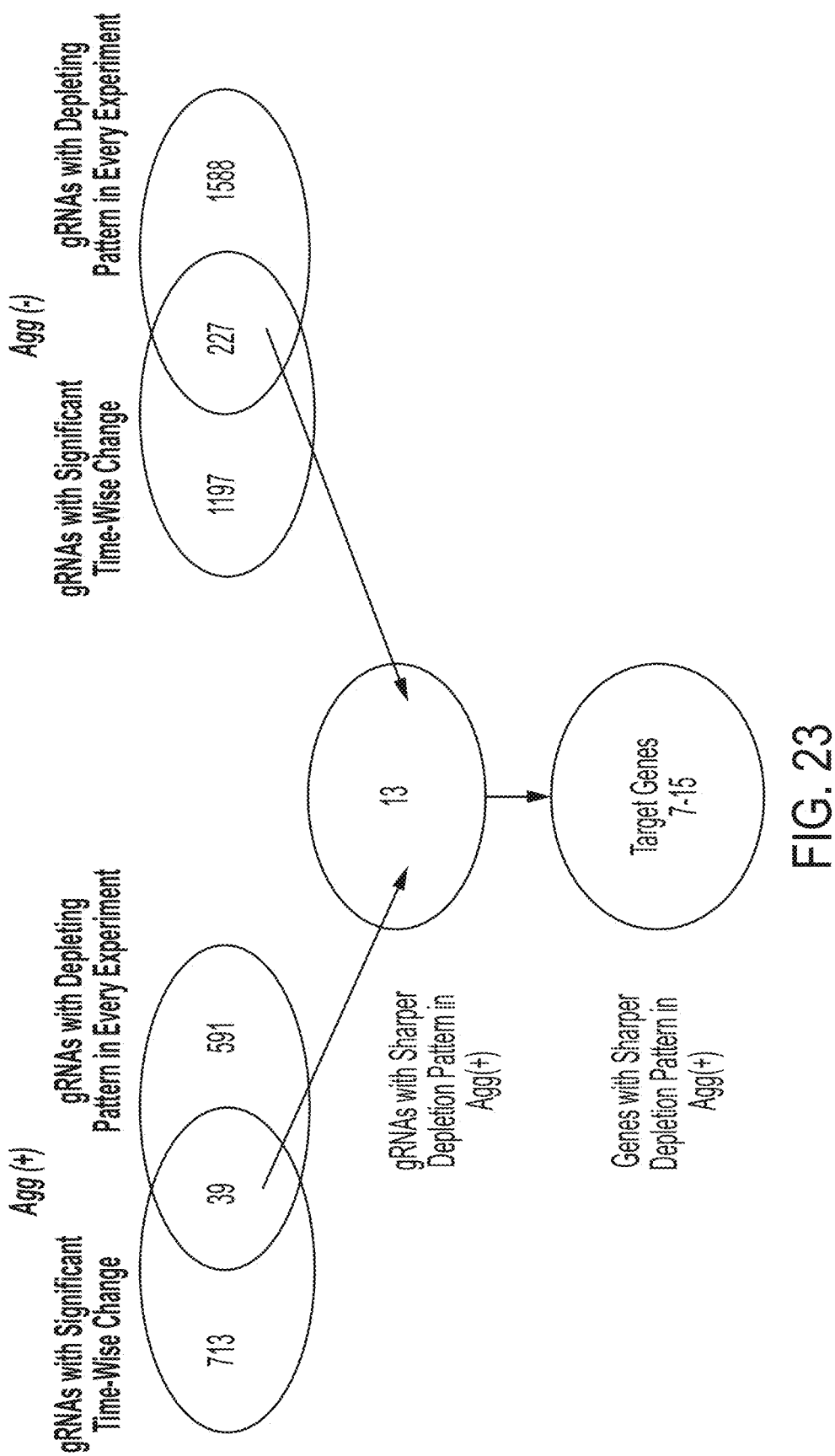
FIG. 23 shows a general schematic for identification of synthetic lethal genes in the secondary screen by identifying CRISPRa sgRNAs that demonstrate both a significant time course p-value and a depleting pattern in every experiment (Day 10<Day 3, Day 14<Day 7, and Day 17<Day 10).
Figure 24A:
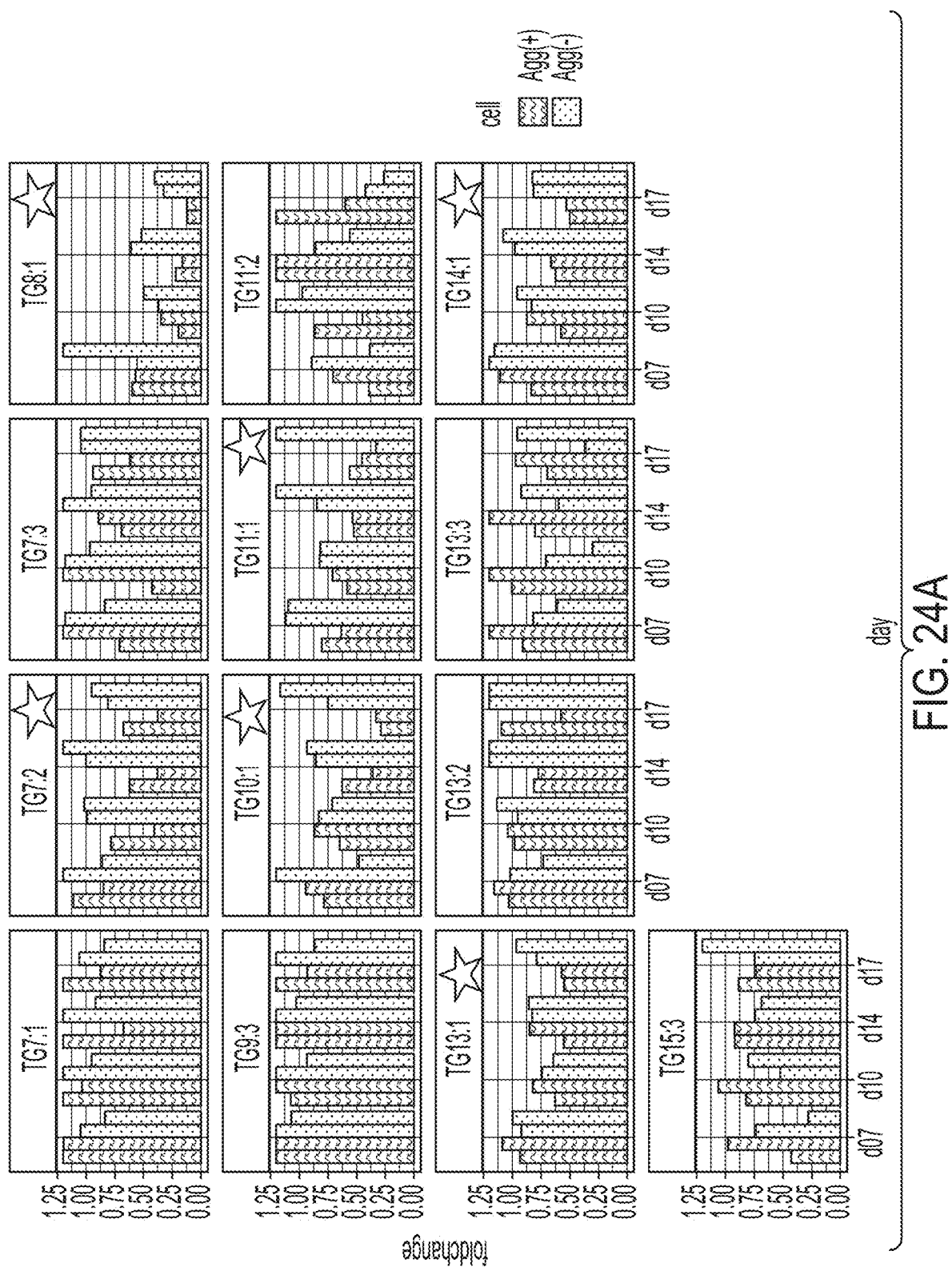
FIGS. 24A and 24B show the fold change over time (sgRNA depletion) in Agg[+] and Agg[−] cells for sgRNAs targeting Target Genes 7-15 (TG7-TG15).
Figure 24B:
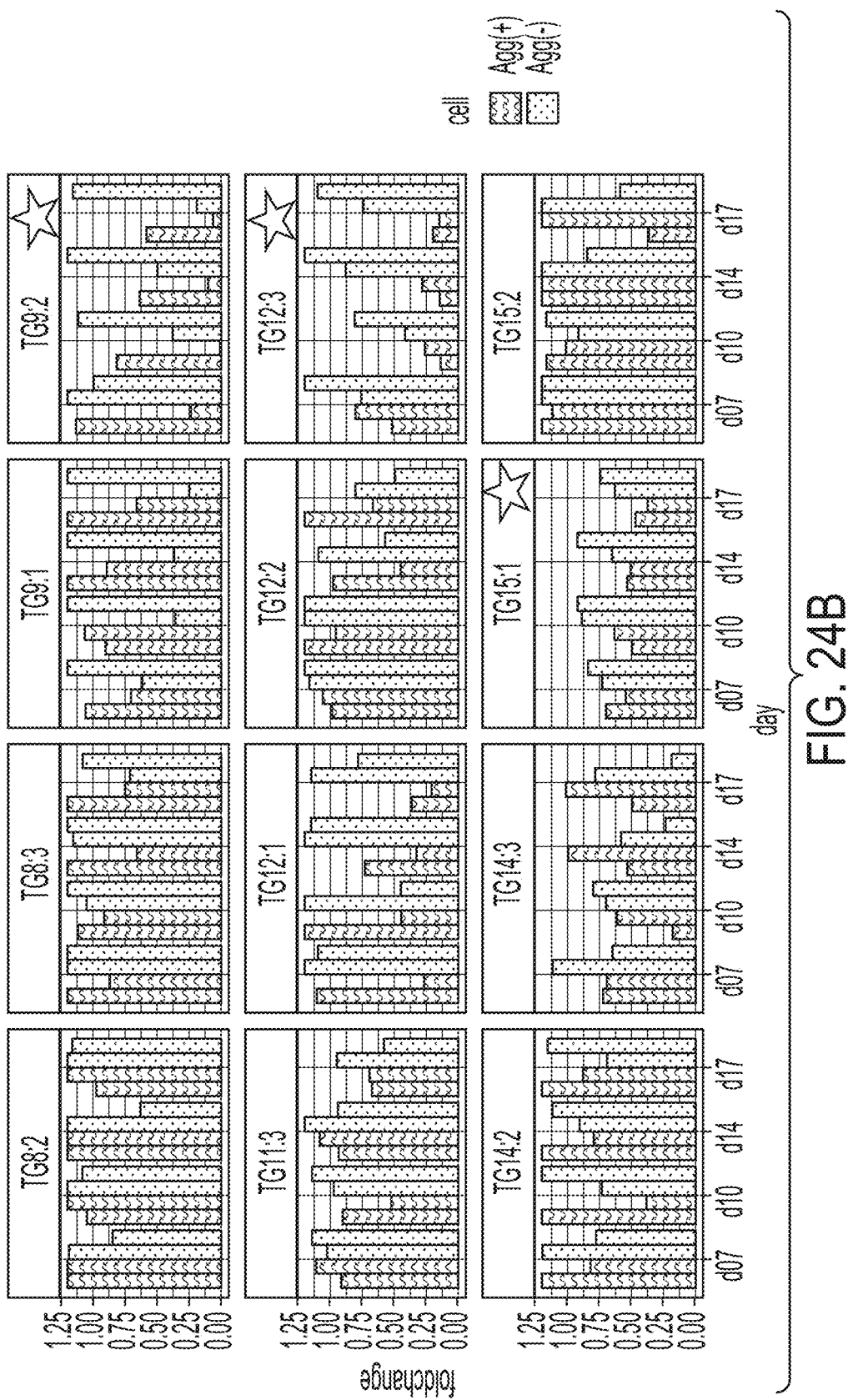

Thirteen sgRNAs representing nine target genes (Target Genes 7-15) were identified as having sharper depletion patterns in Agg[+] compared to Agg[−]. See FIG. 23. The validation for Target Genes 7-15 is shown in FIGS. 24A-24B.

We claim:

1. A method of screening for genetic vulnerabilities associated with tau aggregation, comprising:
   (a) providing an aggregation-positive population of cells and an aggregation-negative population of cells, wherein each population of cells comprises a Cas protein, a first tau repeat domain linked to a first reporter, and a second tau repeat domain linked to a second reporter,
   wherein the cells are mammalian cells,
   wherein the first reporter and the second reporter are fluorescent proteins, and wherein the first reporter and the second reporter are a fluorescence resonance energy transfer (FRET) pair,
   wherein in the aggregation-positive population of cells the first tau repeat domain linked to the first reporter and the second tau repeat domain linked to the second reporter stably present in an aggregated state, and
   wherein in the aggregation-negative population of cells the first tau repeat domain linked to the first reporter and the second tau repeat domain linked to the second reporter do not stably present in an aggregated state;
   (b) introducing into each population of cells a library comprising a plurality of unique guide RNAs that target a plurality of genes, wherein the plurality of unique guide RNAs form complexes with the Cas protein, and the Cas protein cleaves the plurality of genes resulting in knockout of gene function; and
   (c) determining abundance of each of the plurality of unique guide RNAs at a plurality of time points over a time course in each population of cells,
   wherein the plurality of time points comprises at least three time points, wherein there is more than 1 day between each time point,
   wherein depletion of a guide RNA in the aggregation-positive population of cells but not in the aggregation-negative population of cells or a more dramatic depletion pattern of a guide RNA over the time course in the aggregation-positive population of cells relative to the aggregation-negative population of cells indicates that the gene targeted by the guide RNA exhibits synthetic lethality with tau protein aggregates and is a genetic vulnerability associated with tau aggregation.

2. The method of claim 1, wherein the Cas protein is a Cas9 protein.

3. The method of claim 2, wherein the Cas protein is *Streptococcus pyogenes* Cas9, wherein the Cas protein comprises SEQ ID NO: 21 or wherein the Cas protein is encoded by a coding sequence comprising the sequence set forth in SEQ ID NO: 22.

4. The method of claim 1, wherein the Cas protein, the first tau repeat domain linked to the first reporter, and the second tau repeat domain linked to the second reporter are stably expressed in the populations of cells and are genomically integrated in the population of cells.

5. The method of claim 1, wherein each guide RNA targets a 5' constitutive exon or wherein each guide RNA targets a first exon, a second exon, or a third exon.

6. The method of claim 1, wherein the first tau repeat domain and/or the second tau repeat domain is a human tau repeat domain.

7. The method of claim 1, wherein the first tau repeat domain and/or the second tau repeat domain comprises a pro-aggregation mutation, wherein the pro-aggregation mutation is a tau P301S mutation.

8. The method of claim 1, wherein the first tau repeat domain and/or the second tau repeat domain comprises a tau four-repeat domain.

9. The method of claim 1, wherein the first tau repeat domain and/or the second tau repeat domain comprises SEQ ID NO: 11.

10. The method of claim 1, wherein the first tau repeat domain and the second tau repeat domain are the same and each comprises a tau four-repeat domain comprising a tau P301S mutation.

11. The method of claim 1, wherein the first reporter is cyan fluorescent protein (CFP) and the second reporter is yellow fluorescent protein (YFP).

12. The method of claim 1, wherein the cells are human cells.

13. The method of 12, wherein the cells are HEK293T cells.

14. The method of claim 1, wherein the plurality of unique guide RNAs are introduced at a concentration selected such that a majority of the cells receive only one of the unique guide RNAs.

15. The method of claim 1, wherein the plurality of unique guide RNAs target 100 or more genes, 1000 or more genes, or 10000 or more genes.

16. The method of 1, wherein the library is a genome-wide library.

17. The method of claim 1, wherein a plurality of target sequences are targeted on average in each of the targeted plurality of genes.

18. The method of claim 17, wherein at least three target sequences are targeted on average in each of the targeted plurality of genes or wherein about three to about six target sequences are targeted on average in each of the targeted plurality of genes.

19. The method of claim 1, wherein the plurality of unique guide RNAs are introduced into the populations of cells by lentiviral transduction, wherein each of the plurality of unique guide RNAs is in a separate viral vector.

20. The method of claim 19, wherein the populations of cells are infected at a multiplicity of infection of less than about 0.3.

21. The method of claim 1, wherein the plurality of unique guide RNAs are introduced into the populations of cells together with a selection marker that imparts resistance to a drug, and step (b) further comprises selecting cells that comprise the selection marker.

22. The method of claim 1, wherein the populations of cells into which the plurality of unique guide RNAs are introduced in step (b) each comprise greater than about 500 cells per unique guide RNA.

23. The method of claim 1, wherein the time course in step (c) is more than about 1 week.

24. The method of claim 23, wherein the time course in step (c) is more than about 2 weeks.

25. The method of claim 1, wherein the time course in step (c) comprises about 10 to about 15 cell doublings.

26. The method of claim 1, wherein the plurality of time points in step (c) comprises about four time points or about six time points.

27. The method of claim 1, wherein there is more than about 2 days between each time point in step (c).

28. The method of claim 27, wherein there is between about 3 to about 4 days between each time point in step (c).

29. The method of claim 1, wherein a gene is considered to exhibit synthetic lethality with tau protein aggregates in step (c) if a guide RNA targeting the gene is depleted in the aggregation-positive population of cells but not in the aggregation-negative population of cells.

30. The method of claim 29, wherein a gene is considered to exhibit synthetic lethality with tau protein aggregates in step (c) if a guide RNA targeting the gene has a more dramatic depletion pattern over the time course in the aggregation-positive population of cells relative to the aggregation-negative population of cells.

31. The method of claim 1, wherein a guide RNA is considered depleted in step (c) if the abundance of the guide RNA at each time point is less than or equal to the abundance of the guide RNA at the preceding time point.

32. The method of claim 1, wherein a guide RNA is considered depleted in step (c) if the abundance of the guide RNA at each time point after the second time point is less than or equal to the abundance of the time point two time points prior.

33. The method of claim 1, wherein a gene is considered to exhibit synthetic lethality with tau protein aggregates in step (c) if more than about 30% of the guide RNAs in the library that target the gene are depleted in the aggregation-positive population of cells but not in the aggregation-negative population of cells.

34. The method of claim 33, wherein a gene is considered to exhibit synthetic lethality with tau protein aggregates in step (c) in any one of the following situations:
(1) there is one guide RNA in the library that targets the gene, and the one guide RNA is depleted in the aggregation-positive population of cells but not in the aggregation-negative population of cells;
(2) there are two guide RNAs in the library that target the gene, and at least one of the two guide RNAs is depleted in the aggregation-positive population of cells but not in the aggregation-negative population of cells;
(3) there are three guide RNAs in the library that target the gene, and at least one of the three guide RNAs is depleted in the aggregation-positive population of cells but not in the aggregation-negative population of cells;
(4) there are four guide RNAs in the library that target the gene, and at least two of the four guide RNAs is depleted in the aggregation-positive population of cells but not in the aggregation-negative population of cells;
(5) there are five guide RNAs in the library that target the gene, and at least two of the five guide RNAs is depleted in the aggregation-positive population of cells but not in the aggregation-negative population of cells; and
(6) there are six guide RNAs in the library that target the gene, and at least three of the six guide RNAs is depleted in the aggregation-positive population of cells but not in the aggregation-negative population of cells.

35. The method of claim 1, wherein the method is repeated at least three times in at least three different experiments, and a gene is considered to exhibit synthetic lethality with tau protein aggregates if it is considered to exhibit synthetic lethality with tau protein aggregates in more than about 50% of the at least three different experiments.

36. The method of claim 1, wherein the time course in step (c) is more than about 2 weeks,
wherein the plurality of time points in step (c) comprises about six time points,
wherein there is between about 3 to about 4 days between each time point in step (c),
wherein a guide RNA is considered depleted in step (c) if the abundance of the guide RNA at each time point after the second time point is less than or equal to the abundance of the time point two time points prior, and
wherein a gene is considered to exhibit synthetic lethality with tau protein aggregates in step (c) if more than about 30% of the guide RNAs in the library that target the gene are depleted in the aggregation-positive population of cells but not in the aggregation-negative population of cells.

* * * * *